US012612624B2

(12) United States Patent
Liu et al.

(10) Patent No.:  US 12,612,624 B2
(45) Date of Patent:      Apr. 28, 2026

(54) LIGHT-INDUCIBLE CRISPR/Cas9 SYSTEM FOR GENOME EDITING

(71) Applicant: The Johns Hopkins University, Baltimore, MD (US)

(72) Inventors: Yang Liu, Baltimore, MD (US); Roger Zou, Baltimore, MD (US); Bin Wu, Baltimore, MD (US); Taekjip Ha, Baltimore, MD (US)

(73) Assignee: THE JOHNS HOPKINS UNIVERSITY, Baltimore, MD (US)

( * ) Notice:     Subject to any disclaimer, the term of this patent is extended or adjusted under 35 U.S.C. 154(b) by 1009 days.

(21) Appl. No.:     17/770,512

(22) PCT Filed:     Oct. 25, 2020

(86) PCT No.:      PCT/US2020/057256
§ 371 (c)(1),
(2) Date:      Apr. 20, 2022

(87) PCT Pub. No.: WO2021/081469
PCT Pub. Date: Apr. 29, 2021

(65) Prior Publication Data
US 2022/0403378 A1      Dec. 22, 2022

Related U.S. Application Data

(60) Provisional application No. 62/926,412, filed on Oct. 25, 2019.

(51) Int. Cl.
*C12N 15/11*      (2006.01)
*C12N 9/22*      (2006.01)
*C12N 15/90*      (2006.01)

(52) U.S. Cl.
CPC ............. *C12N 15/111* (2013.01); *C12N 9/22* (2013.01); *C12N 15/902* (2013.01); *C12N 2310/20* (2017.05); *C12N 2310/3511* (2013.01); *C12N 2320/11* (2013.01)

(58) Field of Classification Search
CPC ........................ C12N 2310/20; C12N 2320/52
See application file for complete search history.

(56) References Cited

U.S. PATENT DOCUMENTS

| | | |
|---|---|---|
| 4,897,355 A | 1/1990 | Eppstein et al. |
| 4,946,787 A | 8/1990 | Eppstein et al. |
| 5,034,613 A | 7/1991 | Denk et al. |
| 5,049,386 A | 9/1991 | Eppstein et al. |
| 5,168,062 A | 12/1992 | Stinski |
| 5,385,839 A | 1/1995 | Stinski et al. |
| 5,466,468 A | 11/1995 | Schneider et al. |
| 5,580,571 A | 12/1996 | Hostetler |
| 5,626,869 A | 5/1997 | Nyqvist et al. |
| 6,020,591 A | 2/2000 | Harter et al. |
| 6,656,692 B2 | 12/2003 | Erikson et al. |
| 6,890,554 B2 | 5/2005 | Jessee et al. |
| 7,049,480 B1 | 5/2006 | Christmann et al. |
| 7,166,298 B2 | 1/2007 | Jessee et al. |
| 2017/0349894 A1* | 12/2017 | Dahlman ............... C12N 15/85 |

FOREIGN PATENT DOCUMENTS

WO      2011116120 A2      9/2011

OTHER PUBLICATIONS

Govan et al., Optochemical control of RNA interference in mammalian cells. Nucleic Acids Research (2013), 41: 10518-10528 (Year: 2013).*
Deiters et al., Photocaged Morpholino Oligomers for the Light-Regulation of Gene Function in Zebrafish and Xenopus Embryos. J. Am. Chem. Soc. (2010), 132: 15644-15650 (Year: 2010).*
Yin et al., Partial DNA-guided Cas9 enables genome editing with reduced off-target activity. Nature Chemical Biology (2018), 14: 311-316 (Year: 2018).*
Jain et al., Development of Light-Activated CRISPR Using Guide RNAs with Photocleavable Protectors. Angew. Chem. Int. Ed. ( 2016), 55: 12440-12444 (Year: 2016).*
Hemphill et al., Optical control of CRISPR/Cas9 gene editing. JACS (2015), 137: 5642-5645 (Year: 2015).*
Casey et al., Caged siRNAs for spatiotemporal control of gene silencing. Molecular Pharmaceutics (2009), 6: 669-685 (Year: 2009).*
Moroz-Omori et al., Photoswitchable gRNAs for spatiotemporally controlled CRISPR-Cas-based genomic regulation. ACS Cent. Sci. (2020), 6: 695-703 (Year: 2020).*
Wiedenheft et al., CRISPR control of virulence in Pseudomonas aeruginosa. Cell Research (2017), 27: 163-164 (Year: 2017).*
Strohkendl et al., Kinetic basis for DNA target specificity of CRISPR-Cas12aMolecular Cell (2018), 71: 816-824 (Year: 2018).*
Čepaitė et al., Structural variation of types IV-A1-and IV-A3-mediated CRISPR interference. Nature Communications (2024), 15: 9306 (Year: 2024).*
Zhang et al., Genetic editing and interrogation with Cpf1 and caged truncated pre-tRNA-like crRNA in mammalian cells., Cell Discovery., (2018), pp. 1-10, vol. 4(36).
Liu et al., Very fast CRISPR on demand., Science., (2020), pp. 1265-1269, vol. 368(6496).
Zhou et al., Spatiotemporal Control of CRISPR/Cas9 Function in Cells and Zebrafish using Light-Activated Guide RNA., Angew. Chem.Int.Ed., (2020), pp. 8998-9003, vol. 59(23).
Jinek et al., A programmable dual-RNA-guided DNA endonuclease in adaptive bacterial immunity., Science., (2012), pp. 816-821, vol. 337(6096).

(Continued)

*Primary Examiner* — Catherine Konopka
(74) *Attorney, Agent, or Firm* — Fox Rothschild LLP; Peter F. Corless

(57)      ABSTRACT

A very fast and efficient CRISPR/Cas9 system is provided. Compositions include light-sensitive caged nucleotides at the PAM distal region of guide RNAs (gRNA$^{caged}$) to create artificial mismatches as a "roadblock". Upon light stimulation, the caging group ("roadblock") is removed and the gRNA fully hybridizes with the target DNA. Thus, the pre-bound inactive Cas9/gRNA$^{caged}$ is rapidly converted to active Cas9.

17 Claims, 26 Drawing Sheets

Specification includes a Sequence Listing.

(56)                    References Cited

OTHER PUBLICATIONS

Cong et al., Multiplex genome engineering using CRISPR/Cas systems., Science., (2013), pp. 819-823, vol. 339 (6121).

Doudna et al., The new frontier of genome engineering with CRISPR-Cas9., Science., (2014), pp. 1258096-1-1258096-9, vol. 346(6213).

Dow et al., Inducible in vivo genome editing with CRISPR-Cas9., Nature Biotechnology., (2015), pp. 390-394, vol. 33 (4).

Liu et al., A chemical-inducible CRISPR-Cas9 system for rapid control of genome editing., Nature Chemical Biology., (2016), pp. 980-987, vol. 12.

Zetsche et al., A split-Cas9 architecture for inducible genome editing and transcription modulation., Nature Biotechnology., (2015), pp. 139-142, vol. 33(2).

Nihongaki et al., Photoactivatable CRISPR-Cas9 for optogenetic genome editing., Nature Biotechnology., (2015), pp. 755-760, vol. 33(7).

Hemphill et al., Optical control of CRISPR/Cas9 gene editing., Journal of American Chemical Society., (2015), pp. 5642-5645, vol. 137(17).

Jain et al., Development of Light-Activated CRISPR Using Guide RNAs with Photocleavable Protectors., Angew. Chem. Int. Ed., (2016), pp. 12440-12444, vol. 55(40).

Rose et al., Rapidly inducible Cas9 and DSB-ddPCR to probe editing kinetics., Nature Methods., (2017), pp. 891-896, vol. 17.

Brinkman et al., Easy quantitative assessment of genome editing by sequence trace decomposition., Nucleic Acids Research., (2014), pp. e168, vol. 42(22).

Wu et al., Genome-wide binding of the CRISPR endonuclease Cas9 in mammalian cells., Nature Biotechnology., (2014), pp. 670-676, vol. 32.

Jackson et al., The DNA-damage response in human biology and disease., Nature., (2009), pp. 1071-1107, vol. 461.

Polo et al., Dynamics of DNA damage response proteins at DNA breaks: A focus on protein modifications., Genes Development., (2011), pp. 409-433, vol. 25.

Shen et al., Predictable and precise template-free CRISPR editing of pathogenic variants., Nature., (2018), pp. 646-651, vol. 563.

Allen et al., Predicting the mutations generated by repair of Cas9-induced double-strand breaks., Nature Biotechnology., (2012), pp. 64-72, vol. 37.

Chakrabarti et al., Target-Specific Precision of CRISPR-Mediated Genome Editing., Molecular Cell., (2018), 699-713, vol. 73.

Lin et al., Enhanced homology-directed human genome engineering by controlled timing of CRISPR/Cas9 delivery., eLife., (2014), vol. 3:e04766.

Feng et al., H2AX facilitates classical non-homologous end joining at the expense of limited nucleotide loss at repair junctions., Nucleic Acids Research., (2017), pp. 10614-10633, vol. 45(18).

Kallimasioti-Pazi et al., Heterochromatin delays CRISPR-Cas9 mutagenesis but does not influence the outcome of mutagenic DNA repair., PLoS Biology., (2018), vol. 16:e2005595.

Clarke et al., Enhanced Bacterial Immunity and Mammalian Genome Editing via RNA-Polymerase-Mediated Dislodging of Cas9 from Double-Strand DNA Breaks., Molecular Cell., (2018), pp. 42-55, vol. 71(1).

Tsouroula et al., Temporal and Spatial Uncoupling of DNA Double Strand Break Repair Pathways within Mammalian Heterochromatin., Molecular Cell., (2016), pp. 293-305, vol. 63(2).

Van Den Berg et al., A limited number of double-strand DNA breaks is sufficient to delay cell cycle progression., Nucleic Acids Research., (2018), pp. 10132-10144, vol. 46(19).

Morita et al., 2'-O, 4'-C-Ethylene-bridged nucleic acids (ENA) with nuclease-resistance and high affinity for RNA., Nucleic Acid Research., (2001), pp. 241-242, vol. 1(1).

Schiffer et al., Targeted DNA Mutagenesis for the Cure of Chronic Viral Infections., Journal of Virology., (2012), pp. 8920-8936, vol. 88(17).

Swarts et al., The evolutionary journey of Argonaute proteins., Nature Structural Molecular Biology., (2014), pp. 743-753, vol. 21.

Swarts et al., Argonaute of the archaeon Pyrococcus furiosus is a DNA-guided nuclease that targets cognate DNA., Nucleic Acids Research., (2015), pp. 5120-5129, vol. 43(10).

Makarova et al., Prokaryotic homologs of Argonaute proteins are predicted to function as key components of a novel system of defense against mobile genetic elements., Biology Direct., (2009), vol. 4:29.

Molloy., Bacterial argonaute sets sail., Nature Reviews Microbiology., (2013), vol. 11:743.

Vogel., A bacterial seek-and-destroy system for foreign DNA., Science., (2014), pp. 972-973, vol. 344(6187).

Olovnikov et al., Bacterial Argonaute Samples the Transcriptome to Identify Foreign DNA., Molecular Cell., (2013), pp. 594-605, vol. 51(5).

Salomon et al., Single-Molecule Imaging Reveals that Argonaute Reshapes the Binding Properties of Its Nucleic Acid Guides., Cell., (2015), pp. 84-95, vol. 162(1).

Slaymaker et al., Rationally engineered Cas9 nucleases with improved specificity., Science., (2016), pp. 84-88, vol. 351(6268).

Zetsche et al., Cpf1 Is a Single RNA-Guided Endonuclease of a Class 2 CRISPR-Cas System., Cell., pp. 759-771, vol. 163(3), (2015).

Kleinstiver et al., High-fidelity CRISPR-Cas9 nucleases with no detectable genome-wide offtarget effects., Nature. (2016), pp. 490-495, vol. 529.

Burstein et al., New CRISPR-Cas systems from uncultivated microbes., Nature., (2017), pp. 237-241, vol. 542(7640).

Chenna et al., Multiple sequence alignment with the Clustal series of programs., Nucleic Acids Research., (2003), pp. 3497-3500, vol. 31.

Letsinger et al., Cholesteryl-conjugated oligonucleotides: synthesis, properties, and activity as inhibitors of replication of human immunodeficiency virus in cell culture., Proc. Natl. Acad. Sci. USA., (1989), pp. 6553-6556, vol. 86 (17).

Manoharan et al., Cholic acid-oligonucleotide conjugates for antisense applications., Bioorganic & Medicinal Chemistry Letters., (1994), pp. 1053-1060, vol. 4(8).

Manoharan et al., Chemical Modifications to Improve Uptake and Bioavailability of Antisense Oligonucleotides., Ann. NY Acad. Sci., (1992), pp. 306-309, vol. 660(1).

Manoharan et al., Introduction of a lipophilic thioether tether in the minor groove of nucleic acids for antisense applications., Bioorganic & Medicinal Chemistry Letters., (1993), pp. 2765-2770, vol. 3(12).

Oberhauser et al., Effective incorporation of 2'-O-methyl-oligoribonuclectides into liposomes and enhanced cell association through modification with thiocholesterol., Nucleic Acids Research., (1992), pp. 533-538, vol. 20(3).

Kabanov et al., A new class of antivirals: antisense oligonucleotides combined with a hydrophobic substituent effectively inhibit influenza virus reproduction and synthesis of virus-specific proteins in MDCK cells., FEES Letters., (1990), pp. 327-330, vol. 259(2).

Manoharan et al., Lipidic nucleic acids., Tetrahedron Letters., (1995), pp. 3651-3654, vol. 36(21).

Saison-Behmoaras et al., Short modified antisense oligonucleotides directed against Ha-ras point mutation induce selective cleavage of the mRNA and inhibit T24 cells proliferation., EMBO Journal., (1991), pp. 1111-1118, vol. 10(5).

Manoharan et al., Oligonucleotide Conjugates: Alteration of the Pharmacokinetic Properties of Antisense Agents., Nucleosides & Nucleotides., (1995), pp. 969-973, vol. 14(3-5).

Svinarchuk et al., Inhibition of HIV proliferation in MT-4 cells by antisense oligonucleotide conjugated to lipophilic groups., Biochimie., (1993), pp. 49-54, vol. 75(1-2).

Miller et al., Improved Retroviral Vectors for Gene Transfer and Expression., Biotechniques, (1989), pp. 980-990, vol. 7(9).

Shea et al., Synthesis, hybridization properties and antiviral activity of lipid-oligodeoxynucleotide conjugates., Nucleic Acids Research., (1990), pp. 3777-3783, vol. 18(13).

Benoist et al., In vivo sequence requirements of the SV40 early promoter region., Nature., (1981), pp. 304-310, vol. 290.

(56) References Cited

OTHER PUBLICATIONS

Yamamoto et al., Identification of a functional promoter in the long terminal repeat of Rous sarcoma virus., Cell., (1980), pp. 787-797, vol. 22(3).

Wagner et al., Nucleotide sequence of the thymidine kinase gene of herpes simplex virus type 1., Proc. Natl. Acad. Sci. U.S.A., (1981), pp. 1441-1445, vol. 78(3).

Brinster et al., Regulation of metallothionein-thymidine kinase fusion plasmids injected into mouse eggs., Nature., (1982), pp. 39-42, vol. 296.

Villa-Kamaroff et al., A bacterial clone synthesizing proinsulin., Proc. Natl. Acad. Sci. U.S.A., (1978), pp. 3727-3731, vol. 75(8).

Deboer et al., The tac promoter: a functional hybrid derived from the trp and lac promoters . . . , Proc. Natl. Acad. Sci. U.S.A., (1983), pp. 21-25, vol. 80(1).

Swift et al., Tissue-specific expression of the rat pancreatic elastase I gene in transgenic mice., Cell., (1984), pp. 639-646, vol. 38(3).

Ornitz et al., Elastase I Promoter Directs Expression of Human Growth Hormone and SV40 T Antigen Genes to Pancreatic Acinar Cells in Transgenic Mice., Cold Spring Harbor Symposia on Quantitative Biology., pp. 399-409, vol. 50, (Year: 1985).

Macdonald., Expression of the pancreatic elastase I gene in transgenic mice., Hepatology., (1987), pp. 425-515, vol. 7(S1).

Hanahan., Heritable formation of pancreatic β-cell tumours in transgenic mice expressing recombinant insulin/simian virus 40 oncogene., Nature., (1985), pp. 115-122, vol. 315.

Grosschedl et al., Introduction of a u immunoglobulin gene into the mouse germ line: Specific expression in lymphoid cells and synthesis of functional antibody., Cell., (1984), pp. 647-658, vol. 38(3).

Alexander et al., Expression of the c-myc oncogene under control of an immunoglobulin enhancer in E mu-myc transgenic mice., Molecular Cellular Biology., (1987), pp. 1436-1444, vol. 7(4).

Leder et al., Consequences of widespread deregulation of the c-myc gene in transgenic mice: Multiple neoplasms and normal development., Cell., (1986), pp. 485-495, vol. 45.

Pinkert et al., An albumin enhancer located 10 kb upstream functions along with its promoter to direct efficient, liver-specific expression in transgenic mice., Genes and Development., (1987), pp. 268-276, vol. 1.

Krumlauf et al., Developmental regulation of alpha-fetoprotein genes in transgenic mice., Molecular and Cellular Biology., (1985), pp. 1639-1648, vol. 5(7).

Hammer et al., Diversity of Alpha-Fetoprotein Gene Expression in Mice Is Generated by a Combination of Separate Enhancer Elements., Science., (1987), pp. 53-58, vol. 235(4784).

Kelsey et al., Species- and tissue-specific expression of human alpha 1-antitrypsin in transgenic mice., Genes and Development., (1987), pp. 161-171, vol. 1.

Kollias et al., Regulated expression of human Aγ-, β-, and hybrid γβ-globin genes in transgenic mice: Manipulation of the developmental expression patterns., Cell., (1986), pp. 89-94, vol. 46(1).

Readhead et al., Expression of a myelin basic protein gene in transgenic shiverer mice: Correction of the dysmyelinating phenotype., Cell., (1987), pp. 703-712, vol. 48(4).

Mason et al., A Deletion Truncating the Gonadotropin-Releasing Hormone Gene Is Responsible for Hypogonadism in the hpg Mouse., Science., (1986), pp. 1372-1378, vol. 234(4782).

Paulus et al., Self-Contained, Tetracycline-Regulated Retroviral Vector System for Gene Delivery to Mammalian Cells., Journal of Virology., (1996), pp. 62-67, vol. 70(1).

Mannino et al., Liposome mediated gene transfer., BioTechniques., (1988), pp. 682-690, vol. 6(7).

Felgner et al., Cationic liposome-mediated transfection., Nature., (1989), pp. 387-388., vol. 337.

Dull et al., A Third-Generation Lentivirus Vector with a Conditional Packaging System., Journal of Viralogy., (1998), pp. 8463-8471, vol. 72(11).

Choi et al., AAV Hybrid Serotypes: Improved Vectors for Gene Delivery., Current Gene Therapy., (2005), pp. 299-310, vol. 5(3).

Sun et al., Cocoon-Like Self-Degradable DNA Nanoclew for Anti-cancer Drug Delivery., Journal of American Chemical Society., (2014), pp. 14722-14725, vol. 136(42).

Sun et al., Efficient Delivery of CRISPR-Cas9 for Genome Editing via Self-Assembled DNA Nanoclews., Angew. Chem. Int. Ed., (2015), pp. 12029-12033, vol. 54(41).

Lorenceau et al., Generation of Polymerosomes from Double-Emulsions, Langmuir., (2005), pp. 9183-9186, vol. 21 (20).

Jaqaman et al., Robust single-particle tracking in live-cell time-lapse sequences., Nature Methods., (2008), pp. 695-702, vol. 5.

Dahlman et al., Orthogonal gene knockout and activation with a catalytically active Cas9 nuclease., Nature Biotechnology., (2015), pp. 1159-1161, vol. 33.

Singh et al., Real-time observation of DNA recognition and rejection by the RNA-guided endonuclease Cas9., Nature Communications., (2016), vol. 7:12778.

Singh et al., Mechanisms of improved specificity of engineered Cas9s revealed by single-molecule FRET analysis., Nature Structural and Molecular Biology., (2018), pp. 347-354, vol. 25.

Sternberg et al., Conformational control of DNA target cleavage by CRISPR-Cas9., Nature., (2015), pp. 110-113, vol. 527.

Lusic et al., Photochemical DNA activation., Organic Letters., (2007), pp. 1903-1906, vol. 9(10).

Richardson et al., Enhancing homology-directed genome editing by 30 catalytically active and inactive CRISPR-Cas9 using asymmetric donor DNA., Nature Biotechnology., (2016), pp. 339-344, vol. 34.

Newton et al., DNA stretching induces Cas9 off-target activity., Nature Structural and Molecular Biology., (2019), pp. 185-192, vol. 26.

Ma et al., Multiplexed labeling of genomic loci with dCAS9 and engineered sgRNAs using CRISPRainbow. Nat. Biotechnol. 34, 528-530 (2016).

Karanam et al., Quantitative Live Cell Imaging Reveals a Gradual Shift between DNA Repair Mechanisms and a Maximal Use of HR in Mid S Phase., Molecular Cell., (2012), pp. 320-329, vol. 47(2).

Whinn et al., Nuclease dead Cas9 is a programmable roadblock for DNA replication., Scientific Reports., (2019), vol. 9:13292.

Shibata et al., Real-space and real-Time dynamics of CRISPR-Cas9 visualized by high-speed atomic force microscopy., Nature Communications., (2017), vol. 8:1430.

Haapaniemi et al., CRISPR-Cas9 genome editing induces a p53-mediated DNA damage response., Nature Medicine., (2018), pp. 927-930, vol. 24.

Ihry et al., P53 inhibits CRISPR-Cas9 engineering in human pluripotent stem cells., Nature Medicine., (2018), pp. 939-946, vol. 24.

Rogakou et al., Megabase chromatin domains involved in DNA double-strand breaks in vivo., Journal of Cell Biology., (1999), pp. 905-916, vol. 146(5).

Clouaire et al., Comprehensive Mapping of Histone Modifications at DNA Double-Strand Breaks Deciphers Repair Pathway Chromatin Signatures., Molecular Cell., (2018), pp. 250-262, vol. 72(2).

Clouaire et al., A Snapshot on the Cis Chromatin Response to DNA Double-Strand Breaks., Trends in Genetics., (2019), pp. 330-345, vol. 35(5).

(Zhang, X et al.) Genetic editing and interrogation with Cpf1 and caged truncated pre-tRNA-like crRNA in mammalian cells. Cell Discovery. Jul. 10, 2018, vol. 4, No. 36; pp. 1-10; figure is figure legend; DOI: 10.1038/s41421-018-0035-0.

(Liu, Yet al.) Very fast CRISPR on demand. Science. Jun. 12, 2020, vol. 368, No. 6496; pp. 1265-1269; DOI: 10.1126/science.aay8204.

(Zhou, W et al.) Spatiotemporal Control of CRISPR/Cas9 Function in Cells and Zebrafish using Light-Activated Guide RNA. Nov. 13, 2019; bioRxiv 831974; pp. 1-11; DOI: 10.1101/831974.

* cited by examiner

A

B

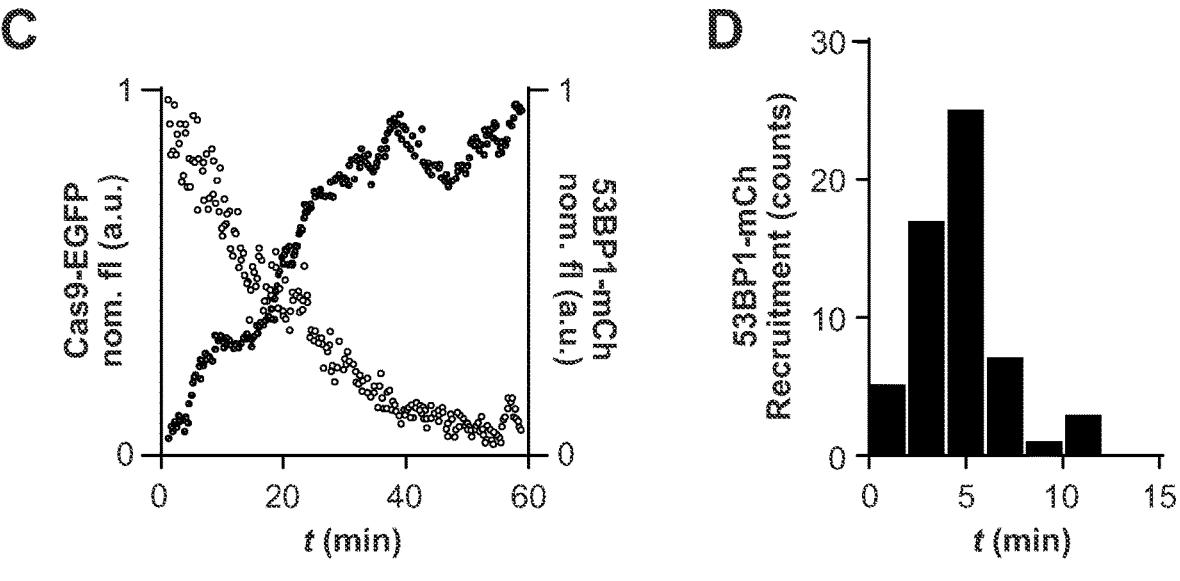
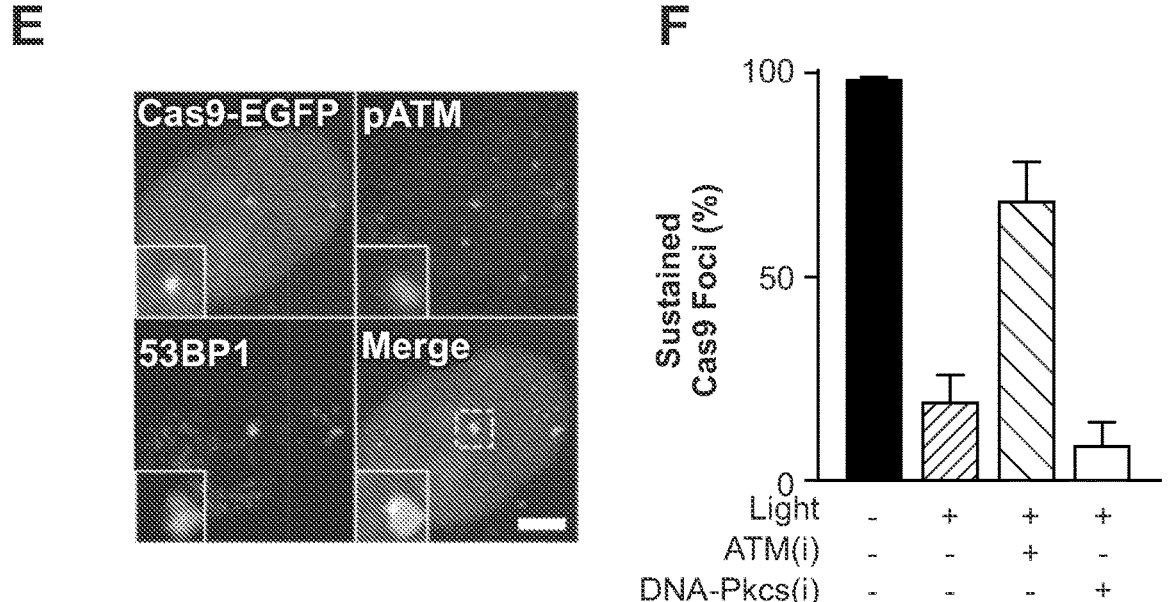
FIGS. 3C-3F

I

J

C

D

A

B

A

B

LIGHT-INDUCIBLE CRISPR/Cas9 SYSTEM FOR GENOME EDITING

RELATED APPLICATIONS

This application is a National Stage Application pursuant to 35 U.S.C. § 371, of United States International Application No. PCT/US20/057256, filed Oct. 25, 2020, which claims priority to, and the benefit under 35 U.S.C. r 35 U.S.C. § 119(e) of U.S. Provisional Application No. 62/926, 412 filed Oct. 25, 2019. The entire contents of which are incorporated herein by reference in their entirety.

STATEMENT REGARDING FE'DERALLY SPONSORED RESEARCH

This invention was made with government support under grant numbers 122569 and 1430124 awarded by the National Institutes of Health and the National Science Foundation. The government has certain rights in this invention.

SEQUENCE LISTING

The instant application contains a Sequence Listing which has been submitted electronically in ASCII format and is hereby incorporated by reference in its entirety. Said ASCII copy, created on Aug. 26, 2025, is named 348358_05901_SL.txt and is 17,378 bytes in size.

FIELD OF THE INVENTION

Caged guide RNAs (gRNAs) regulate the endonuclease activity of gene editing agents.

BACKGROUND

RNA-guided DNA targeting with CRISPR/Cas9 systems has revolutionized biomedical research for genome editing and beyond (M. Jinek, et al. A programmable dual-RNA-guided DNA endonuclease in adaptive bacterial immunity. *Science.* 337, 816-821 (2012); L. Cong, et al. Multiplex genome engineering using CRISPR/Cas systems. *Science.* 339, 819-823 (2013); J. A. Doudna, E. Charpentier, The new frontier of genome engineering with CRISPR-Cas9. *Science.* 346, 1258096 (2014)). After genomic DNA cleavage by Cas9, DNA damage response (DDR) proteins are recruited to initiate repair. DDR requires coordination between multiple factors and competing biochemical processes (S. P. Jackson, J. Bartek, The DNA-damage response in human biology and disease. *Nature.* 461, 1071-1078 (2009); S. E. Polo, S. P. Jackson, Dynamics of DNA damage response proteins at DNA breaks: A focus on protein modifications. *Genes Dev.* 25, 409-433 (2011)). While Cas9-induced DDR is known to be influenced by many factors, including the target sequence (M. W. Shen, et al., Predictable and precise template-free CRISPR editing of pathogenic variants. *Nature.* 563, 646-651 (2018); F. Allen, et al., Predicting the mutations generated by repair of Cas9-induced double-strand breaks. *Nat. Biotechnol.* 37, 64-72 (2019); A. M. Chakrabarti, et al. Target-Specific Precision of CRISPR-Mediated Genome Editing. *Mol. Cell.* 73, 699-713.e6 (2018)), cell cycle (S. Lin, et al. *Elife.* 3, e04766 (2014)), chromatin dynamics (Y. L. Feng, et al. *Nucleic Acids Res.* 45, 10614-10633 (2017); E. M. Kallimasioti-Pazi, et al. Heterochromatin delays CRISPR-Cas9 mutagenesis but does not influence the outcome of mutagenic DNA repair. *PLoS Biol.* 16, e2005595 (2018)) and transcription activity (R. Clarke, et al., Enhanced Bacterial Immunity and Mammalian Genome Editing via RNA-Polymerase-Mediated Dislodging of Cas9 from Double-Strand DNA Breaks. *Mol. Cell.* 71, 42-55.e8 (2018)), the precise timing and sequence of cellular events require further investigation. CRISPR/Cas9 has potential as a convenient tool to study the dynamics of DDR due to its simple programmable function, but currently lack the necessary level of control to initiate precise DNA damage on demand (K. Tsouroula, et al., Temporal and Spatial Uncoupling of DNA Double Strand Break Repair Pathways within Mammalian Heterochromatin. *Mol. Cell.* 63, 293-305 (2016); J. van den Berg, et al. A limited number of double-strand DNA breaks is sufficient to delay cell cycle progression. *Nucleic Acids Res.* 46, 10132-10144 (2018)). To unveil the sequence of Cas9-induced DDR events in living cells, an inducible CRISPR/Cas9 system with the spatiotemporal resolution that matches the rapidity and sub-cellularity of DDR would be powerful.

Numerous inducible CRISPR/Cas9 systems have been developed, including chemically induced Cas9 expression (L. E. Dow, et al. Inducible in vivo genome editing with CRISPR-Cas9. *Nat. Biotechnol.* 33, 390-394 (2015)), translocation (K. I. Liu, et al., A chemical-inducible CRISPR-Cas9 system for rapid control of genome editing. *Nat. Chem. Biol.* 12, 980-987 (2016)), complementation (B. Zetsche, et al. *Nat. Biotechnol.* 33, 139-142 (2015)), photoactivated Cas9 complementation (Y. Nihongaki, et al. *Nat. Biotechnol.* 33, 755-760 (2015)), and uncaging or photolysis of caged unnatural amino acids (J. Hemphill, E. K. Borchardt, K. Brown, A. Asokan, A. Deiters, Optical control of CRISPR/Cas9 gene editing. *J Am. Chem. Soc.* 137, 5642-5645 (2015); P. K. Jain, et al. Development of Light-Activated CRISPR Using Guide RNAs with Photocleavable Protectors. *Angew. Chemie—Int. Ed.* 55, 12440-12444 (2016)). However, these methods often exhibit compromised function in the engineered proteins, coarse temporal control in the hours' time scale, and no spatial control or control at millimeters length scale at best.

SUMMARY

A light-inducible, highly-efficient CRISPR/Cas9 system was produced for genome editing. Accordingly, caged CRISPR RNAs (crRNAs) are provided that allow Cas9 to bind DNA but not cleave until light-induced activation, enabling genomic manipulation at submicron and seconds scales. Synchronized DNA cleavage improved kinetic analysis of double-strand-breaks and their repair, revealing significant re-cutting of mutated DNA. Live cell imaging showed multiple rounds of repair at the same loci, with the first round taking longer than subsequent rounds. The repair times, ranging from 0.5 to 8 h, showed allele-to-allele correlations. Cells detected Cas9-induced breaks and initiated repair within minutes, a process impaired by inhibition of ATM kinase and transcription activity. Imaging-guided subcellular Cas9 activation, achieved genome manipulation at single allele resolution.

In certain embodiments a guide nucleic acid e.g. RNA (gRNA) is provided, wherein the gRNA comprises a sequence having one or more caged nucleotides or analogs thereof. In certain aspects, the one or more caged nucleotides or analogs thereof are photocleavable. In certain aspects, the at least one photocleavable caged nucleotide or analogs thereof are positioned distal to a protospacer adjacent motif (PAM) and target sequence. In certain embodiments, the at least one photocleavable caged nucleotides or analogs thereof, comprise one or more caging groups comprising: 6-nitropiperonyloxymethyl; adenosine-5'-diphosphate, P2-(1-(2-nitrophenyl)-ethyl)-ester, potassium salt; adenosine-5'-triphosphate, P3-(1-(2-nitrophenyl)-ethyl)-ester, sodium salt; adenosine-5'-[(β,γ)-imido]triphosphate, P3-(1-(2-nitrophenyl)-ethyl)-ester, triethylammonium salt; adenosine 5'-triphosphate, P3-(1-(4,5-dimethoxy-2-nitrophenyl)ethyl) ester, disodium salt); adenosine 5'-Triphosphate, P3-(1-(2-nitrophenyl)ethyl) ester, disodium salt; 4,5-dimethoxy-2-nitrophenyl-ethyl (DMNPE); [7-(diethylamino)coumarin-4-yl]methyl (DEACM); or combinations thereof. In certain embodiments, the photocleavable caged nucleotide is 6-nitropiperonyloxymethyl modified deoxynucleotide thymine (NPOM-dT). In certain embodiments, the one or more uracil nucleobases in the nucleic acid sequence of the gRNA are substituted with 6-nitropiperonyloxymethyl modified deoxynucleotide thymine (NPOM-dT).

In certain embodiments, the gRNA is complementary to a target sequence in a genome of a cell. In certain aspects, the target sequence comprises one or more genomic sequences associated with a disease. For example, the disease comprises: tumors, virus infections, autoimmunity diseases, diseases associated with genetic mutations or infectious disease organisms. A guide RNA comprises at least a guide-sequence that is able to hybridize with the target sequence and is able to direct sequence-specific binding of the gene editing complex, for example, CRISPR-Cas system, to the target sequence to form a CRISPR-Cas complex. In order to enable formation of an active CRISPR-Cas complex, the guide-polynucleotide also comprises a sequence that has a specific secondary structure and allows binding of the Cas protein to the guide-polynucleotide. Such sequence is known in the art as tracrRNA, tracr sequence, tracr scaffold or guide-polynucleotide structural component, these terms are used interchangeably herein; wherein the tracr is the abbreviation for transactivating CRISPR; tracrRNA thus means transactivating CRISPR RNA. The tracrRNA in the original CRISPR-Cas system is the endogenous bacterial RNA that links thecrRNA (guide-sequence) to the Cas nuclease, being able to bind any crRNA. A guide-polynucleotide structural component may be comprised of a single polynucleotide molecule or may be comprised of two or more molecules hybridized to each other; such hybridizing components of a guide-polynucleotide structural component may be referred to as a tracr sequence and a tracr-mate sequence.

In certain embodiments, a crRNA sequence comprises one or more photocleavable caged nucleotides or analogs thereof, wherein the one or more photocleavable caged nucleotides or analogs thereof are positioned distal to a protospacer adjacent motif (PAM) and target sequence. In certain embodiments, the at least one photocleavable caged nucleotides or analogs thereof, comprise one or more caging groups comprising: 6-nitropiperonyloxymethyl; adenosine-5'-diphosphate, P2-(1-(2-nitrophenyl)-ethyl)-ester, potassium salt; adenosine-5'-triphosphate, P3-(1-(2-nitrophenyl)-ethyl)-ester, sodium salt; adenosine-5'-[(β,γ)-imido]triphosphate, P3-(1-(2-nitrophenyl)-ethyl)-ester, triethylammonium salt; adenosine 5'-triphosphate, P3-(1-(4,5-dimethoxy-2-nitrophenyl)ethyl) ester, disodium salt); adenosine 5'-Triphosphate, P3-(1-(2-nitrophenyl)ethyl) ester, disodium salt; 4,5-dimethoxy-2-nitrophenyl-ethyl (DMNPE); [7-(diethylamino)coumarin-4-yl]methyl (DEACM); or combinations thereof. In certain aspects, the at least one photocleavable caged nucleotide is 6-nitropiperonyloxymethyl modified deoxynucleotide thymine (NPOM-dT). In certain embodiments, the one or more uracil nucleobases in the nucleic acid sequence of the gRNA are substituted with 6-nitropiperonyloxymethyl modified deoxynucleotide thymine (NPOM-dT).

In certain embodiments, a composition comprises a nucleic acid sequence encoding: a clustered regularly interspaced short palindromic repeats (CRISPR)-associated endonuclease, a Cas peptide and at least one guide RNA, wherein the at least one guide RNA comprises at least one photocleavable caged nucleotide or analogs thereof, wherein the at least one photocleavable caged nucleotide or analogs thereof are positioned distal to a protospacer adjacent motif (PAM) and target sequence. In certain embodiments, the at least one photocleavable caged nucleotides or analogs thereof, comprise one or more caging groups comprising: 6-nitropiperonyloxymethyl; adenosine-5'-diphosphate, P2-(1-(2-nitrophenyl)-ethyl)-ester, potassium salt; adenosine-5'-triphosphate, P3-(1-(2-nitrophenyl)-ethyl)-ester, sodium salt; adenosine-5'-[(β,γ)-imido]triphosphate, P3-(1-(2-nitrophenyl)-ethyl)-ester, triethylammonium salt; adenosine 5'-triphosphate, P3-(1-(4,5-dimethoxy-2-nitrophenyl)ethyl) ester, disodium salt); adenosine 5'-Triphosphate, P3-(1-(2-nitrophenyl)ethyl) ester, disodium salt; 4,5-dimethoxy-2-nitrophenyl-ethyl (DMNPE); [7-(diethylamino)coumarin-4-yl]methyl (DEACM); or combinations thereof. In certain embodiments, the photocleavable caged nucleotide is a 6-nitropiperonyloxymethyl modified deoxynucleotide thymine (NPOM-dT). In certain embodiments, one or more uracil nucleobases in the nucleic acid sequence of the gRNA are substituted with 6-nitropiperonyloxymethyl modified deoxynucleotide thymine (NPOM-dT). In ceratin embodiments, the composition further comprises a sequence encoding a transactivating small RNA (tracrRNA).

In certain embodiments, the composition comprises at least two or more gRNAs. In certain embodiments, the composition comprises one or more nucleic acids sequences encoding multiple guide nucleic acids, wherein each guide nucleic acid comprises a nucleotide sequence substantially complementary to the same target sequences, different target sequences in a host cell genome or a combination thereof.

In certain embodiments, the Cas peptide is Cas9, Cpf1 or variants thereof. In certain embodiments, the Cas9 variant comprises one or more point mutations, relative to wildtype *Streptococcus pyogenes* Cas9 (spCas9), selected from the group consisting of R780A, K810A, K848A, K855A, H982A, K1003A, R1060A, D1135E, N497A, R661A, Q695A, Q926A, L169A, Y450A, M495A, M694A, and M698A. In certain embodiments, the nucleic acid sequence encoding the Cas peptide is optimized for expression in a human cell. In certain embodiments, the gRNA is substantially complementary to a target sequence in a cell.

In certain embodiments, a method of modulating activity of a gene editing complex in a host cell, comprises contacting the host cell with a composition comprising a nucleic acid sequence encoding: a clustered regularly interspaced short palindromic repeats (CRISPR)-associated endonuclease, a Cas peptide and at least one guide RNA (gRNA), wherein the at least one guide RNA comprises at least one photocleavable caged nucleotide or analogs thereof; subjecting the host cell to an electromagnetic radiation, thereby cleaving the at least one photocleavable caged nucleotide or analogs thereof, to modulate the activity of the gene-editing complex. In certain embodiments, the at least one photocleavable caged nucleotide or analogs thereof are positioned in the gRNA sequence, distal to a protospacer adjacent motif (PAM) and target sequence. In certain embodiments, the gRNA is substantially complementary to a target sequence in the genome of a host cell. In embodiments, the guide RNA guides the gene-editing complex to the target sequence wherein the gene editing complex binds to the target sequence in the host cell. The at least one photocleavable caged nucleotide or analogs thereof, sterically hinder hybridization between the PAM distal gRNA and target sequence, inhibits the activity of the gene editing complex. When the complex is subjected to an electromagnetic radiation having a wavelength of between about 190 to about 2400 nm, the electromagnetic radiation cleaves the photocleavable caging groups thereby removing the steric hindrance allowing for the gRNA to hybridize to the host cell target sequence. The gene editing complex is activated following the hybridization of the gRNA to the host cell target sequence. In certain embodiments, the at least one photocleavable caged nucleotides or analogs thereof, comprise one or more caging groups comprising: 6-nitropiperonyloxymethyl; adenosine-5'-diphosphate, P2-(1-(2-nitrophenyl)-ethyl)-ester, potassium salt; adenosine-5'-triphosphate, P3-(1-(2-nitrophenyl)-ethyl)-ester, sodium salt; adenosine-5'-[(β,γ)-imido]triphosphate, P3-(1-(2-nitrophenyl)-ethyl)-ester, triethylammonium salt; adenosine 5'-triphosphate, P3-(1-(4,5-dimethoxy-2-nitrophenyl)ethyl) ester, disodium salt); adenosine 5'-Triphosphate, P3-(1-(2-nitrophenyl)ethyl) ester, disodium salt; 4,5-dimethoxy-2-nitrophenyl-ethyl (DMNPE); [7-(diethylamino)coumarin-4-yl]methyl (DEACM); or combinations thereof. In certain embodiments, the photocleavable caged nucleotide is a 6-nitropiperonyloxymethyl modified deoxynucleotide thymine (NPOM-dT). In certain embodiments, one or more uracil nucleobases in the nucleic acid sequence of the gRNA are substituted with 6-nitropiperonyloxymethyl modified deoxynucleotide thymine (NPOM-dT). In certain embodiments, the composition comprises a sequence encoding a transactivating small RNA (tracrRNA). In certain embodiments, the composition comprises at least two or more gRNAs. In certain embodiments, the composition comprises one or more nucleic acids sequences encoding multiple guide nucleic acids, wherein each guide nucleic acid comprises a nucleotide sequence substantially complementary to the same target sequences in a host cell genome, to different target sequences in a host cell genome or a combination thereof. In certain embodiments, the Cas peptide is Cas9, Cpf1 or variants thereof. In certain embodiments, the Cas9 variant comprises one or more point mutations, relative to wildtype *Streptococcus pyogenes* Cas9 (spCas9), selected from the group consisting of R780A, K810A, K848A, K855A, H982A, K1003A, R1060A, D1135E, N497A, R661A, Q695A, Q926A, L169A, Y450A, M495A, M694A, and M698A. In certain embodiments, the nucleic acid sequence encoding the Cas peptide is optimized for expression in a human cell.

In certain embodiments, a method of sequential activation of a gene-editing complex in a host cell comprises contacting the host cell with a composition comprising two or more nucleic acid sequence encoding: a clustered regularly interspaced short palindromic repeats (CRISPR)-associated endonuclease, a Cas peptide and at least one guide RNA (gRNA) each, wherein the at least one guide RNA of each of the nucleic sequences comprise at least one photocleavable caged nucleotide or analogs thereof, subjecting the host cell to varying wavelengths of electromagnetic radiation over intervals of time, thereby cleaving the at least one photocleavable caged nucleotide or analogs thereof, and, sequentially modulating activity of the gene-editing complex over time per target sequence. In certain embodiments, the photocleavable caged nucleotides comprise photocleav-able caging groups susceptible to cleavage by electromagnetic radiation of different wavelengths. Each gRNA is substantially complementary to a target sequence in the host cell, wherein each gRNA specific for the similar or substantially similar target sequences comprise photocleavable caged nucleotides comprising photocleavable caging groups cleavable by the same wavelength of electromagnetic radiation.

In certain embodiments, an expression vector encoding a clustered regularly interspaced short palindromic repeats (CRISPR)-associated endonuclease, a Cas peptide and at least one guide RNA, wherein the at least one guide RNA comprises at least one photocleavable caged nucleotide or analogs thereof.

In certain embodiments, a kit comprises the guide RNAs (gRNA) embodied herein, a CRISPR RNA (crRNA) embodied herein, a composition embodied herein, an expression vector embodied herein or combinations thereof.

In certain embodiments, a nucleic acid sequence comprises a sequence having at least about 70% (such as at least about 75%, 80%, 85%, 90%, 91%, 92%, 93%, 94%, 95%, 96%, 97%, 98%, 99%, or greater) sequence identity to any one of SEQ ID NOS: 1-61.

In certain embodiments, a nucleic acid sequence comprises any one or more of SEQ ID NOS: 1 to 61.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. It is also to be understood that the terminology used herein is for the purpose of describing particular embodiments only, and is not intended to be limiting. In describing and claiming the present invention, the following terminology will be used.

All genes, gene names, and gene products disclosed herein are intended to correspond to homologs from any species for which the compositions and methods disclosed herein are applicable. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, are intended to encompass homologous and/or orthologous genes and gene products from other species.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type. Furthermore, to the extent that the terms "including", "includes", "having", "has", "with", or variants thereof are used in either the detailed description and/or the claims, such terms are intended to be inclusive in a manner similar to the term "comprising."

"About" as used herein when referring to a measurable value such as an amount, a temporal duration, and the like, is meant to encompass variations of +/−20%, +/−10%, +/−5%, +/−1%, or +/−0.1% from the specified value, as such variations are appropriate to perform the disclosed methods. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "caged nucleotides" refers to a nucleotide having a group that substantially hinders the function or endonuclease activity of the gene-editing complex by creating artificial mismatches as a "roadblock". The caging group may be removed e.g., by exposure to light in a "photocleavable caged" nucleotide to restore activity of the gene editing complex.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

As used herein, the term "expression" as used herein is defined as the transcription and/or translation of a particular nucleotide sequence driven by its promoter.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, the term "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purifed from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes: a recombinant DNA which is part of a hybrid gene encoding additional polypeptide sequence, complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties. In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

As used herein, the terms "nucleic acid sequence", "polynucleotide," are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the term "nucleotide" refers to a monomeric unit of DNA or RNA containing (a) a purine (e.g., adenine, guanine) or pyrimidine (e.g., cytosine, thymine, uracil) base, (b) a pentose (2-deoxy-D-ribose in deoxyribo-nucleotides and D-ribose in ribonucleotides), and (c) a molecule of phosphoric acid. The pentose is joined to the base by a β-N-glycosyl bond between carbon atom 1 of the pentose and nitrogen atom 9 of purine bases or nitrogen atom 1 of pyrimidine bases. The phosphate group of nucleotides is in ester linkage with carbon atom 5 of the pentose. See, e.g., A. Leninger, *Biochemistry,* 309-312 (2d Ed. 1975).

As used herein, the term "nucleotide analog" includes nucleotides in which the ribose or deoxyribose ring is altered, substituted or replaced, and/or w here the phosphodiester bonds are altered, substituted or replaced (e.g., with a phosphorothioate group, a phosphoramidate group or the like. Examples include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylamino-ethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA) modified, a locked nucleic acid (LNA), an ethylene nucleic acid (ENA), a peptide nucleic acid (PNA), a 1',5'-anhydro-hexitol nucleic acid (HNA), a morpholino, a methylphosphonate nucleotide, a thiolphosphonate nucleotide, a 2'-fluoro N3-P5'-phosphoramidite and the like.

In certain embodiments, a nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. It is further preferred that the linkage between a residue in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

In certain embodiments, a nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al. (1993) *Nature* 365, 566-568).

In certain embodiments, a backbone comprises a morpholino nucleotide analog or equivalent, in which the ribose or deoxyribose sugar is replaced by a 6-membered morpholino ring. A nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In certain embodiments, a nucleotide analogue or equivalent comprises a substitution of at least one of the non-bridging oxygen molecules in the phosphodiester linkage. This modification slightly destabilizes base-pairing but adds significant resistance to nuclease degradation. A nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, seleno-phosphate or boranophosphate. A further nucleotide analogue or equivalent comprises one or more sugar moieties that are mono- or disubstituted at the 2', 3' and/or 5' position such as a —OH; —F; substituted or unsubstituted, linear or branched lower (C1-010) alkyl, alkenyl, alkynyl, alkaryl, allyl, aryl, or aralkyl, that may be interrupted by one or more heteroatoms; O—, S—, or N-alkyl; O—, S—, or N-alkenyl; O-, S- or N-alkynyl; O—, S—, or N-allyl; O-alkyl-O-alkyl, -methoxy, -aminopropoxy; aminoxy, methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or deoxyribose or derivative thereof. Such derivatized sugar moieties comprise Locked Nucleic Acid (LNA), in which the 2'-carbon atom is linked to the 3' or 4' carbon atom of the sugar ring thereby forming a bicyclic sugar moiety. In certain embodiments, an LNA comprises 2'-0,4'-C-ethylene-bridged nucleic acid (Morita et al. 2001. *Nucleic Acid Res* Supplement No. 1: 241-242). These substitutions render the nucleotide analogue or equivalent RNase H and nuclease resistant and increase the affinity for the target.

As used herein, the term "oligonucleotide" refers to two more nucleotides linked by phosphodiester bridges formed between the 5'-hydroxyl group of one nucleotide and the 3'-hydroxyl group of the next adjacent nucleotide. A, Leninger, supra at 318. Oligonucleotides may be provided single stranded, double stranded with a complementary antiparallel oligonucleotide or oligonucleotide analog by Watson-Crick pairing (where the complementary strand may or may not contain a caged nucleotide or nucleotide analog), triplex or quadruplex stranded (e.g., as described in U.S. Pat. No. 6,656,692), etc. Oligonucleotides may be polymers of the same, or different, nucleotides, e.g., "gapamers".

As used herein, the term "oligonucleotide analog" refers to two or more nucleotide or nucleotide analogs (where at least one is a nucleotide analog), linked by phosphodiester bonds or other bond (such as a peptide bond for a peptide nucleic acid) Oligonucleotide analogs may be provided single stranded, double stranded with a complementary antiparallel oligonucleotide or oligonucleotide analog by Watson-Crick parring (where the complementary strand may or may not contain a caged nucleotide or nucleotide analog), triplex or quadruplex stranded (e.g., as described in U.S. Pat. No. 6,656,692), etc. Oligonucleotide analogs may be polymers of the same, or different, nucleotide analogs or nucleotides, e.g., "gapamers".

The terms "pharmaceutically acceptable" (or "pharmacologically acceptable") refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "protecting group" includes any suitable protecting group; "protected form" refers to a substituent in which an atom such as hydrogen has been removed and replaced with a corresponding protecting group. Protecting groups are known. See generally T. H. Greene and P. G. M. Wuts, Protective Groups in Organic Synthesis, 3rd edition, John Wiley & Sons, New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, di phenyl methoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, acetyl (Ac or $—C(O)CH_3$), benzoyl (Bn or $—C(O)C_6H_5$), and trimethylsilyl (TMS or $—Si(CH_3)_3$), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like. See, e.g., U.S. Pat. Nos. 6,953,782; 6,951,946; 6,951,942; and 6,051,724.

As used herein, "sequence identity" or "identity" in the context of the present invention of an amino acid- or nucleic acid-sequence is herein defined as a relationship between two or more amino acid (peptide, polypeptide, or protein) sequences or two or more nucleic acid (nucleotide, oligonucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence means sequence identity over the entire length of said particular polypeptide or polynucleotide sequence. Percent complementarity of guide nucleic acid with a region of a target nucleic acid can be determined routinely using BLAST programs (basic local alignment search tools) and PowerBLAST programs known in the art. Percent homology, percent sequence identity or complementarity, can be determined by, for example, the Gap program.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any nucleotide or amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

BRIEF DESCRIPTION OF THE DRAWINGS

FIG. 1B is blot of results from an electrophoretic mobility shift assay (EMSA) showing that Cas9/cgRNA binds to target DNA without cleavage. FIGS. 1C, 1D is a blot form an in vitro cleavage assay showing the fast kinetics of Cas9 activity within seconds after light activation. DNA cleavage efficiency is shown as activation percentage (Act. %).

FIG. 2A is a schematic of the experimental and analysis pipeline. High-throughput Illumina sequencing and Sanger sequencing-based TIDE analysis were used for indel quantification. In DSB-ddPCR, FAM labeled qPCR probe (green) targets a region that includes the target double strand breaks (DSBs) (red triangle), while the internal reference HEX labeled probe targets a nearby un-cleaved region. FIG. 2B is a plot of indels detected by high-throughput sequencing of PCR-amplified genomic DNA from cells without RNP, with RNP but no light, and with RNP 48 h after light activation. FIG. 2C is a graph showing the percentage of DSBs detected by DSB-ddPCR of genomic DNA from cells without RNP, with RNP but no light, and with RNP 30 s after light activation. FIG. 2D are graphs showing the paired modeling of DSBs and normalized indels for the ACTB locus. Here, Normalized Indel % is defined the Indel % from all DNA at a particular locus, not just from PCR-amplifiable DNA; Norm. Indel %=Indel %×(100−DSB %)/100. The sum of DSB %, Normalized Indel % and Intact % equals 100%. FIG. 2E is a graph showing results from an in vitro assay comparing the cleavage efficiencies of wild-type ACTB target and ACTB target with indel-containing +1 'A' insertion.

FIGS. 3A-3H are a series of schematics, graphs plots and images and demonstrating the single-allele imaging and manipulation of Cas9 activation in living cells. FIG. 3A is a schematic of Cas9-EGFP binding to ~200 binding sites and cleaving target DNA in response to light stimulation. FIG. 3B demonstrates the light induced DNA damage and repair at the Cas9 foci (green) shown by 53BP1-mCherry recruitment (red). Zoomed inset of dotted white box showing the dynamics of Cas9 and 53BP1 foci as a function of time. Scale bar, 5 µm. FIG. 3C is a plot showing the maximum projected intensity traces of Cas9 and 53BP1 foci as a function of time for the zoomed single locus shown in (FIG. 3B). FIG. 3D: Histogram of 53BP1 recruitment time at the Cas9 foci. FIG. 3E is a series of immunofluorescence images showing that endogenous phosphorylated ATM kinase and 53BP1 colocalized at the Cas9 binding and cleavage site at t=5 min. FIG. 3F is a bar graph comparing the loss of Cas9 foci with/without ATM and DNA-PKc inhibition (error bar represents standard error, n=3, n>100 cells for each conditions). FIG. 3G is a series of representative images of allele specific Cas9 activation at the repetitive region. Magenta square highlights the allele stimulated with 405 nm light. FIG. 3H is a pie chart showing the quantification of Cas9 activation at the stimulated Ch3rep allele as measured by 53BP1-mCherry recruitment. Single allele specificity is defined as the fraction of cells that showed DDR at the single illuminated allele over the sum of cells that demonstrated damage in either single allele or both alleles.

FIG. 4A is a schematic of orthogonal genomic imaging and cleavage using Cas9-EGFP. FIG. 4B is a series of representative images from time-lapse movie showing 53BP1 recruitment at single Cas9 cleavage site. Two PPP1R2 loci were marked by magenta square and cyan circle. Zoom-in images showing multiple cycles of DNA repair occurred at one PPP1R2 locus (magenta square). FIG. 4C shows the fluorescence intensity traces of 53BP1-mCh for both alleles monitored in (FIG. 4B). The start, end and dwell time of the first cycle of DNA repair are marked as $T_1$, $t_1$ and $D_1$. The time interval $T_g$ is calculated as $T_{n+1}-t_n$, for example, $T_2-t_1$. FIG. 4D is a graph of the quantification of 53BP1 recruitment for non-treated and cells treated with ATM, and transcription inhibitors. (Error bars represent standard error, n=2, n>50 cells for each conditions). FIG. 4E is a histogram of initial 53BP1 recruitment time ($T_1$) at the PPP1R2 locus after light stimulation. FIG. 4F is a rastergram of 53BP1 foci at 124 paired alleles in 62 cells. Each row displays time courses of 53BP1 foci at a pair of alleles residing in the same nucleus (randomized allele1 and allele2). Grey dot indicates presence and white indicates absence of 53BP1-mCh at the PPP1R2 locus. Cells are ranked by the mean dwell time of the first 53BP1 recruitment at two alleles (longest to shortest). FIG. 4G is a histogram of time interval ($T_g$) between consecutive 53BP1 cycles for 8 h. FIG. 4H is a plot showing the dwell time of 53BP1 foci at the PPP1R2 locus at different repair cycles and DRB treated cells (n=168 alleles). Unpaired t-test was performed, **P<0.0001. FIG. 4I is a scatter plot showing positive correlation of dwell time between two alleles in the same cell nucleus (r=0.45). FIG. 4J** is a pie chart showing the percentage quantification of Cas9 specificity at the stimulated PPP1R2 allele as measured by 53BP1-mCherry recruitment.

FIG. 5A shows results from an in vitro cleavage assay showing dosage-dependent DNA cleavage activity. Samples were incubated at 37° C. for 30 min after light stimulation of indicated duration (dosage). FIG. 5B is a plot showing the quantification of Cas9 cleavage activity measured in FIG. 5A. Gel quantification of cleavage percentage was performed using the ImageJ gel analysis function.

FIG. 6A: HEK 293 cells were harvested two days later and flow cytometry was used to count the cells (n=3 biological triplicates). FIG. 6B: Immunofluorescence microscopy was performed to assess the number of phosphorylated H2Ax foci in U-2 OS without light stimulation and after 30 s 365 nm light stimulation. Cells were fixed at 1, 3 and 8 h after stimulation for the assay (n>100 cells for 5 technical replicates, foci number normalized to no light control). Error bars represent standard error of the mean in both plots.

FIG. 7A: Standard curves demonstrate the linear relationship between the expected DSB frequency and the DSB frequency measured by the DSB-ddPCR assay at the ACTB, IFT88, MYC. Regression was computed using data from technical duplicates. FIG. 7B: Representative droplet FAM and HEX probe intensities for cells without electroporation of RNPs (left panel), with RNP but no light stimulation (middle panel), and with RNPs and 30 sec post light stimulation (right panel). Grey points indicate droplets with either no DNA templates or no probes (bottom left), or with just reference probe (FAM) (top left), and are not considered in the analysis. Colored points indicate droplets with intact/indel genomic DNA with both FAM and HEX probes (top right), or droplets with DSB-containing genomic DNA and/or with only HEK probe (bottom right). Red color represents high population of the species.

FIG. 8A is a graph demonstrating that targeted deep sequencing revealed significant percentage of indels are +1 insertions or −1 deletions at three loci 48 h after Cas9 activation. WT represents the percentage of DNA with no mutation. FIG. 8B is a sequence depicting that at the ACTB locus, 97.3±1.3% of +/−1 indels are +1 'A' insertions. Sequence logo for +1 insertion reads demonstrate +A to be the predominant species. Sequence logos were generated using WebLogo (Crooks G E et al., WebLogo: A sequence logo generator, Genome Research, 14:1188-1190, (2004); Schneider T D, Stephens R M. 1990. Sequence Logos: A New Way to Display Consensus Sequences. *Nucleic Acids Res.* 18:6097-6100). Figure discloses SEQ ID NOS 63 and 64, respectively, in order of appearance. FIGS. 8C, 8D: Cleavage of +1/−1 indels and WT sequences at MYC and ACTB loci in a representative gel (FIG. 8C) and its quantification (n=2 biological replicates) (FIG. 8D). In the plot labels, 'ACTB+1' indicates one A insertion at the cut site, 'MYC+1' indicates C insertion at the cut site, and 'MYC−1' indicates one G deletion 5' of the cut site. All target sequences used in this assay were purchased as dsDNA fragments from GenScript. Error bars represent standard deviations.

FIG. 9B: Fitting data with Model II. FIG. 9C: Plot of sum of squared errors of prediction (SSE) for Models I and II. Lower values indicate better fitting. FIG. 9D:) Plot of model parameters determined from fitting. 's' indicates $k_s$, 'm' indicates $k_m$, etc.; 'B0' is the initial cleavage percent determined experimentally; 'deg' indicates $k_{deg}$ (Example 2). Error bars indicate 95% confidence intervals.

FIG. 11A is a series of representative images showing Cas9-EGFP foci and 53BP1-mCherry in a U-2 OS cell after 30 s of light stimulation. The cell sample was treated with 100 M of ATM kinase inhibitor KU-0055993 for 1 h prior to Cas9 activation. FIG. 11B is a plot showing quantification of 53BP1-mCherry recruitment at the Cas9 foci within 1 h of experimental time. n=66 and 81 cells were analyzed for KU-0055993 non-treated and treated samples, respectively. Error bars represent 95% confidence interval.

FIG. 12A: Laser micro-irradiation (405 nm, 50% power) was used to generate DNA damage in Hoechst 33342 dye (10 µM) sensitized cell nucleus. When no inhibition treatment was applied, phosphorylated DNA-PKcs (52056) was detected globally in the nucleus and enriched at the DNA damage site (top row). In contrast, when DNA-PKcs activity was inhibited with 2.5 µM of Ku-0060648 for 1 h, phosphorylation of DNA-PKcs was completely abolished (bottom row). This experiment demonstrated the functionality of DNA-PKcs inhibitor used. FIG. 12B: Immunofluorescence microscopy showing no phosphorylated DNA-PKcs recruitment at the Cas9 foci with or without uncaging light. FIG. 12C: Plot showing the time for initial 53BP1 recruitment at the Cas9 foci when DNA-PKcs activity was inhibited compared to no treatment control (n=50 cells). Error bars represent standard deviations.

DETAILED DESCRIPTION

RNA guided programmable DNA targeting of CRISPR-Cas9 systems has revolutionized biomedical research for genome editing and beyond. Spatial and temporal control of Cas9 activity enables gene editing or regulation confined to specific space and time. Previous methods, suffer from slow kinetics of induction or compromised function of the engineered Cas9 protein. Furthermore, all these methods require accumulation of active nuclear Cas9 after induction, which then search and bind to the target, rendering it slow for many applications. Here, a very fast CRISPR/Cas9 system is provided whereby Cas9 binds to the target DNA but does not cut until light triggers its activation, leading to cleavage of target DNA within seconds.

Figure 1A:
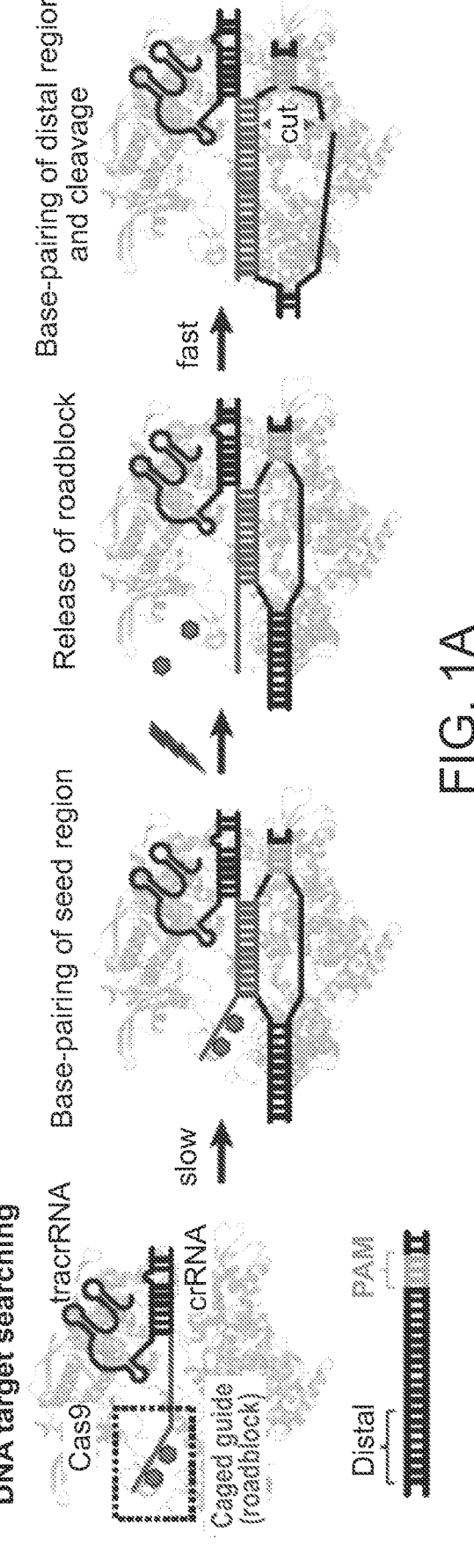
FIGS. 1A-1D are a schematic representation, a series of blots and a graph showing the optical triggering of Cas9 cleavage activity through conformational control. FIG. TA is a schematic showing the light activation of Cas9 by modulating the base-pairing of the distal region of gRNA.

In the design of the gene-editing complexes, light-sensitive caged nucleotides were strategically placed at the PAM-distal region of the guide RNA ($gRNA^{caged}$) to create artificial mismatches as a "roadblock" (FIG. 1A). It was reasoned that the Cas9/$gRNA^{caged}$ complex can search and bind the target DNA in cells, but the bulky caging group sterically block hybridization between the PAM-distal gRNA region and target DNA, thus inhibiting Cas9 cleavage activity. Upon light stimulation at 365 or 405 nm, the caging group ("roadblock") is removed and the gRNA fully hybridizes with the target DNA. Thus, the pre-bound inactive Cas9/$gRNA^{caged}$ is rapidly converted to active Cas9.

Accordingly, in general embodiments, compositions comprise an endonuclease and at least one guide RNA (gRNA) sequence, the guide RNA being complementary to a target nucleic acid sequence in a target gene. In some embodiments, the compositions disclosed herein include nucleic acids encoding an endonuclease, such as Cas9.

Gene Editing Agents: Compositions of the invention include at least one gene editing agent, comprising CRISPR-associated nucleases such as Cas9 and Cpf1 gRNAs, Argonaute family of endonucleases, clustered regularly interspaced short palindromic repeat (CRISPR) nucleases, zinc-finger nucleases (ZFNs), transcription activator-like effector nucleases (TALENs), meganucleases, other endo- or exo-nucleases, or combinations thereof. See Schiffer, 2012, J Virol 88(17):8920-8936, incorporated by reference.

In certain embodiments, the compositions include isolated nucleic acid sequences encoding a Cpf1 (CRISPR from Prevotella and Francisella 1) endonuclease, and at least one guide RNA (gRNA), which is complementary to a target DNA sequence in the target gene. The gRNA directs the Cpf1 endonuclease to the target DNA sequence. The resulting double stranded breaks in the DNA inactivate the target gene by causing point mutations, insertions, deletions, or the complete excision of a stretch of DNA including the target gene.

In other embodiments, nuclease systems that can be used include, without limitation, zinc finger nucleases, transcription activator-like effector nucleases (TALENs), meganucleases, or any other system that can be used to degrade or interfere with viral nucleic acid without interfering with the regular function of the host's genetic material.

As referenced above, Argonaute is another potential gene editing system. Argonautes are a family of endonucleases that use 5' phosphorylated short single-stranded nucleic acids as guides to cleave targets (Swarts, D. C. et al. The evolutionary journey of Argonaute proteins. *Nat. Struct. Mol. Biol.* 21, 743-753 (2014)). Similar to Cas9, Argonautes have key roles in gene expression repression and defense against foreign nucleic acids (Swarts, D. C. et al. *Nat. Struct. Mol. Biol.* 21, 743-753 (2014); Makarova, K. S., et al. *Biol. Direct* 4, 29 (2009). Molloy, S. Nat. Rev. Microbiol. 11, 743 (2013); Vogel, J. *Science* 344, 972-973 (2014). Swarts, D. C. et al. *Nature* 507, 258-261 (2014); Olovnikov, I., et al. *Mol. Cell* 51, 594-605 (2013)). However, Argonautes differ from Cas9 in many ways Swarts, D. C. et al. The evolutionary journey of Argonaute proteins. *Nat. Struct. Mol. Biol.* 21, 743-753 (2014)). Cas9 only exist in prokaryotes, whereas Argonautes are preserved through evolution and exist in virtually all organisms; although most Argonautes associate with single-stranded (ss)RNAs and have a central role in RNA silencing, some Argonautes bind ssDNAs and cleave target DNAs (Swarts, D. C. et al. *Nature* 507, 258-261 (2014); Swarts, D. C. et al. *Nucleic Acids Res.* 43, 5120-5129 (2015)). guide RNAs must have a 3' RNA-RNA hybridization structure for correct Cas9 binding, whereas no specific consensus secondary structure of guides is required for Argonaute binding; whereas Cas9 can only cleave a target upstream of a PAM, there is no specific sequence on targets required for Argonaute. Once Argonaute and guides bind, they affect the physicochemical characteristics of each other and work as a whole with kinetic properties more typical of nucleic-acid-binding proteins (Salomon, W. E., et al. *Cell* 162, 84-95 (2015)).

CRISPR-Associated Endonucleases: The compositions disclosed herein may include nucleic acids encoding a CRISPR-associated endonuclease, such as Cas9. In bacteria, the CRISPR/Cas loci encode RNA-guided adaptive immune systems against mobile genetic elements (viruses, transposable elements and conjugative plasmids). Three types (I-III) of CRISPR systems have been identified. CRISPR clusters contain spacers, the sequences complementary to antecedent mobile elements. CRISPR clusters are transcribed and processed into mature CRISPR RNA (crRNA). The CRISPR-associated endonuclease, Cas9, belongs to the type II CRISPR/Cas system and has strong endonuclease activity to cut target DNA. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM).

In certain embodiments, the Cas9 is a high-fidelity variant comprising SpCas9-HF, eSpCas9, or HypaCas9. These variants display very low off-target activity due to rationally designed mutations.

In certain embodiments, a composition comprises an engineered nucleic acid sequence encoding: a clustered regularly interspaced short palindromic repeats (CRISPR)-associated endonuclease, a Cas peptide and at least one guide RNA comprising at least one photocleavable caged nucleotide or analogs thereof. In certain embodiments, the at least one photocleavable caged nucleotide or analogs thereof are positioned distal to a protospacer adjacent motif (PAM) and target sequence. In certain embodiments, the engineered nucleic acid sequence further comprises a sequence encoding a transactivating small RNA (tracrRNA). In certain embodiments, the composition comprises at least two or more gRNAs.

In certain embodiments, the composition comprises at least two or more gRNAs. In certain embodiments, the composition comprises one or more nucleic acids sequences encoding multiple guide nucleic acids, wherein each guide nucleic acid comprises a nucleotide sequence substantially complementary to the same target sequences, different target sequences in a host cell genome or a combination thereof.

The CRISPR-Cas system includes a gene editing complex comprising a CRISPR-associated nuclease, e.g., Cas9, and a guide RNA complementary to a target sequence situated on a DNA strand, such as a target sequence in a tumor or virus infected cell. The gene editing complex can cleave the DNA within the target sequence. The size of the deletion can vary from a single nucleotide base pair to about 10,000 base pairs. In some embodiments, the deletion can include all or substantially all of the target sequence(s) which contain the mutations. The mutation can comprise an insertion, that is, the addition of one or more nucleotide base pairs to the target sequence. The size of the inserted sequence also may vary, for example from about one base pair to about 300 nucleotide base pairs. The mutation can comprise a point mutation, that is, the replacement of a single nucleotide with another nucleotide. Useful point mutations are those that have functional consequences, for example, mutations that result in the conversion of an amino acid codon into a termination codon or that result in the production of a nonfunctional protein.

In embodiments, the CRISPR/Cas system can be a type I, a type II, or a type III system. Non-limiting examples of suitable CRISPR/Cas proteins include Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

The Cas9 can be an orthologous molecule. Six smaller Cas9 orthologues have been used and reports have shown that Cas9 from *Staphylococcus aureus* (SaCas9) can edit the genome with efficiencies similar to those of SpCas9, while being more than 1 kilobase shorter.

In addition to the wild type and variant Cas9 endonucleases described, embodiments of the invention also encompass CRISPR systems including newly developed "enhanced-specificity" *S. pyogenes* Cas9 variants (eSpCas9), which dramatically reduce off target cleavage. These variants are engineered with alanine substitutions to neutralize positively charged sites in a groove that interacts with the non-target strand of DNA. This aim of this modification is to reduce interaction of Cas9 with the non-target strand, thereby encouraging re-hybridization between target and non-target strands. The effect of this modification is a requirement for more stringent Watson-Crick pairing between the gRNA and the target DNA strand, which limits off-target cleavage (Slaymaker, I. M. et al. (2015) DOI: 10.1126/science.aad5227).

In certain embodiments, three variants found to have the best cleavage efficiency and fewest off-target effects: SpCas9 (K855A), SpCas9 (K810A/K1003A/R1060A) (a.k.a. eSpCas9 1.0), and SpCas9(K848A/K1003A/R1060A) (a.k.a. eSPCas9 1.1) are employed in the compositions. The invention is by no means limited to these variants, and also encompasses all Cas9 variants (Slaymaker, I. M. et al. *Science*. 2016 Jan. 1; 351(6268):84-8. doi: 10.1126/science.aad5227. Epub 2015 Dec. 1). The present invention also includes another type of enhanced specificity Cas9 variant, "high fidelity" spCas9 variants (HF-Cas9). Examples of high fidelity variants include SpCas9-HF1 (N497A/R661A/Q695A/Q926A), SpCas9-HF2 (N497A/R661A/Q695A/Q926A/D1135E), SpCas9-HF3 (N497A/R661A/Q695A/Q926A/L169A), SpCas9-HF4 (N497A/R661A/Q695A/Q926A/Y450A). Also included are all SpCas9 variants bearing all possible single, double, triple and quadruple combinations of N497A, R661A, Q695A, Q926A or any other substitutions (Kleinstiver, B. P. et al., 2016, *Nature*. DOI: 10.1038/nature16526).

As used herein, the term "Cas" is meant to include all Cas molecules comprising variants, mutants, orthologues, high-fidelity variants and the like.

In one embodiment, the endonuclease is derived from a type II CRISPR/Cas system. In other embodiments, the endonuclease is derived from a Cas9 protein and includes Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, mutants, variants, high-fidelity variants, orthologs, analogs, fragments, or combinations thereof. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicellulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.* Included are Cas9 proteins encoded in genomes of the nanoarchaea ARMAN-1 (*Candidatus* Micrarchaeum acidiphilum ARMAN-1) and ARMAN-4 (*Candidatus* Parvarchaeum acidiphilum ARMAN-4), CasY (Kerfeldbacteria, Vogelbacteria, Komeilibacteria, Katanobacteria), CasX (Planctomycetes, Deltaproteobacteria).

In general, CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNAse domains, protein-protein interaction domains, dimerization domains, as well as other domains. Active DNA-targeting CRISPR-Cas systems use 2 to 4 nucleotide protospacer-adjacent motifs (PAMs) located next to target sequences for self- versus non-self-discrimination. ARMAN-1 has a strong 'NGG' PAM preference. Cas9 also employs two separate transcripts, CRISPR RNA (crRNA) and transactivating CRISPR RNA (tracrRNA), for RNA-guided DNA cleavage. Putative tracrRNA was identified in the vicinity of both ARMAN-1 and ARMAN-4 CRISPR-Cas9 systems (Burstein, D. et al. New CRISPR-Cas systems from uncultivated microbes. *Nature*. 2017 Feb. 9; 542(7640):237-241. doi: 10.1038/nature21059. Epub 2016 Dec. 22).

Embodiments of the invention also include a new type of class 2 CRISPR-Cas system found in the genomes of two bacteria recovered from groundwater and sediment samples. This system includes Cas1, Cas2, Cas4 and an approximately ~980 amino acid protein that is referred to as CasX. The high conservation (68% protein sequence identity) of this protein in two organisms belonging to different phyla, Deltaproteobacteria and Planctomycetes, suggests a recent cross-phyla transfer. The CRISPR arrays associated with each CasX has highly similar repeats (86% identity) of 37 nucleotides (nt), spacers of 33-34 nt, and a putative tracrRNA between the Cas operon and the CRISPR array. Distant homology detection and protein modeling identified a RuvC domain near the CasX C-terminal end, with organization reminiscent of that found in type V CRISPR-Cas systems. The rest of the CasX protein (630 N-terminal amino acids) showed no detectable similarity to any known protein, suggesting this is a novel class 2 effector. The combination of tracrRNA and separate Cas1, Cas2 and Cas4 proteins is unique among type V systems, and phylogenetic analyses indicate that the Cas1 from the CRISPR-CasX system is distant from those of any other known type V. Further, CasX is considerably smaller than any known type V proteins: 980 aa compared to a typical size of about 1,200 amino acids for Cpf1, C2c1 and C2c3 (Burstein, D. et al., 2017 supra).

Another new class 2 Cas protein is encoded in the genomes of certain candidate phyla radiation (CPR) bacteria. This approximately 1,200 amino acid Cas protein, termed CasY, appears to be part of a minimal CRISPR-Cas system that includes Cas1 and a CRISPR array. Most of the CRISPR arrays have unusually short spacers of 17-19 nt, but one system, which lacks Cas1 (CasY.5), has longer spacers (27-29 nt). Accordingly, in some embodiments of the invention, the CasY molecules comprise CasY.1, CasY.2, CasY.3, CasY.4, CasY.5, CasY.6, mutants, variants, analogs or fragments thereof.

The CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

In some embodiments, the CRISPR/Cas-like protein can be derived from a wild type Cas protein or fragment thereof. In other embodiments, the CRISPR/Cas-like protein can be derived from modified Cas proteins. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In some embodiments, the CRISPR-associated endonuclease can be a sequence from another species, for example, other bacterial species, bacteria genomes and archaea, or other prokaryotic microorganisms. Alternatively, the wild type Cas9, CasX, CasY.1, CasY.2, CasY.3, CasY.4, CasY.5, CasY.6, ARMAN 1, ARMAN 4, sequences can be modified. The nucleic acid sequence can be codon optimized for efficient expression in mammalian cells, i.e., "humanized." A humanized Cas9 nuclease sequence can be for example, the Cas9 nuclease sequence encoded by any of the expression vectors listed in GENBANK accession numbers KM099231.1 GI:669193757; KM099232.1 GI:669193761; or KM099233.1 GI:669193765. Alternatively, the Cas9, CasX, CasY.1, CasY.2, CasY.3, CasY.4, CasY.5, CasY.6, ARMAN 1, ARMAN 4, sequences can be for example, the sequence contained within a commercially available vector such as PX330 or PX260 from Addgene (Cambridge, MA). In some embodiments, the Cas9 endonuclease can have an amino acid sequence that is a variant or a fragment of any of the Cas9 endonuclease sequences of GENBANK accession numbers KM099231.1 GI:669193757; KM099232.1 GI:669193761; or KM099233.1 GI:669193765, or Cas9 amino acid sequence of PX330 or PX260 (Addgene, Cambridge, MA).

The wild type Cas9, CasX, CasY.1, CasY.2, CasY.3, CasY.4, CasY.5, CasY.6, ARMAN 1, ARMAN 4, sequences can be a mutated sequence. For example, the Cas9 nuclease can be mutated in the conserved HNH and RuvC domains, which are involved in strand specific cleavage. In another example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks. The sequences of Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, mutants, variants, high-fidelity variants, orthologs, analogs, fragments, or combinations thereof, can be modified to encode biologically active variants, and these variants can have or can include, for example, an amino acid sequence that differs from a wild type by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, polypeptides can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9, CasX, CasY.1, CasY.2, CasY.3, CasY.4, CasY.5, CasY.6, spCas, eSpCas, SpCas9, ARMAN 1, ARMAN 4 polypeptides. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine (2R,3S)-2-amino-3-methylpentanoic acid and L-cyclopentyl glycine (S)-2-amino-2-cyclopentyl acetic acid.

Two nucleic acids or the polypeptides they encode may be described as having a certain degree of identity to one another. For example, a Cas9 protein and a biologically active variant thereof may be described as exhibiting a certain degree of identity. Alignments may be assembled by locating short Cas9 sequences in the Protein Information Research (PIR) site of Georgetown University, followed by analysis with the "short nearly identical sequences" Basic Local Alignment Search Tool (BLAST) algorithm on the NCBI website (ncbi.nlm.nih.gov/blast).

A percent sequence identity to Cas9 can be determined and the identified variants may be utilized as a CRISPR-associated endonuclease and/or assayed for their efficacy as a pharmaceutical composition. A naturally occurring Cas9 can be the query sequence and a fragment of a Cas9 protein can be the subject sequence. Similarly, a fragment of a Cas9 protein can be the query sequence and a biologically active variant thereof can be the subject sequence. To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., *Nucleic Acids Res.* 31:3497-3500, 2003.

In some embodiments, the isolated nucleic acids sequences can be encoded by the same construct with one or more isolated nucleic acids sequences directed toward a first and second target sequence. In some embodiments, the one or more isolated nucleic acids sequences are encoded by two or more constructs with one member directed toward a first target sequence, and the other member toward a second target sequence excises the mutant genome.

Accordingly, the invention features compositions for use in correcting mutations in target DNA, including an isolated nucleic acid sequence encoding a CRISPR-associated endonuclease and one or more isolated nucleic acid sequences encoding one or more gRNAs complementary to a target sequence. The isolated nucleic acids can include one gRNA, two gRNAs, three gRNAs etc. Furthermore, the isolated nucleic acid can include one or more gRNAs complementary to target sequences in target sequences and a second isolated nucleic acid can include one or more gRNAs complementary to target sequences.

In some embodiments, a composition for correcting target mutations, or excising target mutant sequences in vitro or in vivo comprises at least two isolated nucleic acid sequences encoding: a first Clustered Regularly Interspaced Short Palindromic Repeat (CRISPR)-associated endonuclease and at least one guide RNA (gRNA), the gRNA being complementary to a target sequence; a second Clustered Regularly Interspaced Short Palindromic Repeat (CRISPR)-associated endonuclease and at least one guide RNA (gRNA), the gRNA being complementary to a target sequence in a second target sequence. In some embodiments, the endonuclease comprises Cas9, CasX, CasY.1, CasY.2, CasY.3, CasY.4, CasY.5, CasY.6, spCas, eSpCas, SpCas9-HF1, SpCas9-HF2, SpCas9-HF3, SpCas9-HF4, ARMAN 1, ARMAN 4, mutants, variants, high-fidelity variants, orthologs, analogs, fragments or combinations thereof. The endonucleases may be the same or may vary. For example, one endonuclease may be a Cas9, another endonuclease may be CasY.5 or ARMAN 4 and the like. Accordingly, the isolated nucleic acid sequence can encode any number and type of endonuclease.

The compositions can include guide nucleic acid sequences comprising caged gRNA havening caged nucleotides wherein the caged nucleotides are susceptible to cleavage at different wavelengths. The timing of activating the gene-editing complexes can therefore be controlled and this can vary based on, for example, specific target sequences. For example, target sequence I can be targeted by a gene-editing complex which is cleavable by wavelength I, a second target sequence 2 can be targeted by a gene-editing complex which is cleavable by wavelength II etc. Another example is when target sequence I has multiple regions to be targeted. In this scenario, each of these regions in the target sequence can be targeted by a gene-editing complex which is cleavable by wavelength I. A second region of target sequence I can be targeted by a gene-editing complex which is cleavable by a wavelength 2, etc. Accordingly, in certain embodiments, a method of sequential activation of a gene-editing complex in a host cell comprises contacting the host cell with a composition comprising two or more nucleic acid sequence encoding: a clustered regularly interspaced short palindromic repeats (CRISPR)-associated endonuclease, a Cas peptide and at least one guide RNA (gRNA) each, wherein the at least one guide RNA of each of the nucleic sequences comprise at least one photocleavable caged nucleotide or analogs thereof, subjecting the host cell to varying wavelengths of electromagnetic radiation over intervals of time, thereby cleaving the at least one photocleavable caged nucleotide or analogs thereof, and, sequentially modulating activity of the gene-editing complex over time per target sequence. In certain embodiments, the photocleavable caged nucleotides comprise photocleavable caging groups susceptible to cleavage by electromagnetic radiation of different wavelengths. Each gRNA is substantially complementary to a target sequence in the host cell, wherein each gRNA specific for the similar or substantially similar target sequences comprise photocleavable caged nucleotides comprising photocleavable caging groups cleavable by the same wavelength of electromagnetic radiation.

Cpf1 Endonucleases. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary target sequence (also called protospacer) on the target DNA. Cas9 recognizes a guanine rich trinucleotide (NGG) proto-spacer adjacent motif (PAM) to specify the cut site (the 3rd nucleotide from PAM). The PAM is adjacent to the 3' end of the target sequence.

In contrast, Cpf1 recognizes a thymine rich PAM, with a consensus sequence TTN, and that PAM is located at the 5' end of the target sequence. This gives a CRISPR/Cpf1 system a different repertoire of targets from a CRISPR/Cas9 system, expanding the spectrum of available gene editing targets.

In certain embodiments, the Cpf1 comprise *Acidaminococcus* sp. BV3L6 Cpf1, and Lachnospiraceae bacterium ND2006. These Cpf1 family members have thoroughly characterized, and have been shown to be approximately as effective as Cas9 in editing the DNMT1 gene in human kidney cells (Zetsche B. et al., *Cell* 163, 1-13 Oct. 22, 2015). Alternatively, the Cpf1 of any species can be utilized, if it can be shown to mediate gRNA guided gene editing in a particular cell type or individual animal. The wild type *Acidaminococcus* or Lachnospiraceae Cpf1 sequences can be modified to encode biologically active variants of Cpf1, and these variants can have or can include, for example, an amino acid sequence that differs from a wild type Cpf1 by virtue of containing one or more mutations (e.g., an addition, deletion, or substitution mutation or a combination of such mutations).

The Cpf1 nucleotide sequence can be modified to encode biologically active variants of Cpf1, and these variants can have or can include, for example, an amino acid sequence that differs from a wild type Cpf1 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cpf1 polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cpf1 polypeptide.

Guide Nucleic Acid Sequences: Guide nucleic acid sequences, e.g. gRNA sequences according to the present invention can be sense or anti-sense sequences. The specific sequence of the gRNA may vary, but, regardless of the sequence, useful guide RNA sequences will be those that minimize off-target effects while achieving high efficiency, editing and correction of target gene mutations. The length of the guide sequences can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides. Useful selection methods identify regions having extremely low homology between the target genes and other host cellular genome, include bioinformatic screening using 12-bp+NGG target-selection criteria to exclude off-target human transcriptome or (even rarely) untranslated-genomic sites; and WGS, Sanger sequencing and SURVEYOR assay, to identify and exclude potential off-target effects. In certain embodiments, a guide nucleic acid sequence has a 50% sequence identity to one or more complementary nucleic acid sequences in a target gene.

Accordingly, in certain embodiments a guide nucleic acid e.g. RNA (gRNA) is provided, wherein the gRNA comprises a sequence having one or more caged nucleotides or analogs thereof. In certain aspects, the one or more caged nucleotides or analogs thereof are photocleavable. In certain aspects, the at least one photocleavable caged nucleotide or analogs thereof are positioned distal to a protospacer adjacent motif (PAM) and target sequence. In certain embodiments, the at least one photocleavable caged nucleotides or analogs thereof, comprise one or more caging groups comprising: 6-nitropiperonyloxymethyl; adenosine-5'-diphosphate, P2-(1-(2-nitrophenyl)-ethyl)-ester, potassium salt; adenosine-5'-triphosphate, P3-(1-(2-nitrophenyl)-ethyl)-ester, sodium salt; adenosine-5'-[(β,γ)-imido]triphosphate, P3-(1-(2-nitrophenyl)-ethyl)-ester, triethylammonium salt; adenosine 5'-triphosphate, P3-(1-(4,5-dimethoxy-2-nitrophenyl)ethyl) ester, disodium salt); adenosine 5'-Triphosphate, P3-(1-(2-nitrophenyl)ethyl) ester, disodium salt; 4,5-dimethoxy-2-nitrophenyl-ethyl (DMNPE); [7-(diethylamino)coumarin-4-yl]methyl (DEACM); or combinations thereof. In certain embodiments, the photocleavable caged nucleotide is 6-nitropiperonyloxymethyl modified deoxynucleotide thymine (NPOM-dT). In certain embodiments, the one or more uracil nucleobases in the nucleic acid sequence of the gRNA are substituted with 6-nitropiperonyloxymethyl modified deoxynucleotide thymine (NPOM-dT).

For exposing the compounds to light, whether in vivo or in vitro, the light or electromagnetic radiation may be of any suitable wavelength and intensity, e.g. UV light of 365 nm. In certain embodiments, the electromagnetic radiation comprises a wavelength of between about 190 to about 2400 nm. In certain embodiments, the electromagnetic radiation has a wavelength of about 365 nm. In some embodiments, the photocleavable step is carried out by "two-photon decaging" in accordance with known two-photon excitation techniques. See, e.g., U.S. Pat. Nos. 7,049,480; 6,020,591; and 5,034,613. In some embodiments, two photons of a suitable wavelength (e.g., equal to or greater than 650 or 700 nm) are directed at the caged nucleotide with approximately a 100 femtosecond pulse width and an approximately 80 MHz repetition rate, where they then double up and remove the caging group. Two photon decaging can if desired be facilitated through the use of a two-photon sensitizer. This is an important technique, because photons of such wavelengths can be focused more precisely and penetrate tissue more deeply.

In certain embodiments, the gRNA is complementary to a target sequence in a genome of a cell. In certain aspects, the target sequence comprises one or more genomic sequences associated with a disease. For example, the disease comprises: tumors, virus infections, autoimmunity diseases, diseases associated with genetic mutations or infectious disease organisms. A guide RNA comprises at least a guide-sequence that is able to hybridize with the target sequence and is able to direct sequence-specific binding of the gene editing complex, for example, CRISPR-Cas system, to the target sequence to form a CRISPR-Cas complex. In order to enable formation of an active CRISPR-Cas complex, the guide-polynucleotide also comprises a sequence that has a specific secondary structure and allows binding of the Cas protein to the guide-polynucleotide. Such sequence is known in the art as tracrRNA, tracr sequence, tracr scaffold or guide-polynucleotide structural component, these terms are used interchangeably herein; wherein the tracr is the abbreviation for transactivating CRISPR; tracrRNA thus means transactivating CRISPR RNA. The tracrRNA in the original CRISPR-Cas system is the endogenous bacterial RNA that links thecrRNA (guide-sequence) to the Cas nuclease, being able to bind any crRNA. A guide-polynucleotide structural component may be comprised of a single polynucleotide molecule or may be comprised of two or more molecules hybridized to each other; such hybridizing components of a guide-polynucleotide structural component may be referred to as a tracr sequence and a tracr-mate sequence.

In the context of the present invention, a guide-sequence is referred to as essentially the reverse complement of a target-sequence or of a target-polynucleotide if the subject sequence is able to hybridize with the target-sequence or target-polynucleotide, under physiological conditions as in a host cell. The degree of complementarity between a guide-sequence and its corresponding target-sequence, when optimally aligned using a suitable alignment algorithm, is at least higher than 50%, 60%, 75%, 80%, 85%, 90%, 95%, 97.5%, 99% sequence identity. Optimal alignment may be determined using any suitable algorithm for aligning sequences, such as a BLAST algorithm. When the target-polynucleotide is a double stranded polynucleotide, the subject sequence, such as a guide-sequence, may be able to hybridize with either strand of the target-polynucleotide e.g. a coding strand or a non-coding strand. In certain aspects, a guide-sequence has 100% sequence identity with the 8, 9, 10, 11, 12, 13, 14, 15, 16, 17, 18, 19 or 20, or at least 8, 9, 10, 11 or 12 nucleotides in the target-polynucleotide immediately adjacent to a PAM sequence.

A guide-sequence according to the present invention is 8-30, or 10-30, or 15-30, or 17-27, or 17-20, or 17, 18, 19, 20, 21, 22, 23, 24, 25, 26, or 27 nucleotides in length. The ability of a guide-sequence to direct sequence-specific binding of a CRISPR-Cas system to a target-sequence to form a CRISPR-Cas complex may be assessed by any suitable assay. For example, the components of a CRISPR system sufficient to form a CRISPR-Cas complex, including the guide-sequence to be tested, may be provided to a host cell having the corresponding target-sequence, such, as by transfection with vectors encoding the components of the CRISPR-Cas system, followed by an assessment of preferential cleavage within the target-sequence, such as by the Surveyor assay (SURVEYOR™. Mutation Detection Kits distributed by Integrated DNA Technologies, Leuven, Belgium) or another sequence analysis assay such as sequencing. Cleavage of a target-polynucleotide may be evaluated in a test tube by providing the target-polynucleotide, components of a CRISPR-Cas system, including the guide-sequence to be tested and a control guide-sequence different from the test guide-sequence, and comparing binding or rate of cleavage at the target-sequence between the test and control guide-sequence reactions. Other assays are possible, and are known to a person skilled in the art.

In certain embodiments, a crRNA sequence comprises one or more photocleavable caged nucleotides or analogs thereof, wherein the one or more photocleavable caged nucleotides or analogs thereof are positioned distal to a protospacer adjacent motif (PAM) and target sequence. In certain embodiments, the at least one photocleavable caged nucleotides or analogs thereof, comprise one or more caging groups comprising: 6-nitropiperonyloxymethyl; adenosine-5'-diphosphate, P2-(1-(2-nitrophenyl)-ethyl)-ester, potassium salt; adenosine-5'-triphosphate, P3-(1-(2-nitrophenyl)-ethyl)-ester, sodium salt; adenosine-5'-[(β,γ)-imido]

triphosphate, P3-(1-(2-nitrophenyl)-ethyl)-ester, triethylammonium salt; adenosine 5'-triphosphate, P3-(1-(4, 5-dimethoxy-2-nitrophenyl)ethyl) ester, disodium salt); adenosine 5'-Triphosphate, P3-(1-(2-nitrophenyl)ethyl) ester, disodium salt; 4,5-dimethoxy-2-nitrophenyl-ethyl (DMNPE); [7-(diethylamino)coumarin-4-yl]methyl (DEACM); or combinations thereof. In certain aspects, the at least one photocleavable caged nucleotide is 6-nitropiperonyloxymethyl modified deoxynucleotide thymine (NPOM-dT). In certain embodiments, the one or more uracil nucleobases in the nucleic acid sequence of the gRNA are substituted with 6-nitropiperonyloxymethyl modified deoxynucleotide thymine (NPOM-dT).

In general, guide nucleic acid sequences, e.g. gRNAs will typically contain at least 1 or 2 caged purine or pyrimidine bases, from one up to 50 or 100 caged purine or pyrimidine bases (or up to 30 or 50 percent of the total number of purine or pyrimidine bases being caged purine or pyrimidine bases as described herein, depending upon the length and purpose of the oligonucleotide or oligonucleotide analog. In some embodiments the guide nucleic acid sequences contain from 2 to 5 caged purine or pyrimidine bases as described above (and preferably all of which are the same). When the caging group or groups are subsequently removed (e.g., by exposure to light), the gene-editing complex is activated.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs.

Guide nucleic acid sequences can be complementary to coding or non-coding sequences within a target gene in a host cell genome. In certain embodiments, a gRNA oligonucleotide sequence targets transcriptional regulator elements. In one embodiment, an oligonucleotide comprises at least five consecutive bases complementary to a nucleic acid sequence, wherein the oligonucleotide specifically hybridizes to a nucleic acid sequence comprising one or more mutations or variants of a target sequence in vivo or in vitro. In another embodiment, the gRNA sequences of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the oligonucleotide. These compounds are then tested using the methods described herein to determine their ability to edit and correct a target function, activity or expression.

In some embodiments, homology, sequence identity or complementarity, between the oligonucleotide and target nucleic acid sequences is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%). In some embodiments, homology, sequence identity or complementarity, is about 90%, about 92%, about 94%, about 95%, about 96%, about 97%, about 98%, about 99% or about 100%.

In another embodiment, a guide oligonucleotide comprises combinations of phosphorothioate internucleotide linkages and at least one internucleotide linkage selected from the group consisting of: alkylphosphonate, phosphorodithioate, alkylphosphonothioate, phosphoramidate, carbamate, carbonate, phosphate triester, acetamidate, carboxymethyl ester, and/or combinations thereof.

In another embodiment, a guide nucleic acid sequence optionally comprises at least one modified nucleobase comprising, peptide nucleic acids, locked nucleic acid (LNA) molecules, analogues, derivatives and/or combinations thereof.

An oligonucleotide is specifically hybridizable when binding of the compound to the target nucleic acid interferes with the normal function of the target nucleic acid to cause a loss of activity, and there is a sufficient degree of complementarity to avoid non-specific binding of the oligonucleotide to non-target nucleic acid sequences under conditions in which specific binding is desired. Such conditions include, i.e., physiological conditions in the case of in vivo assays or therapeutic treatment, and conditions in which assays are performed in the case of in vitro assays.

When the compositions are administered as an isolated nucleic acid or are contained within an expression vector, the CRISPR endonuclease, can be encoded by the same nucleic acid or vector as the guide DNA sequences. Alternatively, or in addition, the CRISPR endonuclease can be encoded in a physically separate nucleic acid from the gRNA sequences or in a separate vector.

In some embodiments, a cocktail of guide DNA or guide RNA may be introduced into a cell. The gRNA's are designed to target numerous segments of sequences of the target gene. For example, two, five, seven or eleven gRNA's may be present in an CRISPR cocktail targeting three different segments of sequences. However, any number of gRNA's may be introduced into a cocktail to target segments of sequences. Each of these gRNAs may have caged nucleotides that are photocleavable at different wavelengths.

In some aspects of the invention, in vitro experiments allow for the determination of the most essential targets within target genes. For example, to understand the most essential targets for effective editing and correcting of a genome, subsets of gRNA's are transfected into model cells. Assays can determine which guide oligonucleotide or which cocktail is the most effective at targeting essential segments of sequences.

Targeting an oligonucleotide to a particular nucleic acid molecule, in the context of this invention, can be a multistep process. The process usually begins with the identification of a target nucleic acid sequence whose function, activity, expression and the like is associated with a particular disorder or disease state, e.g. IDC.

The targeting process usually also includes determination of at least one target region, segment, or site within the target nucleic acid for the antisense interaction to occur such that the desired effect will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Modified or Mutated Nucleic Acid Sequences: In some embodiments, any of the nucleic acid sequences may be modified or derived from a native nucleic acid sequence, for example, by introduction of mutations, deletions, substitutions, modification of nucleobases, backbones and the like. The nucleic acid sequences include the vectors, gene-editing agents, gRNAs, etc. Examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —$N(CH_3)$—O—$CH_2$ [known as a methylene(methylimino) or MMI backbone], $CH_2$—O—$N(CH_3)$—$CH_2$, $CH_2$—$N(CH_3)$—N$(CH_3)$—$CH_2$ and O—$N(CH_3)$—$CH_2$—$CH_2$ backbones, wherein the native phosphodiester backbone is represented as O—P—O—CH,). The amide backbones disclosed by De Mesmaeker et al. *Acc. Chem. Res.* 1995, 28:366-374) are also embodied herein. In some embodiments, the nucleic acid sequences having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). The nucleic acid sequences may also comprise one or more substituted sugar moieties. The nucleic acid sequences may also have sugar mimetics such as cyclobutyls in place of the pentofuranosyl group.

The nucleic acid sequences may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-77; Gebeyehu, G., et al. *Nucl. Acids Res.* 1987, 15:4513). A "universal" base known in the art, e.g., inosine may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278).

Nucleic acid sequences may also comprise one or more substituted sugar moieties. Examples include: OH, SH, $SCH_3$, F, OCN, $OCH_3$ $OCH_3$, OCH3 $O(CH_2)_n$ $CH_3$, $O(CH_2)_n$ $NH_2$ or $O(CH_2)_n$ $CH_3$ where n is from 1 to about 10; $C_1$ to $C_{10}$ lower alkyl, alkoxyalkoxy, substituted lower alkyl, alkaryl or aralkyl; CI; Br; CN; $CF_3$; $OCF_3$; O—, S—, or N-alkyl; O—, S—, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; a reporter group; an intercalator; a group for improving the pharmacokinetic properties of an oligonucleotide; or a group for improving the pharmacodynamic properties of an oligonucleotide and other substituents having similar properties. Other modifications include, for example: 2'-methoxyethoxy [2'-O—$CH_2$ $CH_2OCH_3$, also known as 2'-O-(2-methoxyethyl)](Martin et al, (1995) *Helv. Chim. Acta,* 78, 486), 2'-methoxy (2'-O—$CH_3$), 2*-propoxy (2'-$OCH_2$ $CH_2CH_3$) and 2'-fluoro (2'-F). Similar modifications may also be made at any positions on the oligonucleotide, the 2' or the 3' position of the sugar on the 3' terminal nucleotide and the 5' position of 5' terminal nucleotide. The nucleic acid sequences may also have sugar mimetics such as cyclobutyls in place of the pentofuranosyl group.

Another modification of the nucleic acid sequences of the invention involves chemically linking to the nucleic acid sequences one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci.* USA 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651).

It is not necessary for all positions in a given nucleic acid sequence to be uniformly modified, and in fact more than one of the aforementioned modifications may be incorporated in a single nucleic acid sequence or even at within a single nucleoside within a nucleic acid sequence.

In some embodiments, the guide molecules e.g., gRNA are engineered to comprise one or more modified nucleobases. For example, known modifications of RNA molecules can be found, for example, in Genes VI, Chapter 9 ("Interpreting the Genetic Code"), Lewis, ed. (1997, Oxford University Press, New York), and Modification and Editing of RNA, Grosjean and Benne, eds. (1998, ASM Press, Washington DC). Modified RNA components include the following: 2'-O-methylcytidine; $N^4$-methylcytidine; $N^4$-2'-O-dimethylcytidine; $N^4$-acetylcytidine; 5-methylcytidine; 5,2'-O-dimethylcytidine; 5-hydroxymethylcytidine; 5-formylcytidine; 2'-O-methyl-5-formaylcytidine; 3-methylcytidine; 2-thiocytidine; lysidine; 2'-O-methyluridine; 2-thiouridine; 2-thio-2'-O-methyluridine; 3,2'-O-dimethyluridine; 3-(3-amino-3-carboxypropyl)uridine; 4-thiouridine; ribosylthymine; 5,2'-O-dimethyluridine; 5-methyl-2-thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5-methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl)uridine; 5-(carboxyhydroxymethyl) uridinemethyl ester; 5-aminomethyl-2-thiouridine; 5-methylaminomethyluridine; 5-methylaminomethyl-2-thiouridine; 5-methylaminomethyl-2-selenouridine; 5-carboxymethylaminomethyluridine; 5-carboxymethylaminomethyl-2'-O-methyl-uridine; 5-carboxymethylaminomethyl-2-thiouridine; dihydrouridine; dihydroribosylthymine; 2'-methyladenosine; 2-methyladenosine; $N^6$Nmethyladenosine; $N^6$, $N^6$-dimethyladenosine; $N^6$,2'-O-trimethyladenosine; 2 methylthio-$N^6$Nisopentenyladenosine; $N^6$-(cis-hydroxyisopentenyl)-adenosine; 2-methylthio-$N^6$-(cis-hydroxyisopentenyl)- adenosine; N⁶-glycinylcarbamoyl)adenosine; N⁶ threonylcarbamoyl adenosine; N⁶-methyl-N⁶-threonylcarbamoyl adenosine; 2-methylthio-N⁶-methyl-N⁶-threonylcarbamoyl adenosine; N⁶-hydroxynorvalylcarbamoyl adenosine; 2-methylthio-N⁶-hydroxnorvalylcarbamoyl adenosine; 2'-O-ribosyladenosine (phosphate); inosine; 2'O-methyl inosine; 1-methyl inosine; 1; 2'-O-dimethyl inosine; 2'-O-methyl guanosine; 1-methyl guanosine; N²-methyl guanosine; N², N²-dimethyl guanosine; N², 2'-O-dimethyl guanosine; N², N², 2'-O-trimethyl guanosine; 2'-O-ribosyl guanosine (phosphate); 7-methyl guanosine; N²; 7-dimethyl guanosine; N²; N²; 7-trimethyl guanosine; wyosine; methylwyosine; under-modified hydroxywybutosine; wybutosine; hydroxywybutosine; peroxywybutosine; queuosine; epoxyqueuosine; galactosyl-queuosine; mannosyl-queuosine; 7-cyano-7-deazaguanosine; arachaeosine [also called 7-formamido-7-deazaguanosine]; and 7-aminomethyl-7-deazaguanosine.

In certain embodiments, the nucleic acid sequences are chimeric nucleic acid sequences. "Chimeric nucleic acid sequences" or "chimeras," in the context of this invention, contain two or more chemically distinct regions, each made up of at least one nucleotide. These sequences typically contain at least one region of modified nucleotides that confers one or more beneficial properties (such as, for example, increased nuclease resistance, increased uptake into cells, increased binding affinity for the target). Chimeric nucleic acid sequences of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another embodiment, the guide oligonucleotides comprise one or more nucleotides substituted with locked nucleic acids (LNA). The LNA modified nucleic acid sequences may have a size similar to the parent or native sequence or may be larger or preferably smaller. It is preferred that such LNA-modified oligonucleotides contain less than about 70%, less than about 60%, less than about 50% LNA monomers and that their sizes are between about 1 and 25 nucleotides The nucleic acid molecules of the present invention can be produced by standard techniques. For example, polymerase chain reaction (PCR) techniques can be used to obtain an isolated nucleic acid containing a nucleotide sequence described herein. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Recombinant Constructs and Delivery Vehicles.

Exemplary expression vectors for inclusion in the pharmaceutical composition include plasmid vectors and lentiviral vectors, but the present invention is not limited to these vectors. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA). A marker gene can confer a selectable phenotype on a host cell. For example, a marker can confer biocide resistance, such as resistance to an antibiotic (e.g., kanamycin, G418, bleomycin, or hygromycin). An expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FLAG™ tag (Kodak, New Haven, CT) sequences typically are expressed as a fusion with the encoded polypeptide. Such tags can be inserted anywhere within the polypeptide, including at either the carboxyl or amino terminus. The vector can also include origins of replication, scaffold attachment regions (SARs), regulatory regions and the like. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns. The term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other promoter (e.g., cellular promoters such as eukaryotic cellular promoters including, but not limited to, the histone, pol III, and (β-actin promoters). Other viral promoters which may be employed include, but are not limited to, adenovirus promoters, TK promoters, and B19 parvovirus promoters.

Expression of the nucleic acid sequences may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. Nos. 5,385,839 and 5,168,062), the SV40 early promoter region (Benoist and Chambon, 1981, Nature 290:304-310), the promoter contained in the 3' long terminal repeat of Rous sarcoma virus (Yamamoto, et al., *Cell* 22:787-797, 1980), the herpes thymidine kinase promoter (Wagner et al., *Proc. Natl. Acad. Sci.* U.S.A. 78:1441-1445, 1981), the regulatory sequences of the metallothionein gene (Brinster et al., *Nature* 296:39-42, 1982); prokaryotic expression vectors such as the β-lactamase promoter (Villa-Kamaroff, et al., *Proc. Natl. Acad. Sci.* U.S.A. 75:3727-3731, 1978), or the tac promoter (DeBoer, et al., *Proc. Natl. Acad. Sci. U.S.A.* 80:21-25, 1983); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., *Cell* 38:639-646, 1984; Ornitz et al., Cold Spring Harbor Symp. *Quant. Biol.* 50:399-409, 1986; MacDonald, *Hepatology* 7:425-515, 1987); insulin gene control region which is active in pancreatic beta cells (Hanahan, *Nature* 315:115-122, 1985), immunoglobulin gene control region which is active in lymphoid cells (Grosschedl et al., *Cell* 38:647-658, 1984; Adames et al., *Nature* 318:533-538, 1985; Alexander et al., *Mol. Cell. Biol.* 7:1436-1444, 1987), mouse mammary tumor virus control region which is active in testicular, breast, lymphoid and mast cells (Leder et al., *Cell* 45:485-495, 1986), albumin gene control region which is active in liver (Pinkert et al., *Genes and Devel.* 1:268-276, 1987), alpha-fetoprotein gene control region which is active in liver (Krumlauf et al., *Mol. Cell. Biol.* 5:1639-1648, 1985; Hammer et al., *Science* 235:53-58, 1987), alpha 1-antitrypsin gene control region which is active in the liver (Kelsey et al., *Genes and Devel.* 1: 161-171, 1987), beta-globin gene control region which is active in myeloid cells (Mogram et al., *Nature* 315:338-340, 1985; Kollias et al., *Cell* 46:89-94, 1986), myelin basic protein gene control region which is active in oligodendrocyte cells in the brain (Readhead et al., *Cell* 48:703-712, 1987), myosin light chain-2 gene control region which is active in skeletal muscle (Sani, *Nature* 314:283-286, 1985), and gonadotropic releasing hormone gene control region which is active in the hypothalamus (Mason et al., *Science* 234:1372-1378, 1986).

In another embodiment the invention comprises an inducible promoter. One such promoter is the tetracycline-controlled transactivator (tTA)-responsive promoter (tet system), a prokaryotic inducible promoter system which has been adapted for use in mammalian cells. The tet system was organized within a retroviral vector so that high levels of constitutively-produced tTA mRNA function not only for production of tTA protein but also the decreased basal expression of the response unit by antisense inhibition. See, Paulus, W. et al., "Self-Contained, Tetracycline-Regulated Retroviral Vector System for Gene Delivery to Mammalian Cells", J of Virology, January. 1996, Vol. 70, No. 1, pp. 62-67. The selection of a suitable promoter will be apparent to those skilled in the art from the teachings contained herein.

The present invention provides expression vectors for use in expressing the nucleic acid sequences a host cell. Each expression vector includes at least one isolated nucleic acid sequence encoding, for example, Cas9, an endonuclease, at least one (gRNA), and the like. A nucleic acid sequence encoding an endonuclease, and a nucleic acid sequence encoding at least one gRNA, can be included in a single expression vector, or in separate vectors.

In certain embodiments, the vector for expressing the gene editing systems of the invention in mammalian cells is a lentiviral vector, because of its high transduction efficiency and low toxicity. Other suitable expression vectors include, without limitation, plasmids and viral vectors derived from, for example, bacteriophage, baculoviruses, retroviruses. adenoviruses ("Ad"), adeno-associated viruses (AAV), and vesicular stomatitis virus (VSV), and pox viral vectors such as avipox or orthopox vectors. Additional expression vectors also can include derivatives of SV40 and known bacterial plasmids, e.g., *E. coli* plasmids col E1, pCR1, pBR322, pMal-C2, pET, pGEX, pMB9 and their derivatives; plasmids such as RP4; phage DNAs, e.g., the numerous derivatives of phage 1, e.g., NM989, and other phage DNA, e.g., M13 and filamentous single stranded phage DNA; yeast plasmids such as the 2μ plasmid or derivatives thereof, and vectors derived from combinations of plasmids and phage DNAs, such as plasmids that have been modified to employ phage DNA or other expression control sequences. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA). Suitable promoters and enhancers can be included in the vectors, with the selection being made according to the cell type in which expression is desired, by experimental means well known in the art.

The polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Felgner and Holm, *Bethesda Res. Lab. Focus,* 11(2):21 (1989) and Maurer, R. A., *Bethesda Res. Lab. Focus,* 11(2):25 (1989). Therefore, the present invention encompasses a lentiviral vector composition for expression in a host cell. The composition includes an isolated nucleic acid encoding an endonuclease, and at least one isolated nucleic acid encoding at least one guide gRNA including a spacer sequence that is complementary to a desired target sequence and includes at least one photocleavable caged nucleotide, with the isolated nucleic acids being included in at least one lentiviral expression vector. The lentiviral expression vector induces the expression of the endonuclease and the at least one gRNA in a host cell.

All of the isolated nucleic acids can be included in a single lentiviral expression vector, or the nucleic acids can be subdivided into any suitable combination of lentiviral vectors. For example, the endonuclease can be incorporated into a first lentiviral expression vector, a first gRNA can be incorporated into a second lentiviral expression vector, and a second gRNA can be incorporated into a third lentiviral expression vector. When multiple expression vectors are used, it is not necessary all of them be lentiviral vectors.

Recombinant constructs are also provided herein and can be used to transform cells.

Several delivery methods may be utilized in conjunction with the molecules embodied herein for in vitro (cell cultures) and in vivo (animals and patients) systems. In one embodiment, a lentiviral gene delivery system may be utilized. Such a system offers stable, long term presence of the gene in dividing and non-dividing cells with broad tropism and the capacity for large DNA inserts. (Dull et al, *J Virol,* 72:8463-8471 1998). In an embodiment, adeno-associated virus (AAV) may be utilized as a delivery method. AAV is a non-pathogenic, single-stranded DNA virus that has been actively employed in recent years for delivering therapeutic gene in in vitro and in vivo systems (Choi et al, *Curr Gene Ther,* 5:299-310, 2005).

In certain embodiments of the invention, non-viral vectors may be used to effectuate transfection. Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam and Lipofectin). Cationic and neutral lipids that are suitable for efficient receptor-recognition lipofection of polynucleotides include those described in U.S. Pat. No. 7,166,298 to Jessee or U.S. Pat. No. 6,890,554 to Jesse, the contents of each of which are incorporated by reference. Delivery can be to cells (e.g. in vitro or ex vivo administration) or target tissues (e.g. in vivo administration).

Synthetic vectors are typically based on cationic lipids or polymers which can complex with negatively charged nucleic acids to form particles with a diameter in the order of 100 nm. The complex protects nucleic acid from degradation by nuclease. Moreover, cellular and local delivery strategies have to deal with the need for internalization, release, and distribution in the proper subcellular compartment. Systemic delivery strategies encounter additional hurdles, for example, strong interaction of cationic delivery vehicles with blood components, uptake by the reticuloendothelial system, kidney filtration, toxicity and targeting ability of the carriers to the cells of interest. Modifying the surfaces of the cationic non-virals can minimize their interaction with blood components, reduce reticuloendothelial system uptake, decrease their toxicity and increase their binding affinity with the target cells. Binding of plasma proteins (also termed opsonization) is the primary mechanism for RES to recognize the circulating nanoparticles. For example, macrophages, such as the Kupffer cells in the liver, recognize the opsonized nanoparticles via the scavenger receptor.

The nucleic acid sequences of the invention can be delivered by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm). Another way to achieve uptake of the nucleic acid is using liposomes, prepared by standard methods. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding an isolated nucleic acid sequence comprises a sequence encoding an endonuclease and/or a guide RNA with a photocleavable caged nucleotide, as described above.

In some embodiments, delivery of vectors can also be mediated by exosomes. Exosomes are lipid nanovesicles released by many cell types. They mediate intercellular communication by transporting nucleic acids and proteins between cells. Exosomes contain RNAs, miRNAs, and proteins derived from the endocytic pathway. They may be taken up by target cells by endocytosis, fusion, or both. Exosomes can be harnessed to deliver nucleic acids to specific target cells.

The expression constructs of the present invention can also be delivered by means of nanoclews. Nanoclews are a cocoon-like DNA nanocomposites (Sun, et al., *J. Am. Chem. Soc.* 2014, 136:14722-14725). They can be loaded with nucleic acids for uptake by target cells and release in target cell cytoplasm. Methods for constructing nanoclews, loading them, and designing release molecules can be found in Sun, et al. (Sun W, et al., *J Am. Chem. Soc.* 2014, 136: 14722-14725; Sun W, et al., *Angew. Chem. Int. Ed.* 2015: 12029-12033.)

The nucleic acids and vectors may also be applied to a surface of a device (e.g., a catheter) or contained within a pump, patch, or any other drug delivery device. The nucleic acids and vectors disclosed herein can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

In some embodiments of the invention, liposomes are used to effectuate transfection into a cell or tissue. The pharmacology of a liposomal formulation of nucleic acid is largely determined by the extent to which the nucleic acid is encapsulated inside the liposome bilayer. Encapsulated nucleic acid is protected from nuclease degradation, while those merely associated with the surface of the liposome is not protected. Encapsulated nucleic acid shares the extended circulation lifetime and biodistribution of the intact liposome, while those that are surface associated adopt the pharmacology of naked nucleic acid once they disassociate from the liposome. Nucleic acids may be entrapped within liposomes with conventional passive loading technologies, such as ethanol drop method (as in SALP), reverse-phase evaporation method, and ethanol dilution method (as in SNALP).

Liposomal delivery systems provide stable formulation, provide improved pharmacokinetics, and a degree of 'passive' or 'physiological' targeting to tissues. Encapsulation of hydrophilic and hydrophobic materials, such as potential chemotherapy agents, are known. See for example U.S. Pat. No. 5,466,468 to Schneider, which discloses parenterally administrable liposome formulation comprising synthetic lipids; U.S. Pat. No. 5,580,571, to Hostetler et al. which discloses nucleoside analogues conjugated to phospholipids; U.S. Pat. No. 5,626,869 to Nyqvist, which discloses pharmaceutical compositions wherein the pharmaceutically active compound is heparin or a fragment thereof contained in a defined lipid system comprising at least one amphiphatic and polar lipid component and at least one nonpolar lipid component.

Liposomes and polymerosomes can contain a plurality of solutions and compounds. In certain embodiments, the complexes of the invention are coupled to or encapsulated in polymersomes. As a class of artificial vesicles, polymersomes are tiny hollow spheres that enclose a solution, made using amphiphilic synthetic block copolymers to form the vesicle membrane. Common polymersomes contain an aqueous solution in their core and are useful for encapsulating and protecting sensitive molecules, such as drugs, enzymes, other proteins and peptides, and DNA and RNA fragments. The polymersome membrane provides a physical barrier that isolates the encapsulated material from external materials, such as those found in biological systems. Polymerosomes can be generated from double emulsions by known techniques, see Lorenceau et al., 2005, Generation of Polymerosomes from Double-Emulsions, Langmuir 21(20): 9183-6, incorporated by reference.

In some embodiments of the invention, targeted controlled-release systems responding to the unique environments of tissues and external stimuli are utilized. Gold nanorods have strong absorption bands in the near-infrared region, and the absorbed light energy is then converted into heat by gold nanorods, the so-called "photothermal effect". Because the near-infrared light can penetrate deeply into tissues, the surface of gold nanorod could be modified with nucleic acids for controlled release. When the modified gold nanorods are irradiated by near-infrared light, nucleic acids are released due to thermo-denaturation induced by the photothermal effect. The amount of nucleic acids released is dependent upon the power and exposure time of light irradiation.

Regardless of whether compositions are administered as nucleic acids or polypeptides, they are formulated in such a way as to promote uptake by the mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems.

In other embodiments, the compositions comprise a cell which has been transformed or transfected with one or more Cas9 encoding vectors and gRNAs. In some embodiments, the methods of the invention can be applied ex vivo. That is, a subject's cells can be removed from the body and treated with the compositions in culture to excise, for example, desired nucleic acid sequences e.g. viral infections such as HIV and the treated cells returned to the subject's body. The cell can be the subject's cells or they can be haplotype matched or a cell line. The cells can be irradiated to prevent replication. In some embodiments, the cells are human leukocyte antigen (HLA)-matched, autologous, cell lines, or combinations thereof. In other embodiments the cells can be a stem cell. For example, an embryonic stem cell or an artificial pluripotent stem cell (induced pluripotent stem cell (iPS cell)). Embryonic stem cells (ES cells) and artificial pluripotent stem cells (induced pluripotent stem cell, iPS cells) have been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

Transduced cells are prepared for reinfusion according to established methods. After a period of about 2-4 weeks in culture, the cells may number between $1 \times 10^6$ and $1 \times 10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent. For administration, cells of the present invention can be administered at a rate determined by the $LD_{50}$ of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces that may include, but are not restricted to, bone marrow or adipose tissues.

The therapeutic uses include, for example, virus infections, tumors, autoimmune diseases melanomas, and the like. The compositions can be utilized to edit a viral genome and inactivate the virus, e.g. HIV. The compositions can correct mutations, e.g. sickle cell anemia. In such cases, the compositions include a caged nucleotide. A therapeutically effective amount of a composition (i.e., an effective dosage) can be delivered means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

The pharmaceutical compositions of the present invention can be prepared in a variety of ways known to one of ordinary skill in the art. Regardless of their original source or the manner in which they are obtained, the compositions of the invention can be formulated in accordance with their use. For example, the nucleic acids and vectors described above can be formulated within compositions for application to cells in tissue culture or for administration to a patient or subject. Any of the pharmaceutical compositions of the invention can be formulated for use in the preparation of a medicament, and particular uses are indicated below in the context of treatment, e.g., the treatment of a subject having an HIV infection or at risk for contracting and HIV infection. When employed as pharmaceuticals, any of the nucleic acids and vectors can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

Kits

The present invention also includes a kit to facilitate the application of the previously stated methods. The kit includes a measured amount of a composition including at least one isolated nucleic acid sequence encoding an endonuclease, and at least one nucleic acid sequence encoding one or more gRNAs, wherein each of the gRNAs includes at least one photocleavable caged nucleotide. The kit also includes and one or more items selected from the group consisting of packaging material, a package insert comprising instructions for use, a sterile fluid, a syringe and a sterile container. In a preferred embodiment, the nucleic acid sequences are included in an expression vector. The kit can also include a suitable stabilizer, a carrier molecule, a flavoring, or the like, as appropriate for the intended use.

Accordingly, packaged products (e.g., sterile containers containing one or more of the compositions described herein and packaged for storage, shipment, or sale at concentrated or ready-to-use concentrations) and kits, including at least one composition of the invention, e.g., a nucleic acid sequence encoding an endonuclease, a guide RNA comprising at least one photocleavable caged nucleotide, or a vector encoding that nucleic acid and instructions for use, are also within the scope of the invention. A product can include a container (e.g., a vial, jar, bottle, bag, or the like) containing one or more compositions of the invention. In addition, an article of manufacture further may include, for example, packaging materials, instructions for use, syringes, delivery devices, buffers or other control reagents for treating or monitoring the condition for which prophylaxis or treatment is required.

The product may also include a legend (e.g., a printed label or insert or other medium describing the product's use (e.g., an audio- or videotape)). The legend can be associated with the container (e.g., affixed to the container) and can describe the manner in which the compositions therein should be administered and may include one or more additional pharmaceutically acceptable adjuvants, carriers or other diluents and/or an additional therapeutic agent. Alternatively, the compositions can be provided in a concentrated form with a diluent and instructions for dilution.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

EXAMPLES

Example 1: An Inducible CRISPR/Cas9 System for Genome Editing

A very fast CRISPR/Cas9 system that allows genomic manipulation on demand at submicron length scale and seconds time scale was developed. By synchronously creating double strand breaks (DSBs) among a population of cells, the kinetic model for repair of Cas9-mediated DSBs was refined. Through live cell imaging after very fast DNA cleavage at single cell and single allele resolutions, the early molecular events that underlie the initiation and progression of repair at Cas9-induced DNA breaks were characterized.

Materials and Methods

Cas9 Purification

BL21-CodonPlus (DE3)-RIL competent cells (Agilent Technologies 230245) were transformed with Cas9 plasmid (Addgene #67881) and inoculated in 5 ml of LB-ampicillin media. The bacteria culture was first allowed to grow overnight (37° C., 220 rpm) and then transferred to 1 L of LB supplemented with ampicillin and 0.1% glucose until $OD_{600}$ of ~0.5. Subsequently, the cells were induced with IPTG at a final concentration of 0.2 mM and maintained overnight at 18° C. The bacteria cells were pelleted at 4500×g, 4° C. for 15 min and resuspended in 20 ml of lysis buffer containing 20 mM Tris pH 8.0, 250 mM KCl, 20 mM imidazole, 10% glycerol, 1 mM TCEP, 1 mM PMSF, and COMPLETE™ EDTA-free protease inhibitor tablet (Sigma-Aldrich 11836170001). This cell suspension was lysed using a microfluidizer and the supernatant containing Cas9 protein was clarified by spinning down cell debris at 16,000×g, 4° C. for 40 min and filtering with 0.2 μm syringe filters (THERMO SCIENTIFIC™ F25006). Ni-NTA agarose bead slurry (Qiagen 30210) was pre-equilibrated with 5 column volumes of lysis buffer. The clarified supernatant was then loaded at 4° C. The protein-bound Ni-NTA beads were washed with 15 column volumes wash buffer containing 20 mM Tris pH 8.0, 800 mM KCl, 20 mM imidazole, 10% glycerol, and 1 mM TCEP. Gradient elution was performed with buffer containing 20 mM HEPES pH 8.0, 500 mM KCl, 10% glycerol, and varying concentrations of imidazole (100, 150, 200, and 250 mM) at 7 ml collection volume per fraction. The eluted fractions were tested on an SDS-PAGE gel and imaged by Coomassie blue (Biorad 1610400) staining. To remove any DNA contamination, 1 ml Q SEPHAROSE® column (GE Healthcare 17051005) was charged with 1 M KCl and then equilibrated with elution buffer containing 250 mM imidazole. The purified protein solution was then passed over the Q column at 4° C. The flow-through was collected and dialyzed in a 10 kDa SNAKESKIN™ dialysis tubing (Thermo Fisher Scientific 68100) against 2 L of 20 mM HEPES pH 7.5, and 500 mM KCl, 20% glycerol at 4° C., overnight. Next day, the protein was dialyzed for an additional 3 hours in fresh dialysis buffer. The final Cas9 protein was concentrated to 10 μg/μl using AMICON® Ultra 10 kDa centrifugal filter unit (Millipore UFC801024), aliquoted, and flash-frozen and stored at −80° C.

Cell Culture

Human embryonic kidney 293 cell line (HEK293T) and human U-2 osteoscarcoma cell line (U-2 OS) were cultured at 37° C. under 5% $CO_2$ in Dulbecco's Modified Eagle's Medium (DMEM, Corning), supplemented with 10% FBS (Corning), 100 units/ml penicillin and 100 μg/ml streptomycin (DMEM complete). Cells were tested every month for mycoplasma.

Electroporation of Cas9 RNP

To anneal cr:tracr cgRNA, equal volumes of 100 μM cgRNA (Bio-Synthesis Inc) with tracrRNA (Integrated DNA Technologies) were mixed and heated to 95° C. for 5 min in a thermocycler. The mixture was allowed to cool on benchtop for 5 min. To form RNP complex, 10 μg/μl of purified Cas9 was mixed with 50 μM cr:tracr cgRNA at a ratio of 1:1.2, which was then incubated for additional 20 min at room temperature. Cells were properly maintained to a confluency of ~90% prior to electroporation. Cells were then trypsinized and centrifuged in DMEM and 1×PBS sequentially (3 min, 200 g). Supernatant was discarded and 20 μL of nucleofection solution (Lonza) was mixed thoroughly with cell pellet, prior to the addition of 5 μL RNP solution. 1 μL of Cas9 Electroporation Enhancer (Integrated DNA Technologies) was also included. Electroporation was performed according to the manufacturer's instructions on the 4D-NUCLEOFECTOR™ Core Unit (Lonza). SF Cell Line 4D-NUCLEOFECTOR™ X Kit S with code CA-189 was used for HEK293T cells. SE Cell Line 4D-NUCLEOFECTOR™ X Kit S with code DN-100 was used for U-2 OS cells. DMEM complete was added before plating to culture wells.

Preparing Samples for CRISPR-Cas9 Kinetics Measurements in Cells

HEK 293T cells were introduced with Cas9 RNP through electroporation, plated to 96-wells, and incubated in standard cell culture conditions. 12 h after electroporation, cells were exposed to a flashlight that delivered 1.3 J/cm² of 365 nm wavelength light. Cells were harvested at different time points by removal of media and washing with 200 μL/well ice-cold DPBS. Cells were subsequently placed on ice before they were transferred to −80° C. To harvest genomic DNA from cells, cells were immediately taken out of −80° C. and placed in 95° C. heat block for 5 min. Samples were transferred to ice and genomic DNA was isolated using PURELINK™ Genomic DNA Mini Kit (Thermo Fisher Scientific K182001) according to the manufacturer's instructions, except with 1 h (instead of 10 min) incubation with lysis buffer/Proteinase K/RNase A at 55° C.

Sanger Sequencing for Measuring Insertions or Deletions

Genomic DNA samples were amplified with PCR using Q5 Hot Start High-Fidelity 2X Master Mix (New England BioLabs M0494). PCR amplification was performed with the following conditions for ACTB, MYC, and PPP1R2: 98° C. for 30 sec, 35 cycles of [98° C. for 10 sec, 71° C. (ACTB)/67° C. (MYC)/68° C. (PPP1R2) for 10 sec, 72° C. for 20 sec], 72° C. for 2 min, and 4° C. hold. For IFT88: 98° C. for 30 sec, 35 cycles of {98° C. for 10 sec, 60° C. for 20 sec, 65° C. for 40 sec}, 65° C. for 5 min, and 4° C. hold. After PCR, cleanup was performed using QiaQuick PCR Purification Kit (Qiagen 28104) following the manufacturer's instructions. 3 ng/μl of each sample was submitted to Genewiz for Sanger sequencing. Indels were calculated using TIDE analysis (Brinkman E K, Chen T, Amendola M, van Steensel B. Easy quantitative assessment of genome editing by sequence trace decomposition. *Nucleic Acids Res.* 2014 Dec. 16; 42(22):e168. doi: 10.1093/nar/gku936. Epub 2014 Oct. 9. PMID: 25300484; PMCID: PMC4267669).

Next Generation Amplicon Sequencing for Measuring Insertions or Deletions

Genomic DNA samples were amplified with PCR using Q5 Hot Start High-Fidelity 2X Master Mix (New England BioLabs M0494). PCR amplification as performed with the following conditions: 98° C. for 30 sec, 31 cycles (ACTB), 33 cycles (MYC and IFT88), or 32 cycles (PPP1R2) of [98° C. for 10 sec, 71° C. (ACTB)/65° C. (MYC)/58° C. (IFT88)/68° C. (PPP1R2) for 10 sec, 72° C. for 20 sec], 72° C. for 5 min, and 4° C. hold. After amplicon PCR, cleanup was performed using 1.6×AMPure XP (Beckman Coulter A63881) following the manufacturer's instructions. Dual-indexing PCR was performed using KAPA HiFi HotStart ReadyMix (Roche 07958935001) with the following conditions: 95° C. for 3 min, 10 cycles of [95° C. for 30 sec, 55° C. for 30 sec, 72° C. for 30 sec], 72° C. for 5 min, and 4° C. hold. PCR cleanup was performed using 1×AMPure XP; samples were pooled, diluted, and loaded onto a MiSeq (Illumina). Sequencing was performed with the following number of cycles "151|8|8 151" with the paired-end Nextera sequencing protocol. Sequencing reads were either demultiplexed automatically using MiSeq Reporter (Illumina) or with a custom Python script to individual FASTQ files. For indel calling, sequencing reads were scanned for exact matches to two 20-bp sequences that flank+/−20 bp from the ends of the target sequence. If no exact matches were found, the read was excluded from analysis. After additional filtering for an average quality score >20, an indel is defined as a sequence that differs in length from the reference length.

Droplet Digital PCR Assay for Measuring Double-Strand Break Frequencies

Two amplicons were designed for each locus of interest. One amplicon (target1) includes the Cas9 cleavage site; the other (target2) is a nearby sequence that is not cleaved. One dual-quenched qPCR probe (IDT) was designed for each amplicon. Primers and probes were designed using guidelines by Bio-Rad (planning-droplet-digital-pcr-experiments). 10-50 ng of purified genomic DNA were added to a 20 μL reaction with final probe concentration of 900 nM and final primer concentration of 250 nM. For all four loci tested (ACTB, IFT88, MYC), BamHI-HF (New England BioLabs) were added to the reaction mixture to ensure better separation of signals during amplification. Droplets were created using Droplet Generation Oil for Probes, DG8 Gaskets, DG8 Cartridges, and QX200 Droplet Generator (Bio-Rad); PCR amplification was performed using ddPCR Supermix for Probes (no dUTP) (Bio-Rad). Droplets were transferred to a 96-well PCR plate and heat-sealed using PX1 PCR Plate Sealer (Bio-Rad). PCR amplification was performed with the following conditions: 95° C. for 10 min, 40 cycles of [94° C. for 30 sec, variable annealing temperatures for 30 sec, 72° C. for 2 min], 98° C. for 10 min, 12° C. hold. Annealing temperatures for ACTB, IFT88, and MYC were 60° C., 56° C., and 54° C., respectively. Following PCR, droplets were individually scanned by the QX200 Droplet Digital PCR system (Bio-Rad). Droplets plotted in each fluorescent channel (FAM/HEX) were all well separated in clusters, and a threshold was set to bin droplets to positive and negative labels.

To generate standard curves, DNA harvested from wild-type HEK293T cells was cleaved using restriction enzymes (FIGS. 8A-8D). Restriction enzymes were selected to only cleave within target1, and not target2. EcoRV-HF was used for ACTB locus, and SfcI was used for IFT88 and MYC loci (New England BioLabs) according to manufacturer's instructions. Cleaved and non-cleaved DNA samples were mixed at ratios of 1:0, 2:1, 1:1, 1:2, 1:4, 1:10, 1:100, 0:1. ddPCR was performed on the samples with the same protocol as Cas9 cleavage samples. Duplicates were obtained for each locus and linear regression was calculated using all data points.

Double-strand break (DSB) frequency was calculated using the following formula: [target1−,target2+]/([target1−, target2+]+[target1+,target2+]), where target1− indicates negative droplets for the target1 amplicon, target2+ indicates positive droplets for the target2 amplicon.

In vitro Cleavage Assay and Electrophoretic Mobility Shift Assay (EMSA)

10 μM cr:tracr cgRNA solution was prepared at equal molar ratio by heating to 95° C. for 5 min and cooling on heat block for 1 hour. 3 pmol of Cas9 was incubated with 5 pmol of cgRNA to form RNP for 30 min in 10 μl of 1×NEBuffer 3.1 (New England Biolabs). 60 fmol of target DNA was added and thoroughly mixed before placing the tube on 37° C. heat block for 1 min.

For in vitro cleavage kinetics measurements, 365 nm light was applied for time t=min(T, 30 sec), where T is the total incubation time of 1 sec, 5 sec, 10 sec, 30 sec, 1 min, 2 min, 5 min, 10 min, 20 min, 30 min. A no light control was allowed to incubate in 37° C. for 30 min. Immediately after time T, the reaction was quenched in 95° C. for 10 min. To evaluate light dosage effect, 365 nm light was applied for 1 sec, 5 sec, 10 sec, 30 sec, 1 min, 2 min before incubation at 37° C. for 30 min. After incubation, 10 μg of Proteinase K (Thermo Fisher) was added to each tube and further incubated in 55° C. for 15 min. The DNA was then purified with QIAquick PCR Purification Kit (Qiagen) before loading on an agarose gel for visualization.

For EMSA, a tube was incubated at 37° C. for 30 min and directly loaded on an agarose gel. 4% E-Gel EX Agarose Gels run on an E-Gel IBASE™ Power System (Thermo Fisher) were used for all in vitro experiments. To calculate cleavage efficiency, the integrated intensity of cleaved bands was divided by that of total DNA as quantified using ImageJ.

Plasmid and Retroviral Transduction

To clone the Cas9-EGFP plasmid, we replaced the dCas9-EGFP plasmid (Addgene #51023) with an active Cas9 component. For viral production, GP2-293 packaging cells were used and cultured on a 10 cm dish for overnight. Next day, 23 μg of transfer vector, 5 μg of pVSVg and 5 μg of pGag-Pol plasmids were transfected into the packaging cells using polyethylenimine (PEI). 8-12 h after transfection, the medium containing PEI was discarded and the cell culture was gently replenished with 15 ml of fresh DMEM medium. 48 h after transfection, 15 ml of virus was harvested and purified through a 0.45 μm filter.

Construction of Stable U-2 OS Cell Lines

To make stable U-2 OS cell lines expressing Cas9-EGFP, we infected WT U-2 OS cells with Cas9-EGFP retrovirus and enriched positive cells with puromycin selection for a week. Subsequently, a monoclonal cell line was selected with only 2 copies of Chromosome 3 and low expression of Cas9-EGFP. To introduce mCherry-53BP1, the Cas9-EGFP cells were further infected with mCherry-BP1 retrovirus (Addgene #19835) and cultured for a week. Finally, the cells expressing both Cas9-EGFP and mCherry-BP1 were selected by FACS.

Transient Transfection of cgRNA

To deliver cgRNA into living U-2 OS cells, we transiently transfected 15 pmol of pre-annealed cr:tracr cgRNA to one 6-well imaging dish using Lipofectamine RNAiMAX Transfection Reagent (Thermo Fisher Scientific). After 24 h incubation, Cas9-EGFP foci were easily detectable using epi-fluorescence microscopy. To target the repetitive region, the cells were transfected with 15 pmol of Ch3 cgRNA. To target single cleavage site, the cells were transfected with a mixture of 5 pmol of Ch3 (truncated 11mer) targeting the repetitive region and ~10 pmol of cgRNA targeting PPP1R2.

Single Particle Fluorescence Imaging of Living Cells

U-2 OS cells stably expressing Cas9-EGFP and 53BP1-mCherry were seeded onto glass coverslip and transfected with cgRNA for 24 h. To activate Cas9/cgRNA, the cell sample was illuminated with either custom 365 nm LED (30 s) or 405 nm laser (10 s) before imaging. A Nikon Ti-E fluorescence microscope equipped with two Andor EMCCDs was used for simultaneous imaging of Cas9 foci and 53BP1-mCherry foci, which were excited by 488 nm and 561 nm lasers, respectively. All live cell imaging experiments were performed at 37° C. and in L-15 media supplemented with 10% FBS and 1% Penicillin/Streptomycin.

Data Analysis

To analyze the time-course of 53BP1 recruitment, 'u-track' single-particle tracking algorithm was used (K. Jaqaman et al., Robust single-particle tracking in live-cell time-lapse sequences *Nature Methods* 5, pp. 695-702 (2008)) to precisely identify the centroid of Cas9-EGFP foci in each frame and linked these coordinates as the analysis trajectory. Next, the time-lapse trajectory was applied to the 53BP1-mCh channel and defined a squared area using the centroid coordinates of Cas9-EGFP, within which the intensity of 53BP1-mCh was measured. The final intensity trajectories in both Cas9-EGFP and 53BP1-mCh channels were compiled using a custom MATLAB package. The reported intensity trace of 53BP1-mCh was both background-subtracted and photobleaching-corrected.

Immunofluorescence Microscopy

U-2 OS cells stably expressing Cas9-EGFP cells were seeded onto glass coverslip and transfected with specific gRNAs for 12-24 h. After light stimulation, cell fixation was performed with 4% of paraformaldehyde in 1×PBS for 10 min and then quenched by 1×PBS supplemented with 0.1 M glycine for 10 min. After thoroughly rinsing with 1×PBS, 0.5% Triton-X was used to permeabilize cell membrane for 10 min. 2% w/v BSA in 1×PBS was used to passivate the sample for 1 h and at room temperature. Without further rinsing, primary antibody was diluted in 1×PBS and directly added into the chamber for targeting the protein of interests. After 1 h incubation, primary antibody was removed and the sample was thoroughly washed with 1×PBS three times. Secondary antibody was typically diluted in 1:1000 and applied to the sample for 1 h. Finally, the sample was rinsed three times and mounted with Prolong Diamond mounting media (Thermo Fisher Scientific) overnight.

Alexa647 and Alexa750 conjugated Goat anti-rabbit IgG (H+L) antibody (A21245, A21039) and Cy5 conjugated Goat anti-mouse antibody (A10524) were purchased from Thermo Fisher. Anti-MDC1 (Ab11169) and anti-Phospho-DNA-PKcs (S2056) (Ab124918) antibodies were purchased from Abcam (Cambridge, MA). Anti-53BP1 (NB100-304), anti-γH2Ax (NB100-384) and anti-MRE11 (NB100-473) were purchased from Novus Biologicals (Centennial, CO). Anti-Phospho-ATM (Ser1981) monoclonal antibody (10H11) (MA1-2020) was purchased from Thermo Fisher. Dilution of primary antibody was based on the recommended ratio from the manufacturers.

Results

To develop an inducible CRISPR system with rapid activation kinetics, the study herein focused on the molecular process of Cas9 cleavage regulation. The protospacer adjacent motif (PAM)-proximal ~9-10 bp region of guide RNA (gRNA) determines binding of *Streptococcus pyogenes* Cas9 (Cas9 henceforth) to its target DNA while additional base pairing at the PAM-distal region (10-20 bp) is required for cleavage (J. E. Dahlman, et al. Orthogonal gene knockout and activation with a catalytically active Cas9 nuclease. Real-time observation of DNA recognition and rejection by the RNA-guided endonuclease Cas9. *Nat. Biotechnol.* 33, 1159-1161 (2015); D. Singh, et al. *Nat. Commun.* 7, 12778 (2016)). Mismatches in the PAM-distal region prevent full unwinding of target DNA (D. Singh, et al. Mechanisms of improved specificity of engineered Cas9s revealed by single-molecule FRET analysis. *Nat. Struct. Mol. Biol.* 25, 347-354 (2018)) and conformational changes of the HNH domain (S. H. Stenberg, et al. Conformational control of DNA target cleavage by CRISPR-Cas9. *Nature.* 527, 110-113 (2015)) required for cleavage. Based on this mechanistic understanding, several uracils at the PAM-distal region of gRNA with light-sensitive, 6-nitropiperonyloxymethyl modified deoxynucleotide thymine (NPOM-dT) caged nucleotides (H. Lusic, et al. Photochemical DNA activation. *Org. Lett.* 9, 1903-1906 (2007)) to form a caged gRNA (cgRNA) (FIG. 1A). The Cas9/cgRNA complex retained the ability to search for and bind its target DNA, but not cleave because the steric hindrance imposed by the caging groups prevents full DNA unwinding and cleavage activation. Upon light stimulation at 365 or 405 nm, the caging groups were removed and the pre-bound, cleavage-deficient Cas9/cgRNA complex rapidly induced target DNA cleavage.

Figure 1B:
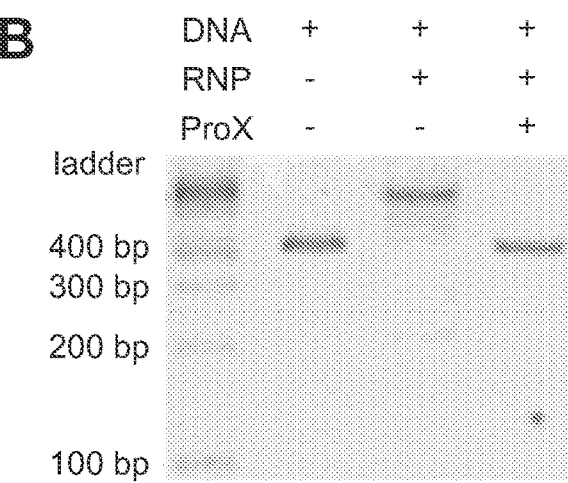
Figure 1C:
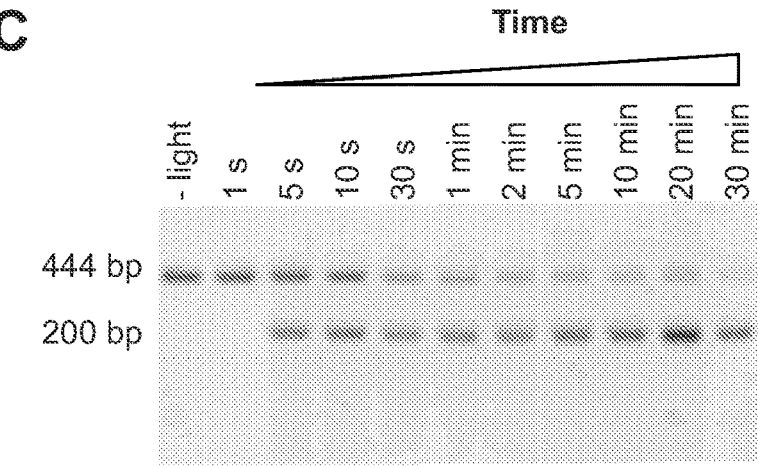
Figure 1D:
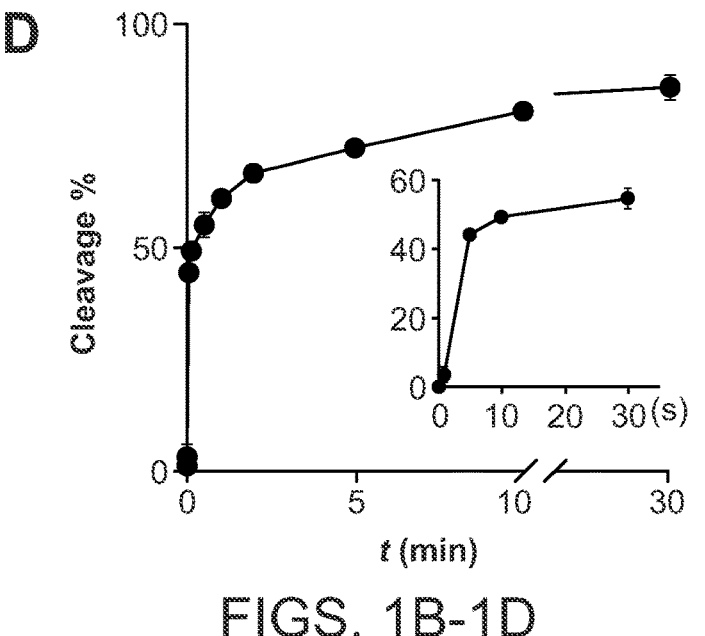
Figure 5A:
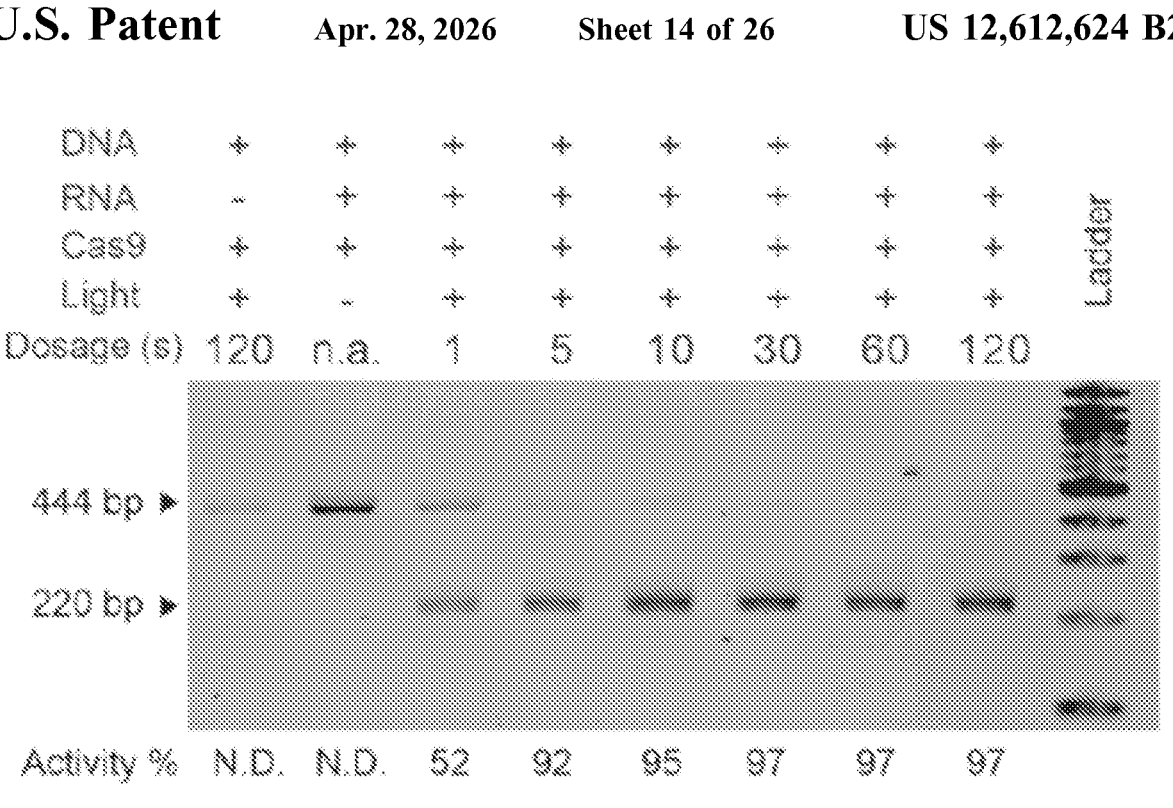
FIGS. 5A and 5B are an image of a blot and a graph demonstrating that the light-inducible cleavage activity of Cas9/cgRNA is dosage dependent.
Figure 5B:
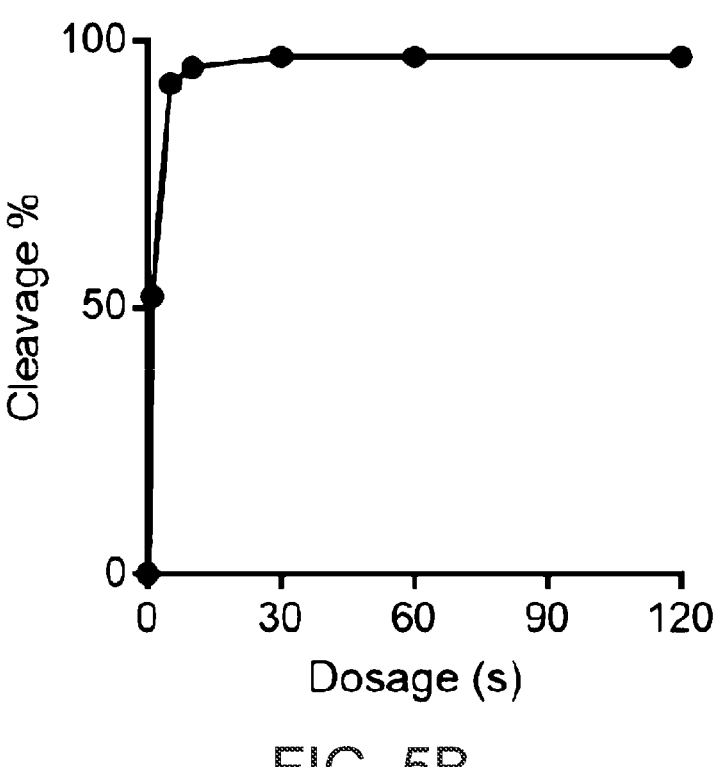

To determine if Cas9/cgRNA binds to target DNA, an electrophoretic mobility shift assay (EMSA) was performed on a 444 bp DNA target using Cas9/cgRNA that contains NPOM-dT at the $13^{th}$, $16^{th}$ and $17^{th}$ positions (FIG. 1B). Without light, Cas9/cgRNA stably associated with target DNA and caused a clear band shift. After proteinase K treatment, Cas9 was degraded and target DNA shifted back to the original position without any cleavage product. To test light-activated DNA cleavage, an in vitro cleavage assay (FIGS. 1C, 1D) was performed on the same target sequence. No cleavage product was detectable without light activation, while 45% of cleaved DNA products 218 and 226 bp in size appeared only 5 seconds after the onset of light illumination (Jaxman, 365 nm, ~40 mW/cm$^2$), rising to over 80% after 10 minutes. Dosage-dependent assay further confirmed that cleavage activity saturated with 10-30 s of light stimulation (FIGS. 5A, 5B). Collectively, these in vitro experiments demonstrate that the Cas9/cgRNA complex binds well to DNA in the dark and exhibits very fast and efficient cleavage within seconds after uncaging.

Figure 2A:
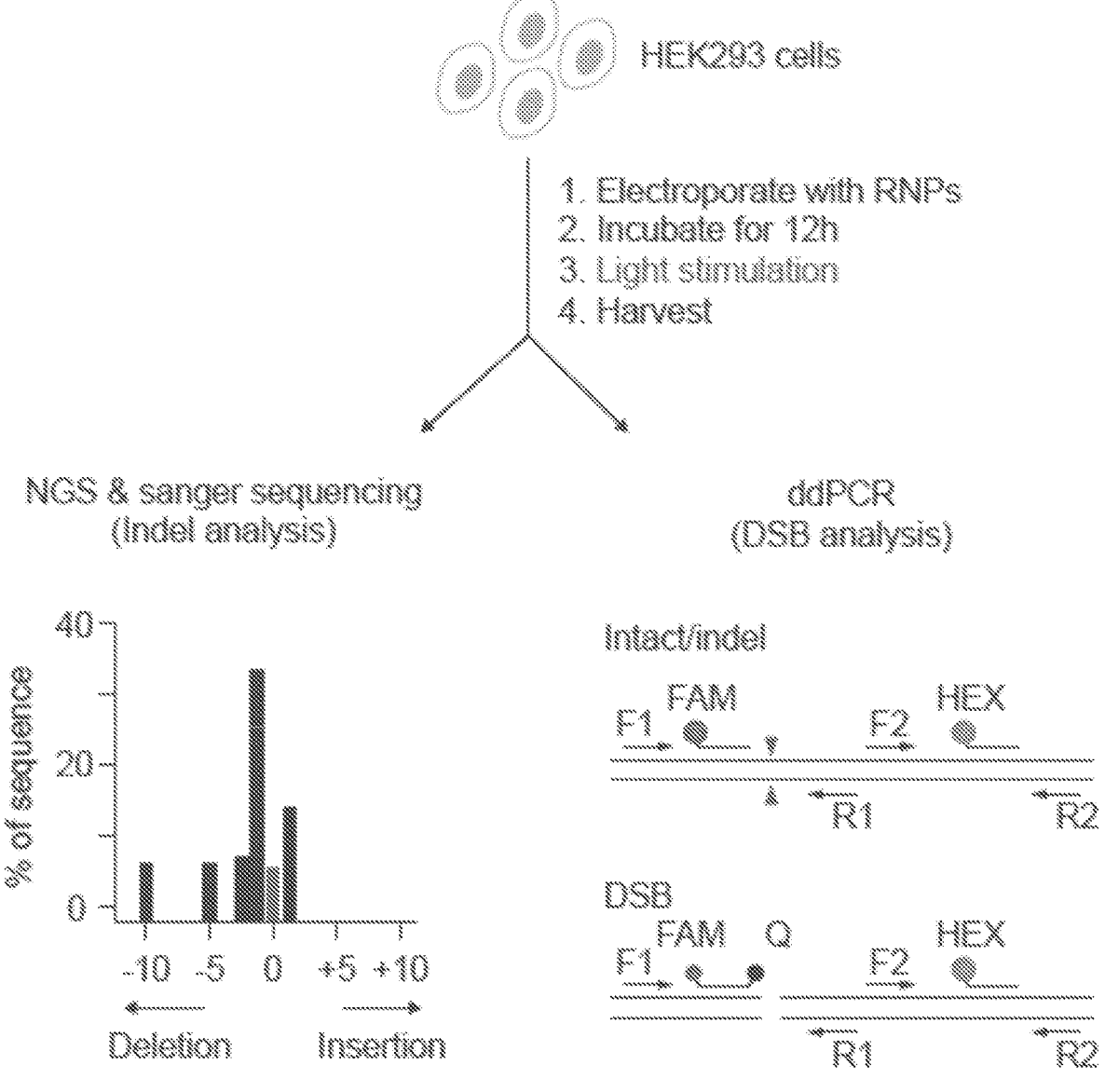
FIGS. 2A-2E are a series of schematics and graphs demonstrating that Cas9/cgRNA is very fast and efficient in cells, cleaving both genomic DNA targets and mutagenic indels.
Figures 2B, 2C, 2D, 2E:
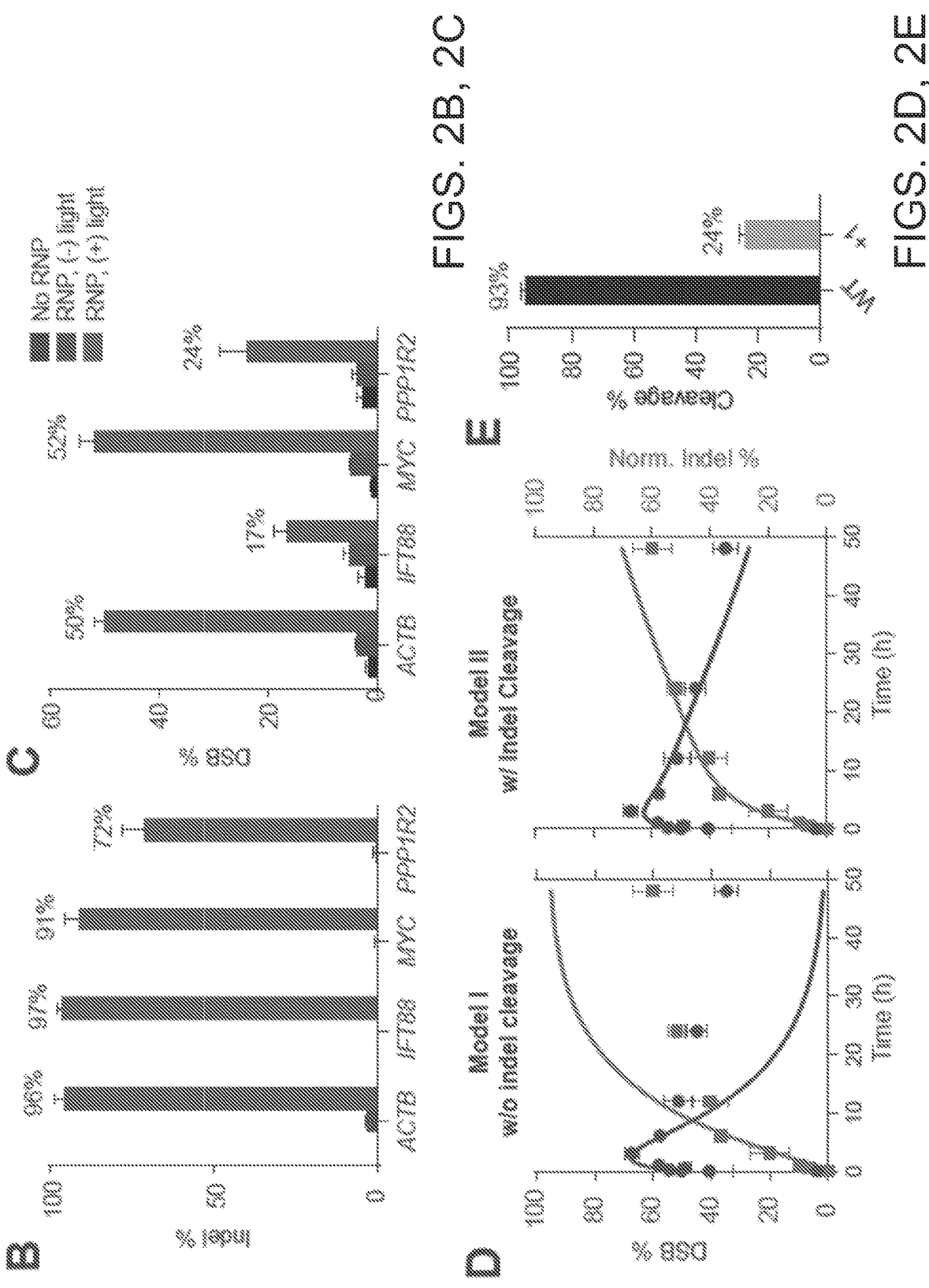
Figures 6A, 6B:
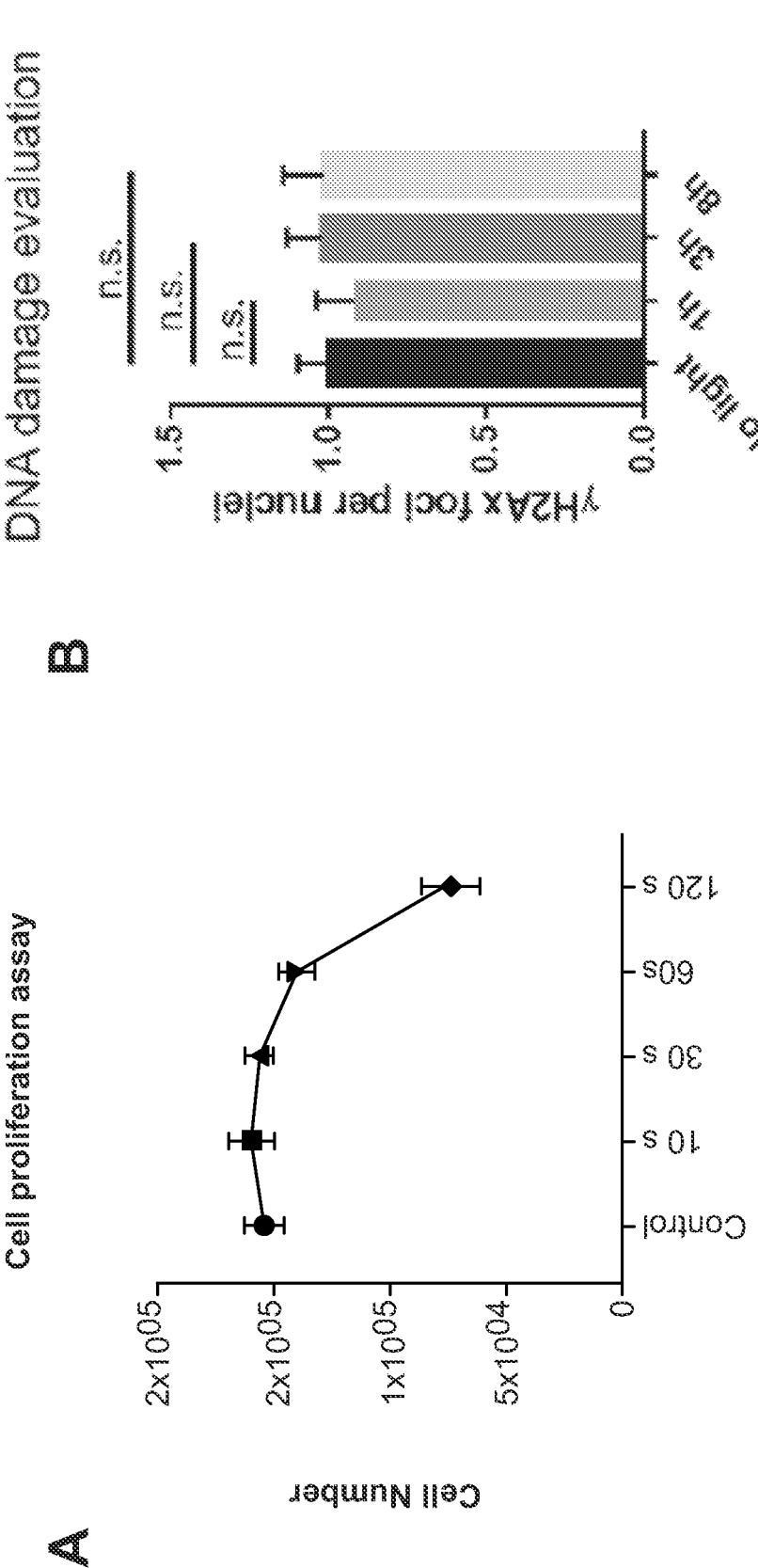
FIGS. 6A, 6B are graphs showing the measurement of phototoxicity induced by 365 nm light. Cell proliferation assay were performed on HEK293T and U-2 OS cells after stimulation with 365 nm light of different dosages (seconds of exposure at equal light power).
Figure 7A:
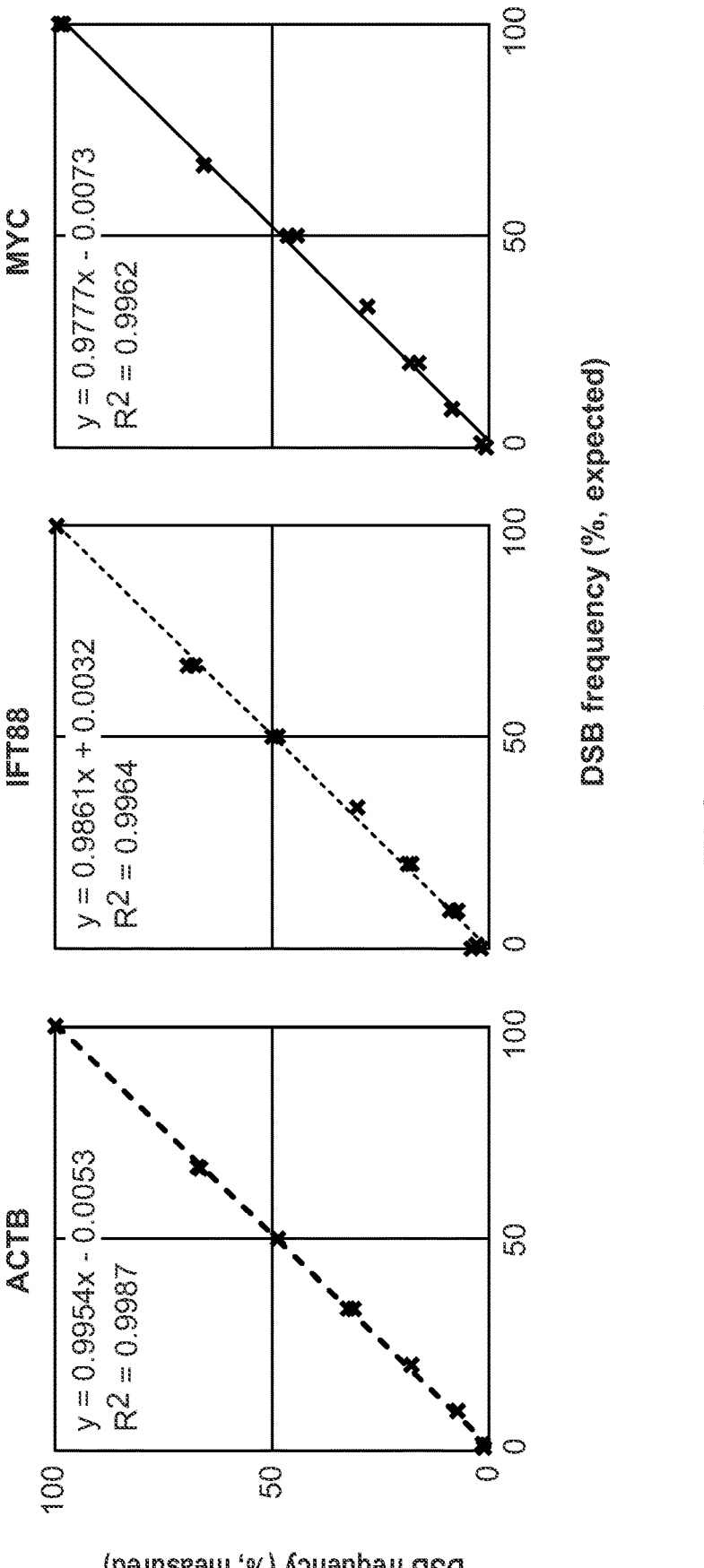
FIGS. 7A and 7B are plots demonstrating that DSB-ddPCR accurately reports the percentage of DNA cleavage.
Figure 7B:
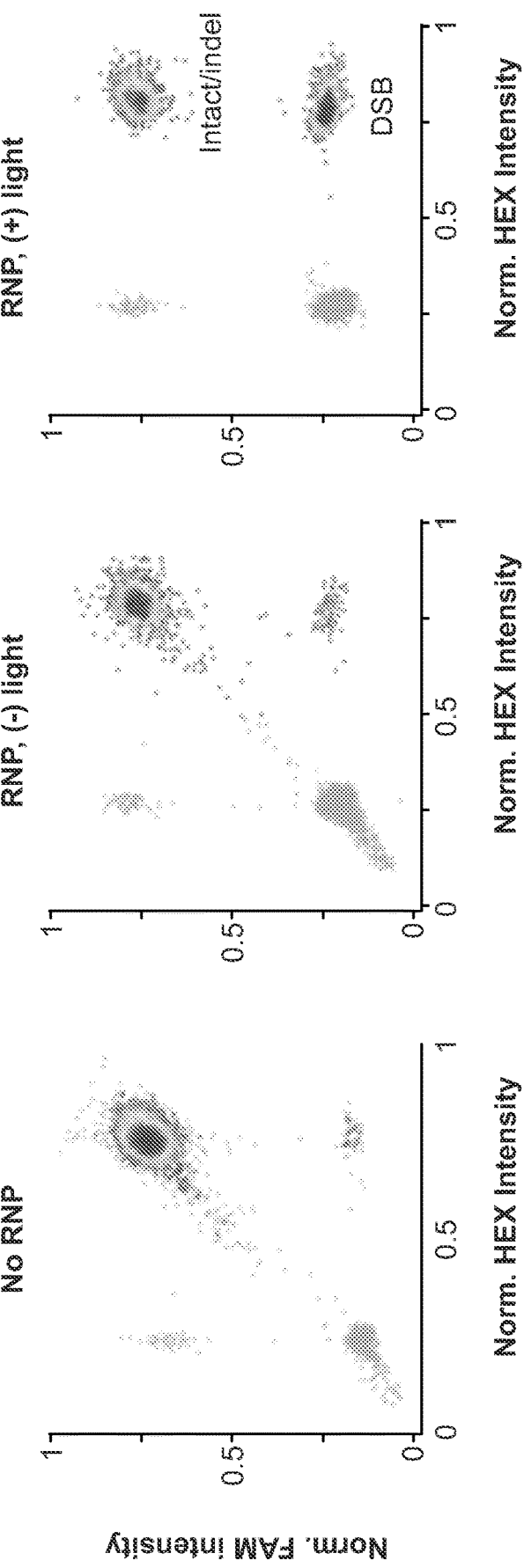
Figure 8A:
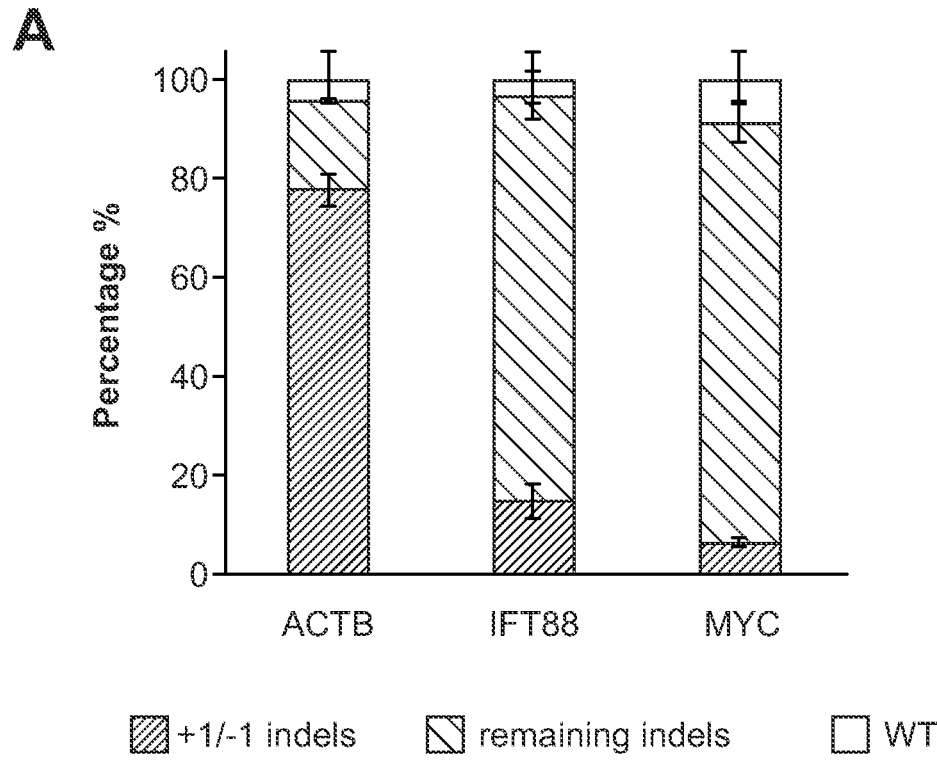
FIGS. 8A-8D are a series of graphs, images and a sequence of an in vitro cleavage assay showing Cas9 cleavage of +1/−1 indel products.
Figure 8B:
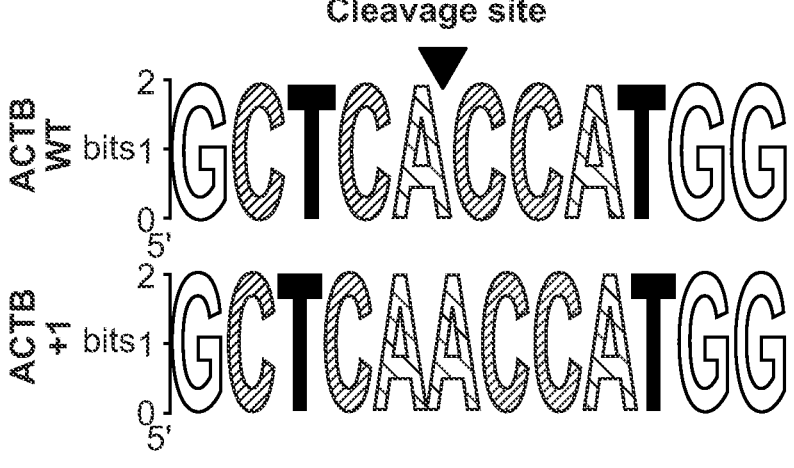
Figure 8C:
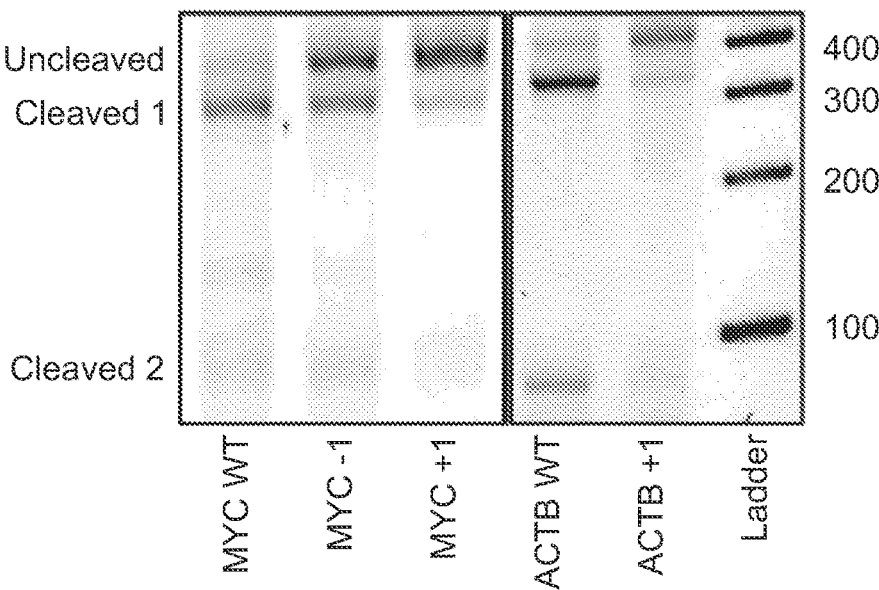
Figure 8D:
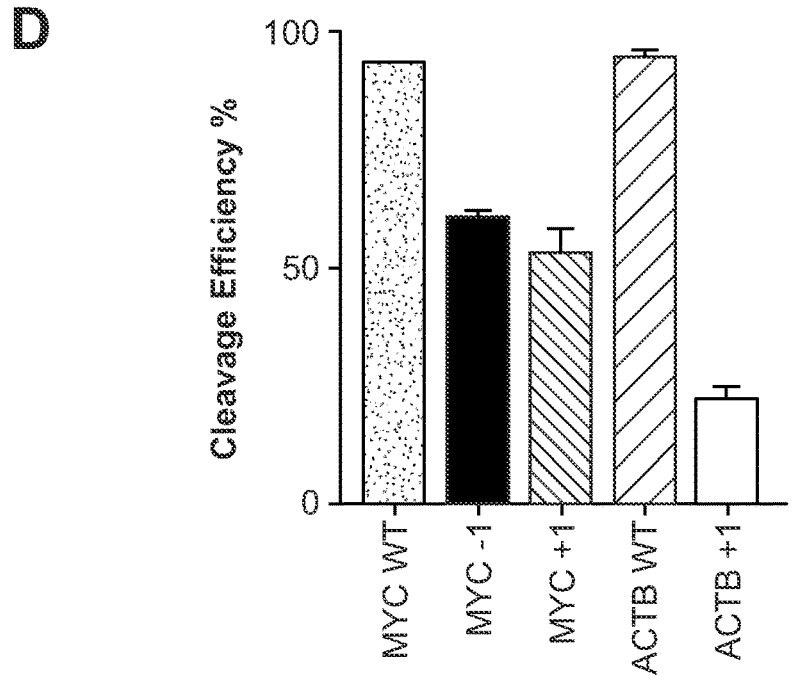

Next, the kinetics of light-induced Cas9 activity in mammalian cells were characterized. Pre-assembled Cas9/cgRNA ribonucleoproteins (RNPs) were electroporated into human embryonic kidney 293 cells (HEK293T) and incubated for 12 h to allow RNPs to bind their DNA targets. After light stimulation (365 nm, 30 s), genomic DNA was extracted at various time points for further analysis (FIG. 2A). With this dosage of light, neither cell growth arrest nor additional DNA damage foci was detected (FIGS. 6A, 6B). Droplet Digital PCR (ddPCR) was used to quantify the amount of DSBs (FIGS. 7A, 7B) (J. C. Rose et al., Rapidly inducible Cas9 and DSB-ddPCR to probe editing kinetics. *Nat. Methods.* 14, 891-896 (2017)) and a combination of Sanger sequencing-based TIDE (Tracking of Indels by Decomposition) analysis and targeted deep sequencing to measure insertions and deletions (Indels) (E. K. Brinkman et al., Easy quantitative assessment of genome editing by sequence trace decomposition. *Nucleic Acids Res.* 42, e168 (2014)) at four genomic loci: ACTB, IFT88, MYC, and PPP1R2. The system herein, exhibited highly efficient on-target editing with light and near-zero basal activity without light. 48 h after light stimulation, >90% indels were detected for ACTB, IFT88, and MYC, and 72% indels for PPP1R2 among the PCR-amplifiable DNA, while cells without light exposure had almost no detectable indels (FIG. 2B). Furthermore, this system is very fast. The DSB-ddPCR assay detected cleavage of a significant fraction of target genomic DNA within 30 s after light activation, ranging from 17% to 24% for IFT88 and PPP1R2, and 50% to 52% for ACTB and MYC (FIG. 2C). Without light, the DSB-ddPCR assay did report a small increase in DSB above baseline, but that did not translate to any detectable indels for three out of the four loci tested.

Figures 9A, 9B:
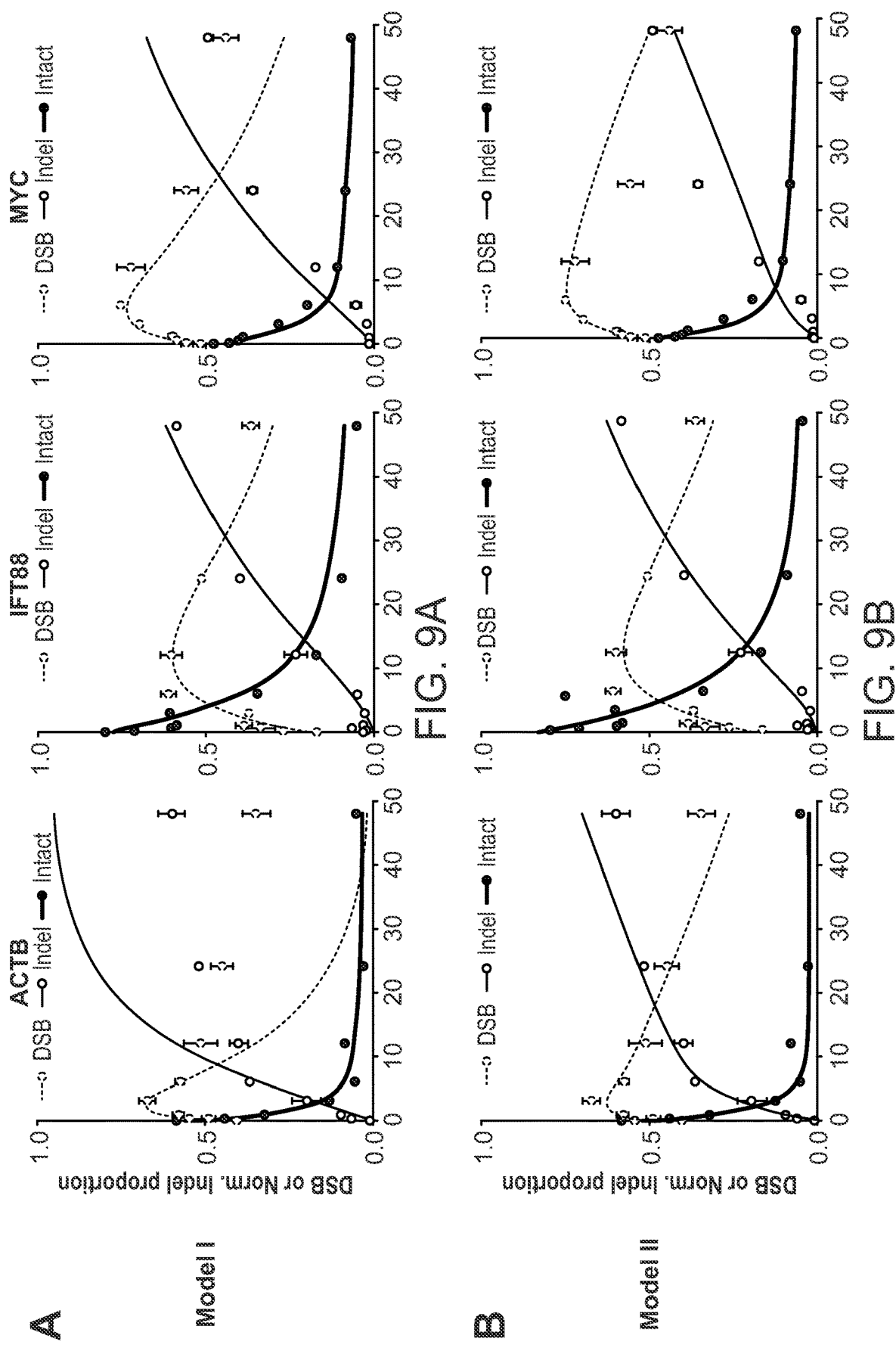
FIGS. 9A-9D are a series of graphs and plots demonstrating the kinetic modeling of Cas9-induced DSB and indel formation. DNA repair Model II which factors in re-cleavage of indel ($k_{re}$) (See, Example 2 for description). Pairs of ordinary differentiation equations were used to fit the data here and in FIG. 2D. Cas9/cgRNA RNPs targeting 3 different loci were electroporated into HEK293T cells respectively. Light stimulation occurred 12 h after electroporation, and genomic DNA was harvested at multiple time points after light stimulation. ddPCR and TIDE analysis were used to quantify the percentage of DSB and indels as a function of time. The data were fit simultaneously with the two equations in Model II using custom MATLAB code. The percentages of DSBs, normalized indels, and intact DNA are shown in blue, red, and gray respectively. The normalized indel percent here is defined by the percent of total DNA at each locus with indels (factoring in cleaved DNA that cannot be amplified and detected by Sanger sequencing). Norm. Indel %=Indel %×(100−DSB %)/100. Intact %=100−Indel %−DSB % (the sums of DSB %, Normalized Indel % and Intact % equals 100%) (A) Fitting data with Model I. Round circles indicate collected data points, lines indicate fitting to model. n=3, error bars indicate standard deviations.
Figures 9C, 9D:
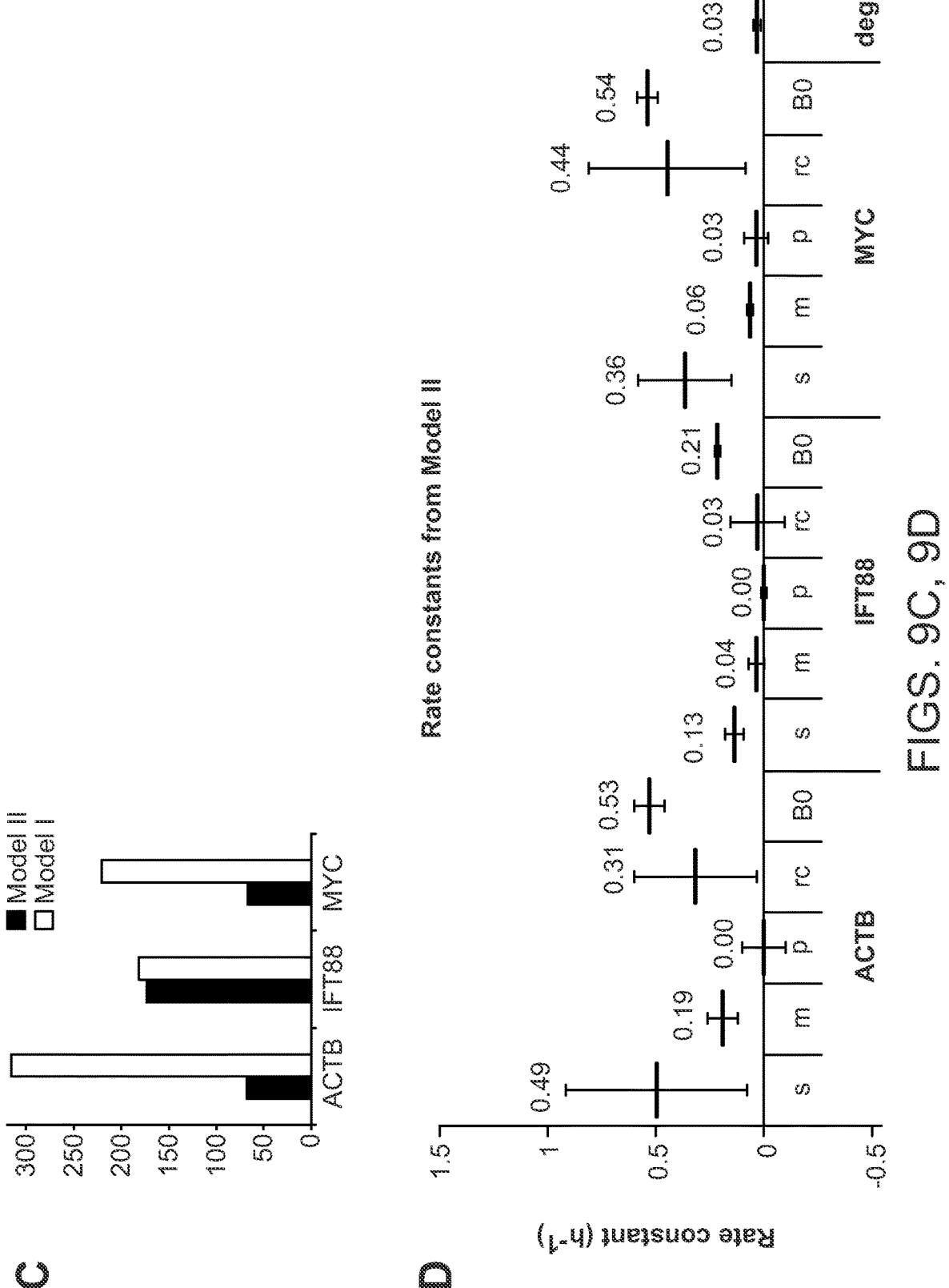

Utilizing the precisely defined time for cleavage, the target searching, cleavage, and repair kinetics of Cas9-mediated DSBs was investigated by harvesting genomic DNA from electroporated cells at various time points after light activation. FIG. 2D shows the time courses for percentages of DSBs and normalized indels at the ACTB locus after light activation at t=0. ~50% of DSBs were detected already at t=30 s, likely due to pre-bound Cas9/cgRNA which rapidly cleaves its target. DSB continues to increase to ~70% over 3 hours, which was attributed to the recruitment of previously unbound, now activated Cas9/cgRNA. DSBs then decrease as indels begin to appear. To describe the DNA repair process, a mathematical model previously used to describe the kinetics of DSB and indel formation simultaneously was adopted (E. K. Brinkman et al., Kinetics and Fidelity of the Repair of Cas9-Induced Double-Strand DNA Breaks. *Mol. Cell.* 70, 801-813.e6 (2018)). Because an indel would have mismatch(es) against the PAM-proximal region of gRNA, it was first assumed that an indel cannot be recut (E. K. Brinkman et al., 2018) (Model I, Example 2). This initial model predicted a near complete depletion of DSB due to its conversion to indels by 48 h, which failed to fit the data since nearly 40% of DSBs persist even after 48 h, although over 90% of PCR-amplifiable genomic DNA already contains indels at 24 h (FIG. 2D). This prompted a reexamination of the model assumptions. It was noticed that over 70% of the indels formed at the ACTB locus were single 'A' insertions at the cleavage site (FIG. S4A,B). With a new assumption that mismatched indel DNA can also be cleaved by Cas9 (Model II, Example 2), the model fits the data well with an apparent cleavage rate of ~0.31 h-1 for indels compared to an apparent cleavage rate of ~0.49 h-1 for perfectly-matched target DNA (FIG. 9D). Model II was also superior to Model I in fitting the DSB and indel time courses for two additional genomic loci, IFT88 and MYC (FIGS. 9A-9C). Indeed, in vitro cleavage assays using wild type gRNA on synthetic DNA fragments of the genomic DNA sequence that includes the gRNA targeting site for ACTB, with or without the +1 'A' insertion, confirmed significant cleavage of +1 insertion DNA, although at a lower efficiency compared to the wild-type sequence (FIG. 2E and FIGS. 8A-8D). Similar re-cutting of +1/−1 indels was observed for MYC locus in the in vitro cleavage assays (FIGS. 8A-8D).

Figure 3A:
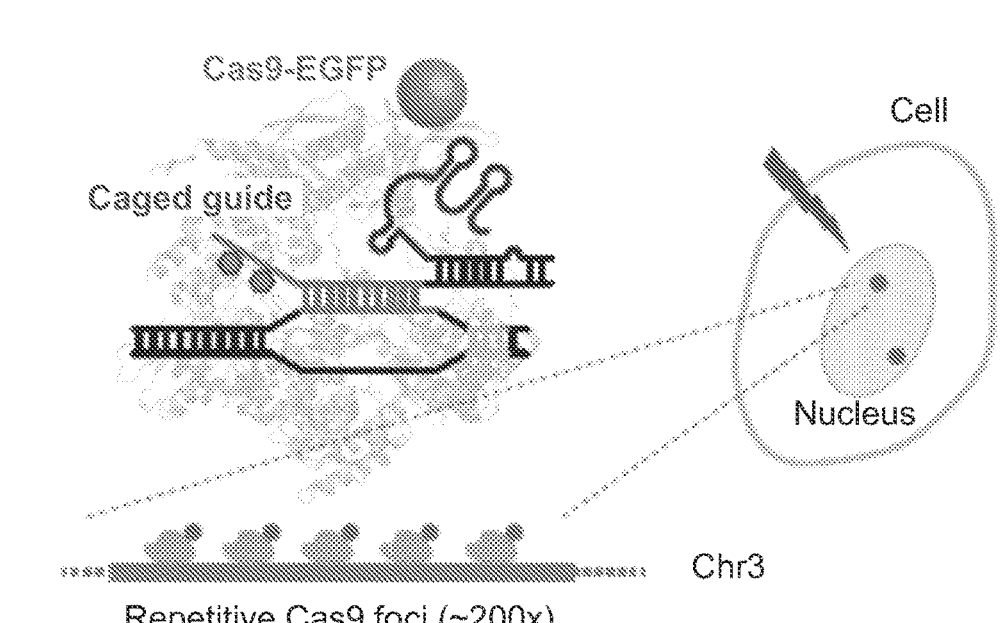
Figure 3B:
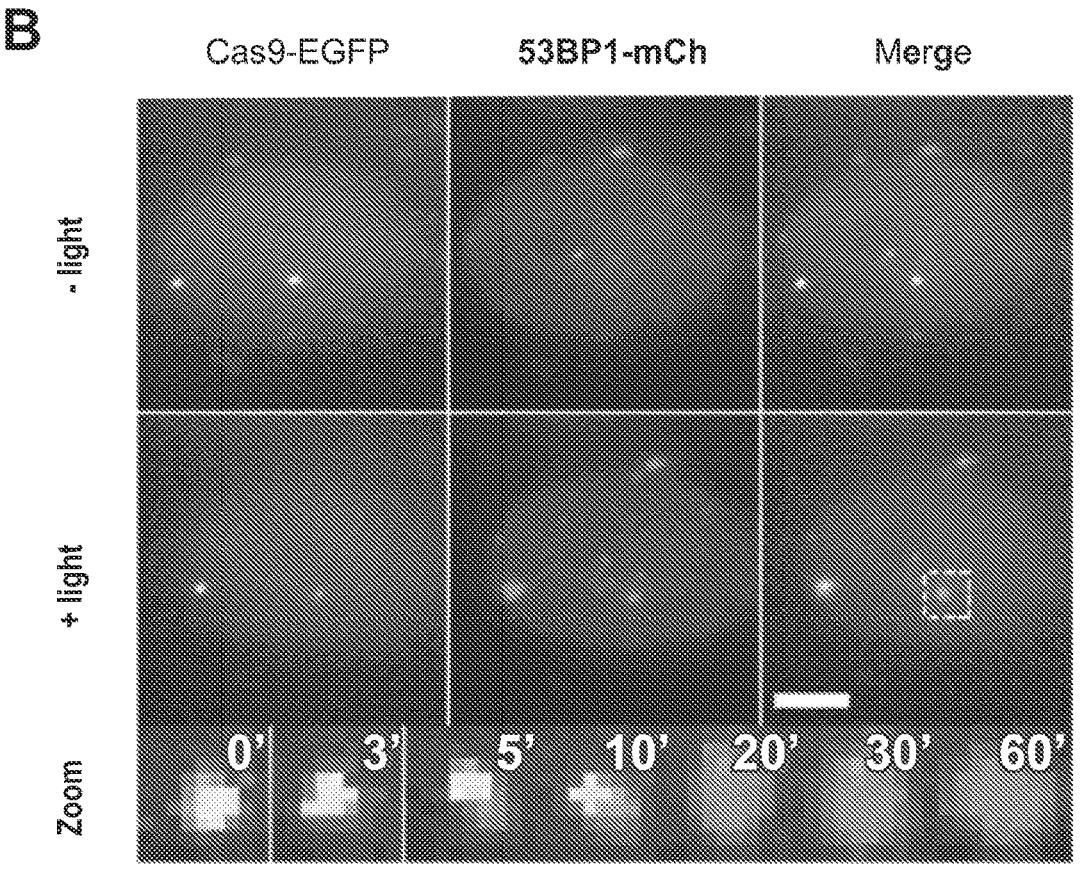
Figure 10:
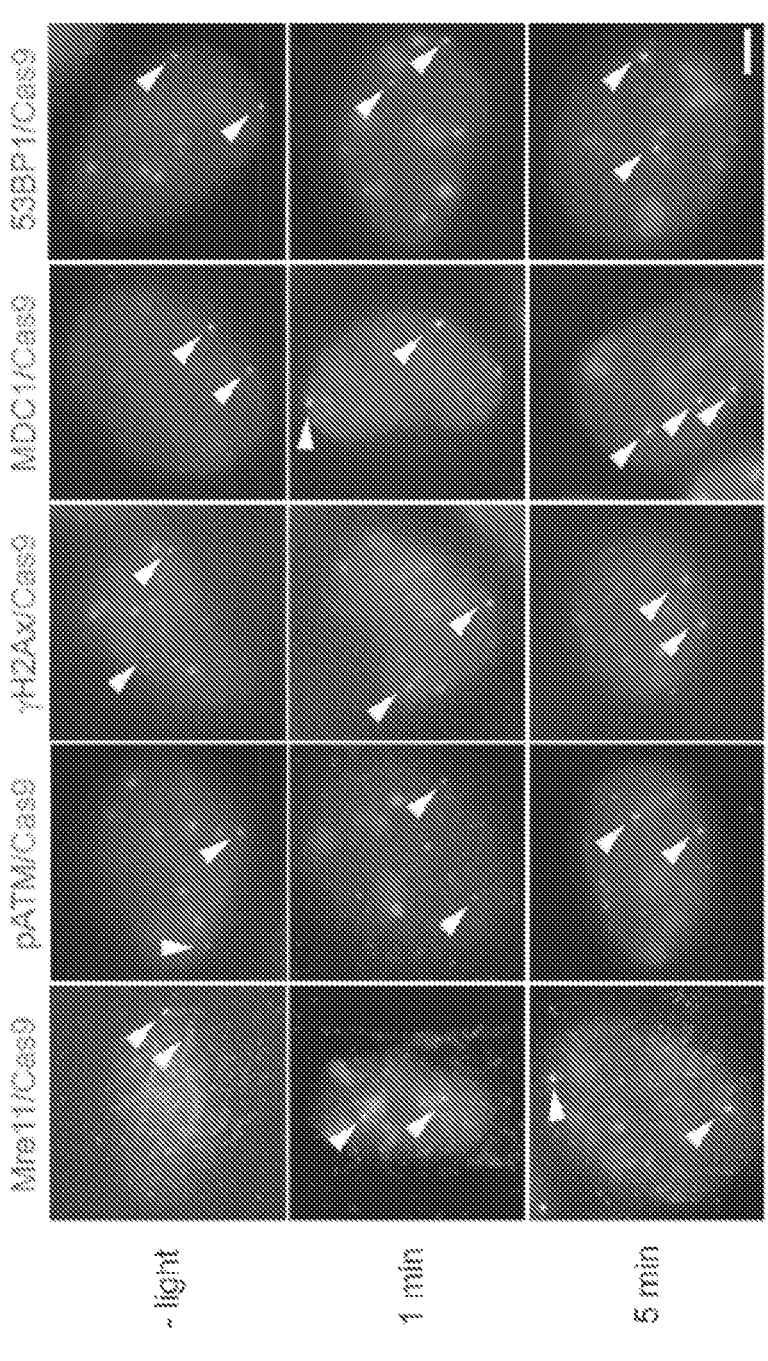
FIG. 10 is a series of images demonstrating that multiple DNA damage response proteins are recruited to the Cas9 foci within 1-5 min after activation. Cas9 in cells were activated with light, then fixed with paraformaldehyde 1 minute and 5 minutes after activation. Fluorescence microscopy was used to visualize the colocalization between the endogenous DDR proteins Mre11, phosphorylated ATM, MDC1, gH2Ax and 53BP1 via immunofluorescence (red, Cy5) and Cas9 (green, GFP) at the repetitive chromosome 3 locus Ch3rep.

In vitro experiments have shown that Cas9 remains bound to DNA after cleavage (S. H. Sternberg et al., DNA interrogation by the CRISPR RNA-guided endonuclease Cas9. *Nature.* 507, 62-67 (2014); C. D. Richardson et al., Enhancing homology-directed genome editing by catalytically active and inactive CRISPR-Cas9 using asymmetric donor DNA. *Nat. Biotechnol.* 34, 339-344 (2016); M. D. Newton et al. DNA stretching induces Cas9 off-target activity. *Nat. Struct. Mol. Biol.* 26, 185-192 (2019)), but many questions remain. When does Cas9 dissociate from DNA after cleavage in vivo? How quickly do cells sense the damage and deploy DDR proteins to the cleavage site? By providing a precise time point of DNA cleavage, the very fast CRISPR/Cas9 system allows for the dissection of the sequence of events in sensing and repairing of Cas9-induced DNA breaks. The strategy herein combines caged gRNA with Cas9-EGFP to visualize the genomic locus of interest (B. Chen et al., Dynamic imaging of genomic loci in living human cells by an optimized CRISPR/Cas system. *Cell.* 155, 1479-1491 (2013)) and enable light-initiated DNA cleavage. We delivered cgRNA targeting a repetitive region in chromosome 3 with over 200 Cas9 binding sites (Ch3rep) ( H. Ma et al., Multiplexed labeling of genomic loci with dCas9 and engineered sgRNAs using CRISPRainbow. *Nat. Biotechnol.* 34, 528-530 (2016)) into U-2 OS cells stably expressing a low level of Cas9-EGFP (FIG. 3A). The cells also expressed mCherry fused to a DNA damage response marker, P53 Binding Protein 1 (53BP1), to decorate DNA regions under repair (N. Dimitrova et al., 53BP1 promotes non-homologous end joining of telomeres by increasing chromatin mobility. *Nature.* 456, 524-528 (2008); K. Karanam et al., Quantitative Live Cell Imaging Reveals a Gradual Shift between DNA Repair Mechanisms and a Maximal Use of HR in Mid S Phase. *Mol. Cell.* 47, 320329 (2012)). Cleavage-deficient Cas9/cgRNA complexes formed two bright spots (green), representing both Ch3rep loci, and they did not colocalize with 53BP1-mCherry before uncaging (FIG. 3B). After uncaging, 53BP1-mCherry was specifically and primarily recruited to Cas9-EGFP foci within 5 minutes and as early as 1 minute (FIGS. 3C, 3D). Further, immunofluorescence showed that endogenous DNA damage responders such as ATM, 53BP1, MDC1, Mre11, and γH2Ax also accumulate to the Cas9-EGFP foci within 5 minutes (FIGS. 3E, 10).

Figure 11A:
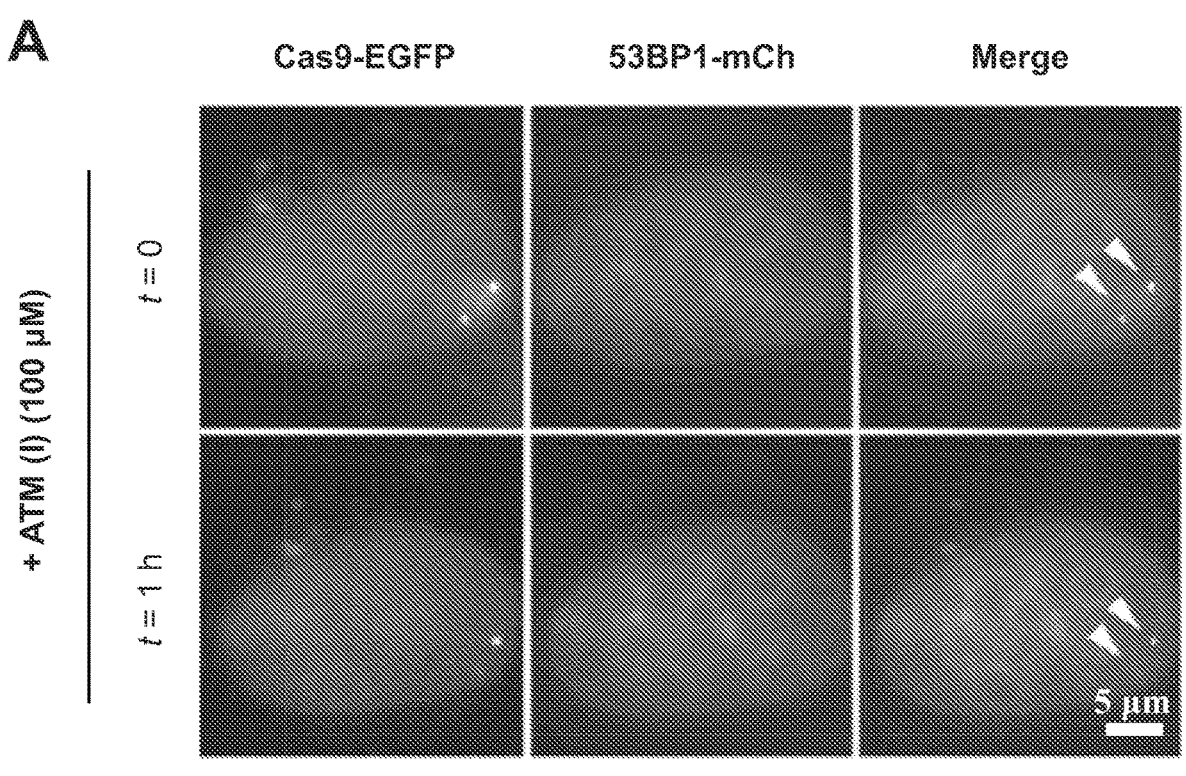
FIGS. 11A and 11B are a series of images and a graph demonstrating that inhibition of ATM kinase activity suppresses 53BP1 foci formation and delays Cas9 disappearance.
Figure 11B:
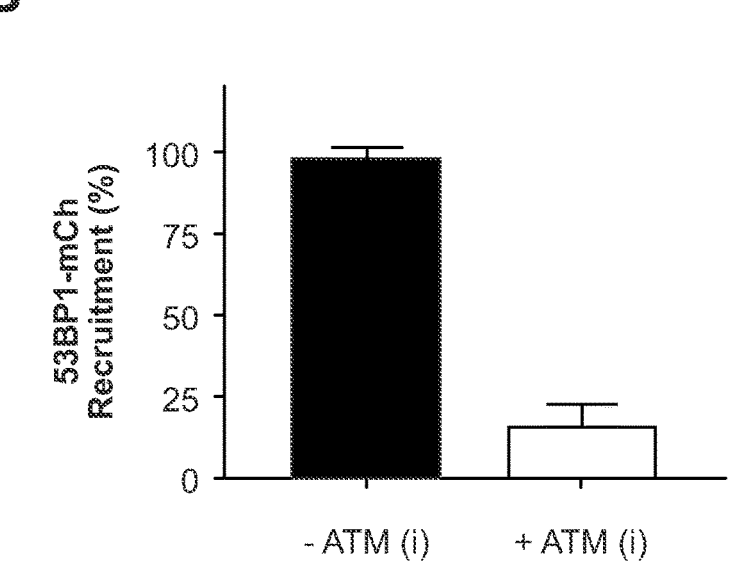
Figure 12A:
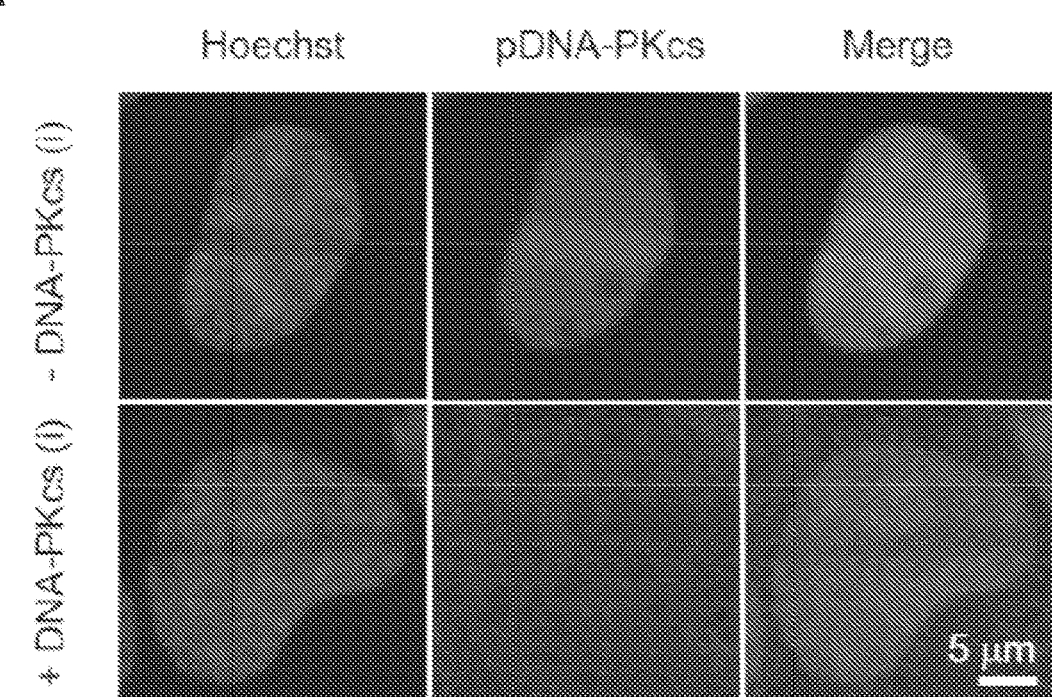
FIGS. 12A-12C are a series of images and a plot demonstrating that inhibition of DNA-PKcs does not influence 53BP1 recruitment at the Cas9 foci.
Figure 12B:
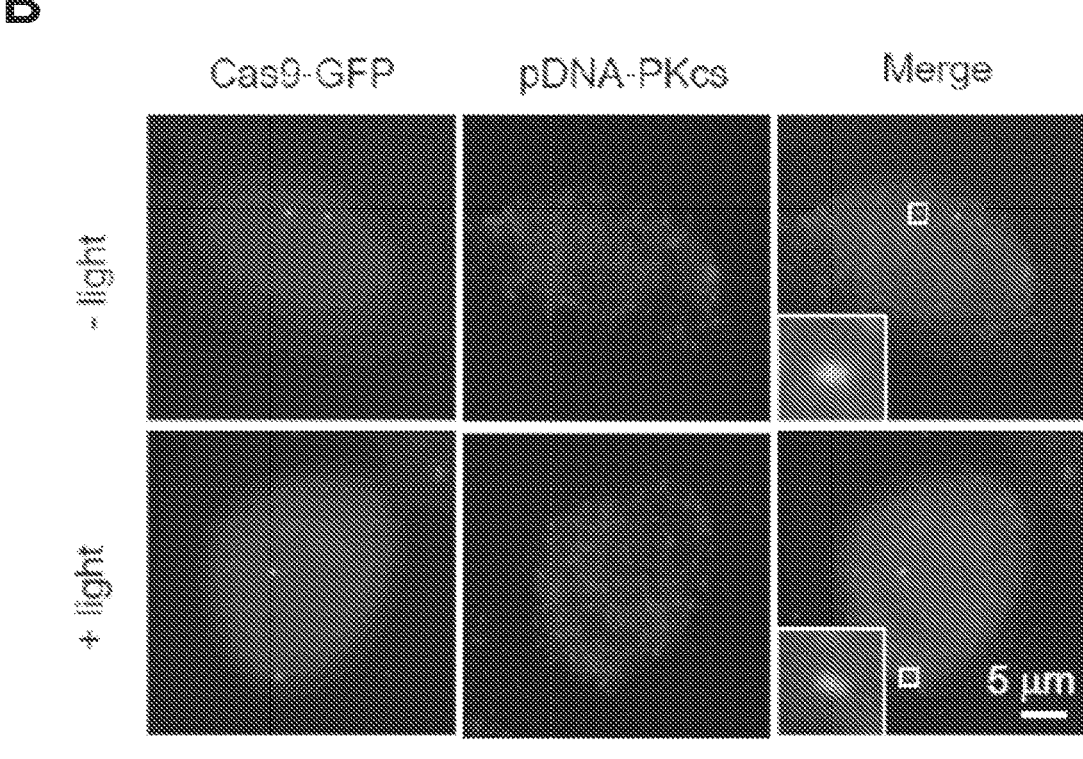
Figure 12C:
Figure 12C:
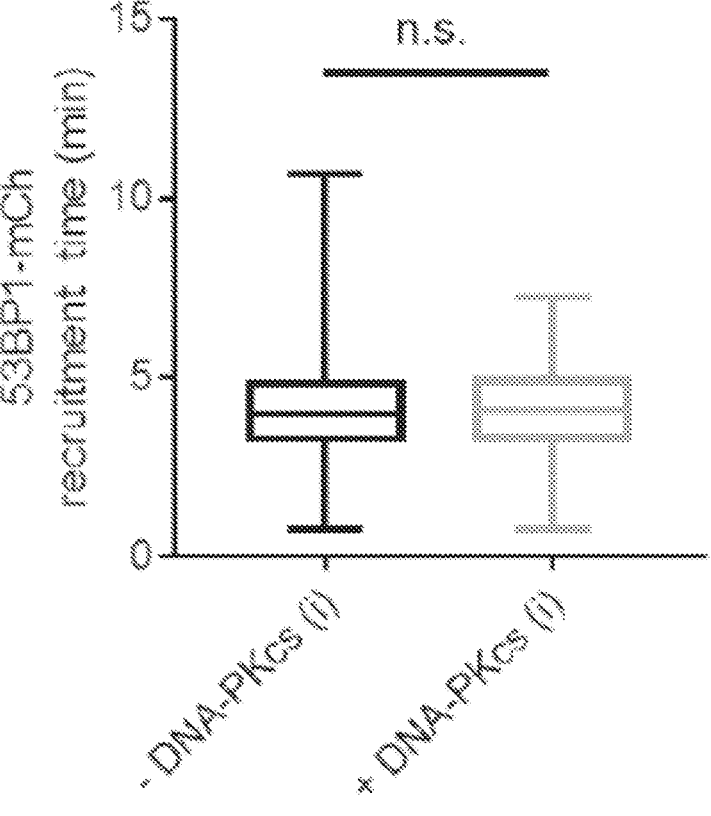

Notably, Cas9-EGFP spots gradually diminished and/or fragmented following 53BP1-mCherry recruitment (FIG. 3B). To study whether DDR activity is responsible for Cas9 dissociation, U-2 OS cells were pretreated with ATM inhibitor KU-55933 (100 μM, 1 h). Strikingly, 53BP1-mCherry foci formation was almost abolished and after 1 hour, 68% of the Cas9 foci remained compared to 19% without inhibitor (FIGS. 3F, 11A, 111B). In contrast, inhibition of DNA-Pkcs activity, another major DDR signal for DSB repair, did not appear to alter the kinetics of Cas9 foci disappearance nor of 53BP1-mCherry arrival (FIGS. 3F, 12A-12C). Together, these findings provide evidence that ATM kinase plays a predominant role in orchestrating the DDR process at Cas9-generated DSBs.

Figures 3G, 3H:
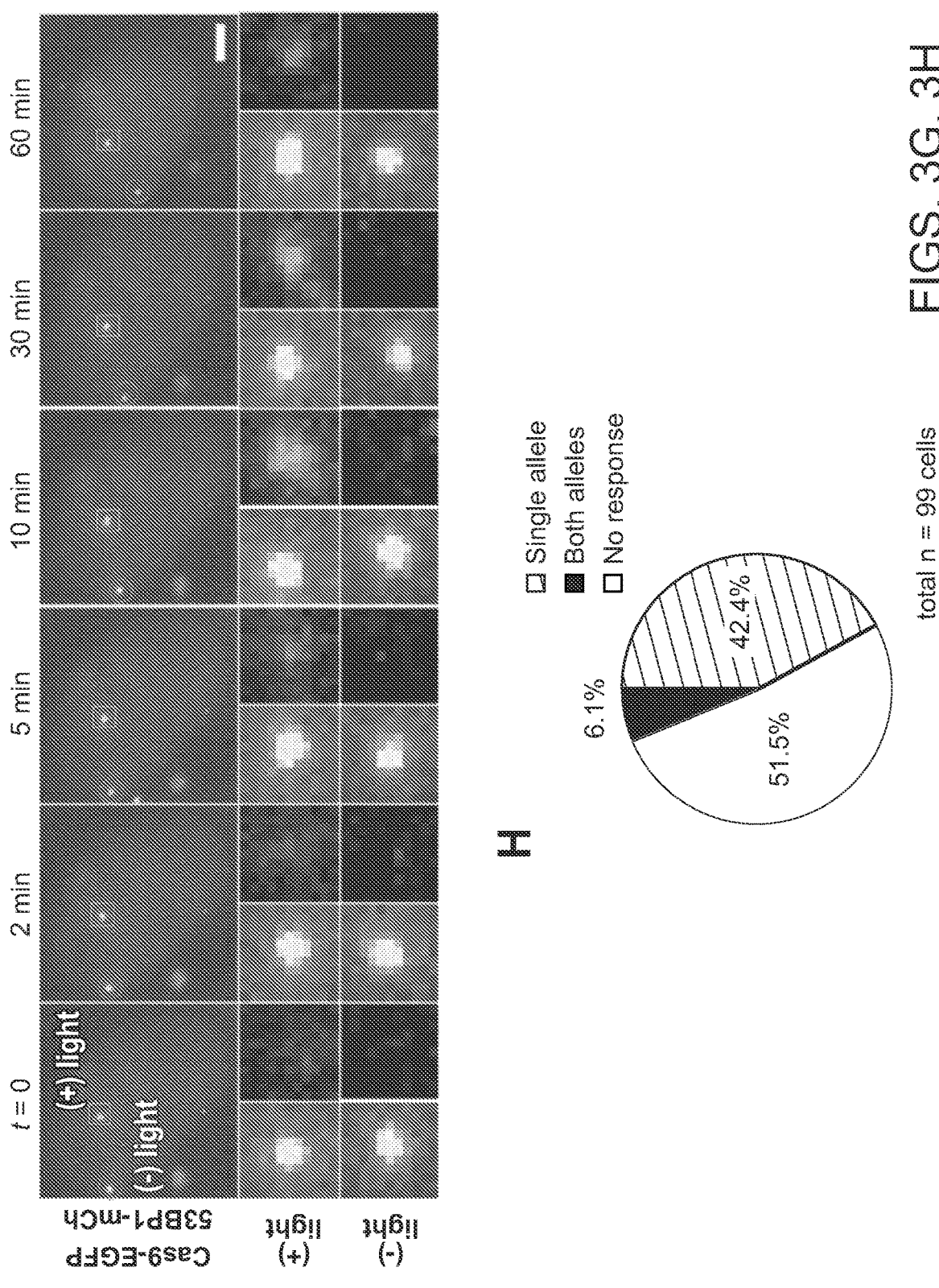
Figure 13:
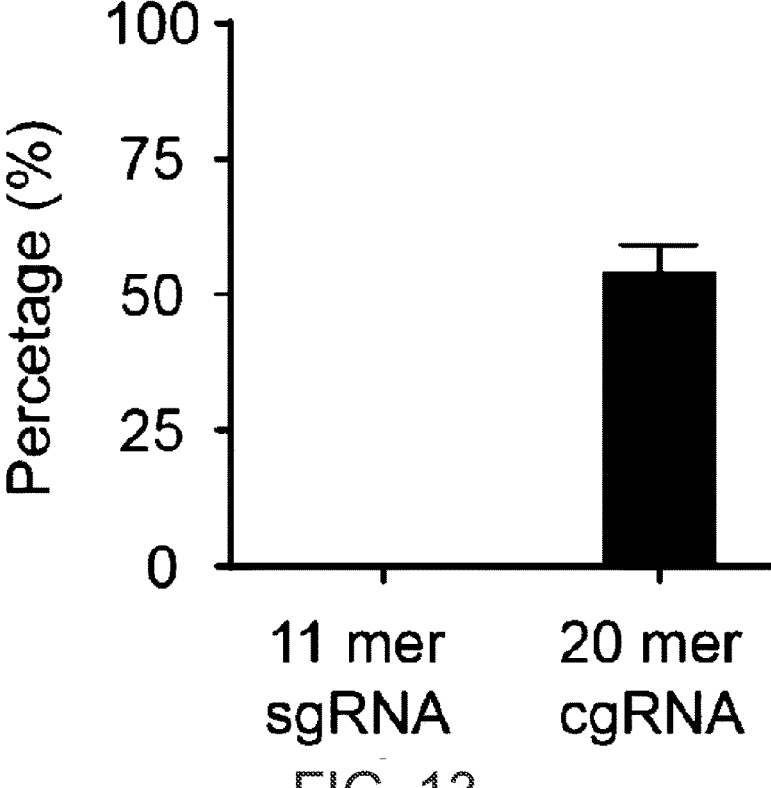
FIG. 13 is a graph demonstrating that truncated sgRNA and 405 nm focused laser do not lead to 53BP1-mCh recruitment at the Ch3rep locus in single allele stimulation. No 53BP1-mCh focus was observed when using 11mer truncated sgRNA versus over 50% recruitment using 20mer light-inducible and cleavage-competent cgRNA. This control experiment demonstrates that the 53BP1-mCherry is dependent on Cas9 cleavage and not due to the light itself.

Next, the ability of very fast CRISPR to create DSBs at a single allele was tested (FIG. 3G). Using fluorescence imaging as a guide, only one of the two alleles in each cell was illuminated with a focused uncaging laser beam (405 nm, 75 nW, 10 s). Rapid 53BP1-mCherry recruitment occurred at the illuminated allele (magenta square) preferentially over the non-illuminated allele (cyan circle) with a single allele specificity of ~90% (FIG. 3H). The DDR is mediated by Cas9 cleavage and not due to the laser itself because no 53BP1 recruitment was observed for cells with a truncated 11 mer gRNA compared to 48.5% 53BP1 recruitment to the illuminated alleles in cells with Cas9/cgRNA (FIG. 13). Overall, the data on cleavage activation at a single allele demonstrated an unprecedented level of temporal and spatial genomic manipulation.

In the live cell imaging scheme of Ch3rep where DDR protein recruitment was observed within 1 min of light activation, any one of the potentially >200 activated Cas9 bound to the repetitive region could initiate the DNA damage response. Therefore, an upper limit of ~200 min was placed as the time it takes for a single Cas9-mediated DSB to be detected. An unresolved question is how fast a single Cas9-induced DSB is detected and processed by the cellular repair machinery. Several in vitro experiments have suggested that Cas9 adopts a long-lived post-cleavage bound state on the genomic DNA (S. H. Sternberg et al., DNA interrogation by the CRISPR RNA-guided endonuclease Cas9. *Nature.* 507, 62-67 (2014); C. D. Richardson et al., Enhancing homology-directed genome editing by catalytically active and inactive CRISPR-Cas9 using asymmetric donor DNA. *Nat. Biotechnol.* 34, 339-344 (2016)). RNA polymerase, but not DNA polymerase activity, promotes the dislodging of Cas9 from its cleavage site and exposure of DSBs (R. Clarke et al., Enhanced Bacterial Immunity and Mammalian Genome Editing via RNA-Polymerase-Mediated Dislodging of Cas9 from Double-Strand DNA Breaks. *Mol. Cell.* 71, 42-55.e8 (2018); K. Whinn et al., Nuclease dead Cas9 is a programmable roadblock for DNA replication. bioRxiv, 455543 (2018)). In contrast, atomic force microscopy (AFM) experiment suggested that the DNA cleavage product may be released from the PAM side within a few minutes (M. Shibata et al., Real-space and real-Time dynamics of CRISPR-Cas9 visualized by high-speed atomic force microscopy. *Nat. Commun.* 8, 1430 (2017)). Here, this question is directly addressed by monitoring the dynamics of 53BP1-mCherry recruitment induced by cleavage at a single genomic site.

Figure 4A:
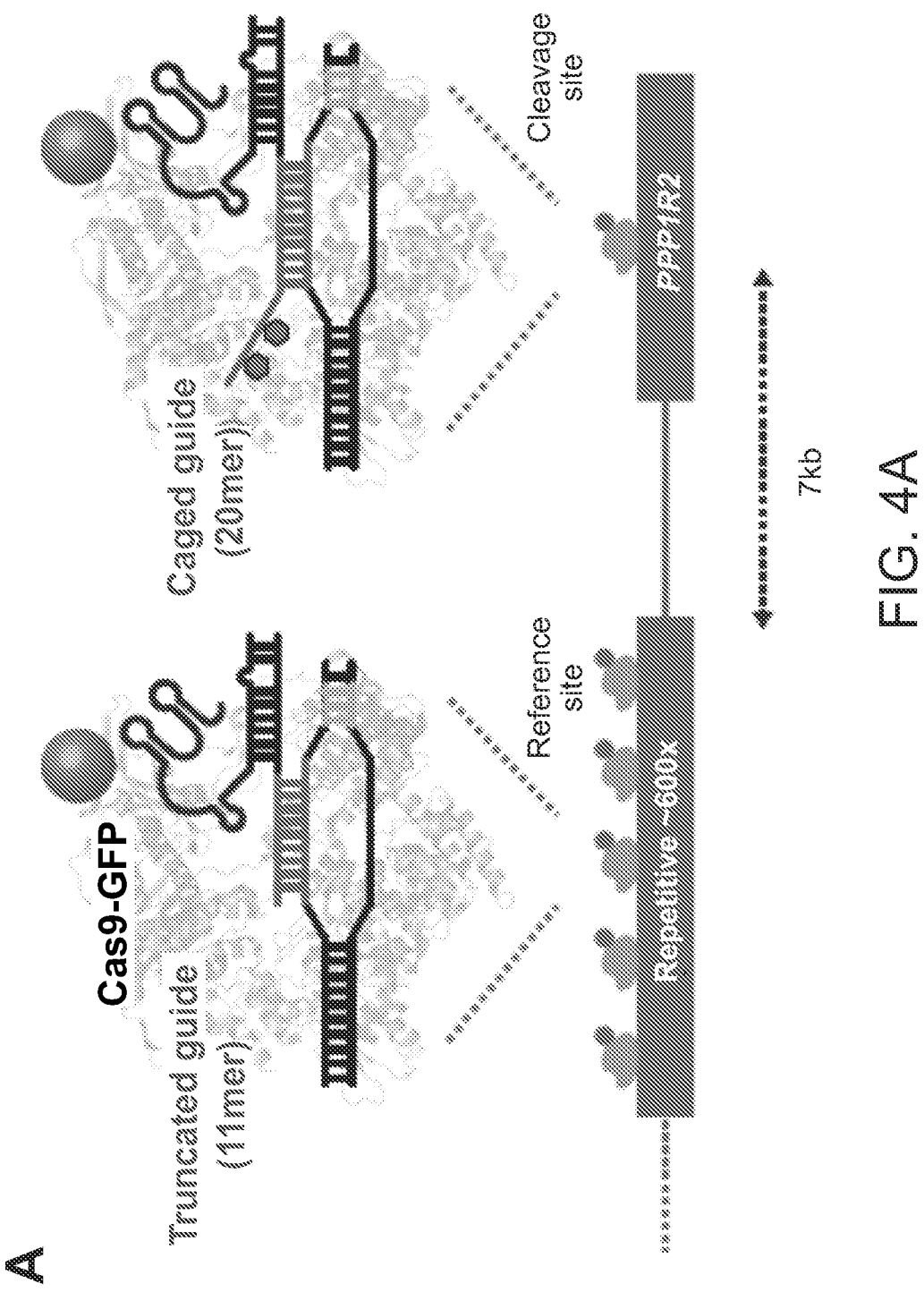
FIGS. 4A-4J are a series of schematics, images, graphs and plots demonstrating the imaging-guided spatiotemporal investigation of Cas9 activation at single cleavage site.

The PPP1R2 gene, located approximately 7 kbp from the repetitive sequence, Ch3rep, was targeted. A truncated gRNA (11 mer) targeting Ch3rep was transfected, which recruits multiple Cas9-EGFP to this repetitive sequence but does not allow cleavage (J. E. Dahlman et al., Orthogonal gene knockout and activation with a catalytically active Cas9 nuclease. *Nat. Biotechnol.* 33, 1159-1161 (2015)). To enable light-initiated single DSB formation, cgRNA (20 mer) targeting the PPP1R2 gene was co-transfected (FIG. 4A). Upon light activation, single DSBs are expected specifically at PPP1R2 cleavage sites while the repetitive Cas9-EGFP array at Ch3rep marks the cleavage site due to its proximity.

Figure 4B:
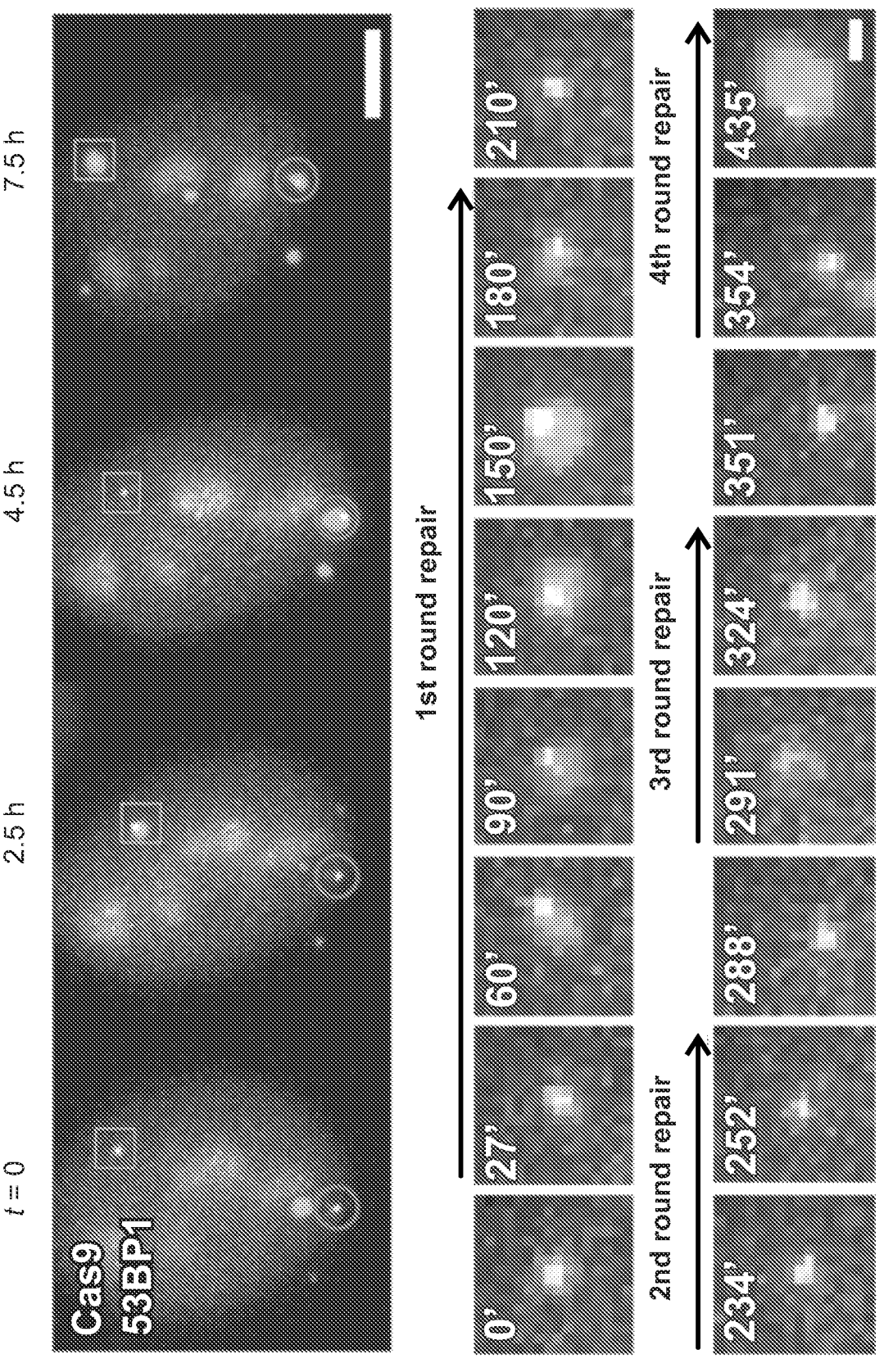
Figure 4C:
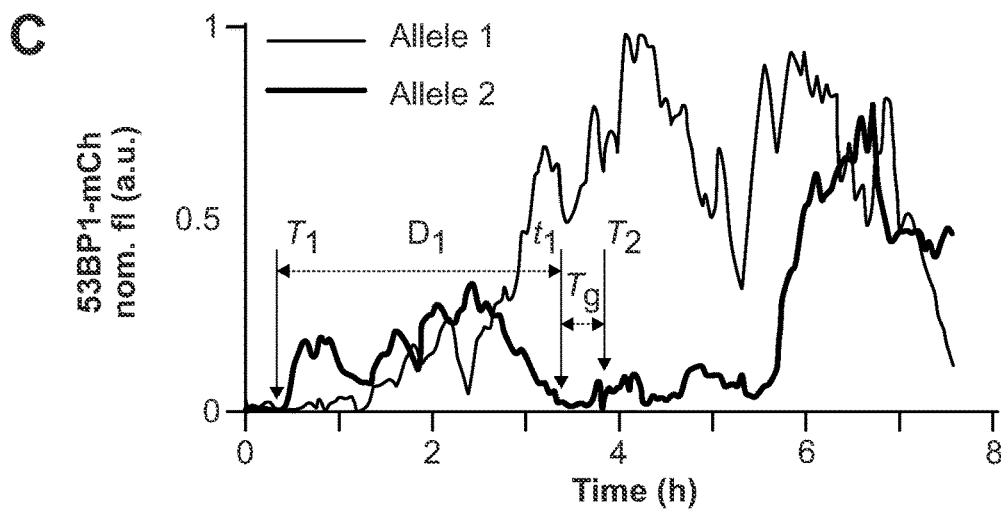
Figure 4D:
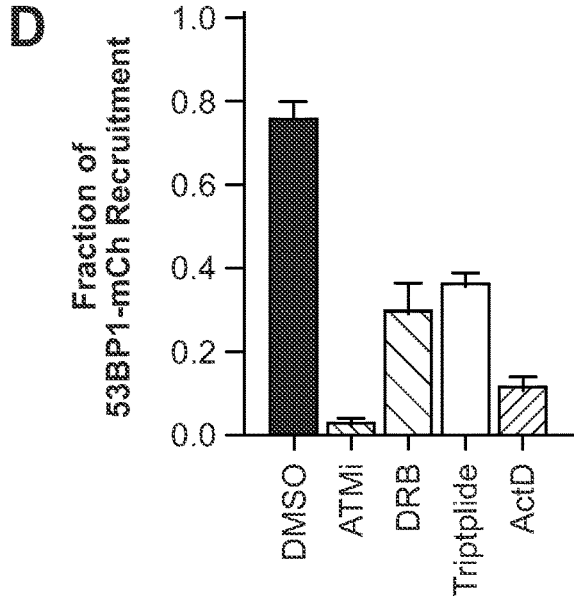
Figure 4E:
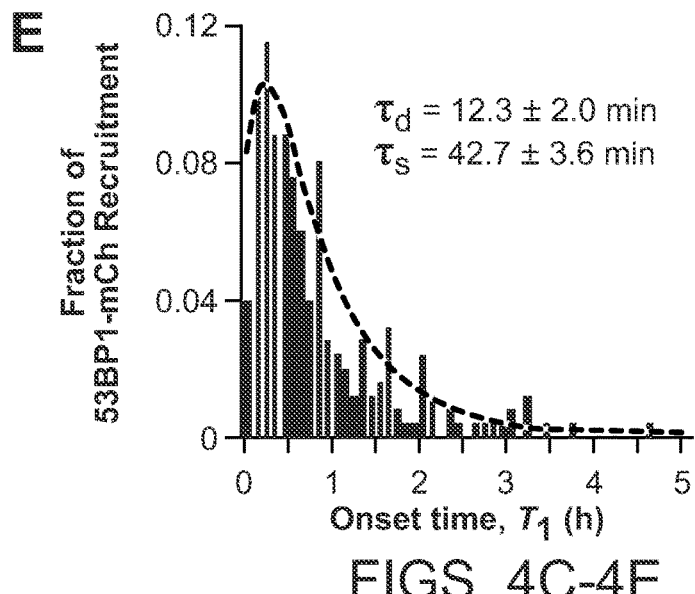

Through live cell imaging, it was observed that ~80% of the Cas9-EGFP loci colocalized with 53BP1-mCherry foci over the course of 8 h post uncaging, indicating repair of DNA cleaved by Cas9 (FIGS. 4B, 4C). Inhibition of ATM kinase eliminated 53BP1-mCherry foci (FIG. 4D). The time point for onset of 53BP1 recruitment was heterogenous between cells and even between alleles in the same cells but 97.1% of 53BP1 foci appeared within 3 h (n=253 alleles), and 20.2% occurred within the first 15 minutes (FIG. 4E). To describe the kinetics of Cas9 cleavage and DNA damage sensing, the initial 53BP1-mCherry arrival time $(T_1)$ was used as a proxy for the initiation of repair. A two-step kinetic model was established to describe the probability distribution of $T_1$: pre-bound Cas9/cgRNA cuts target DNA immediately, but it takes on average zs for an unbound site to be bound and cut by active Cas9/gRNA; after DSB generation, it takes za for the cell to detect the DSB and begin to repair (Example 2). Maximum likelihood estimation was used to fit the distribution of $T_1$ and obtained $\tau_s$ of 42.7±3.6 min and za of 12.3±2.2 min. Therefore, detection of a single Cas9-induced DSB occurs rapidly on the minutes time scale.

Figure 4F:
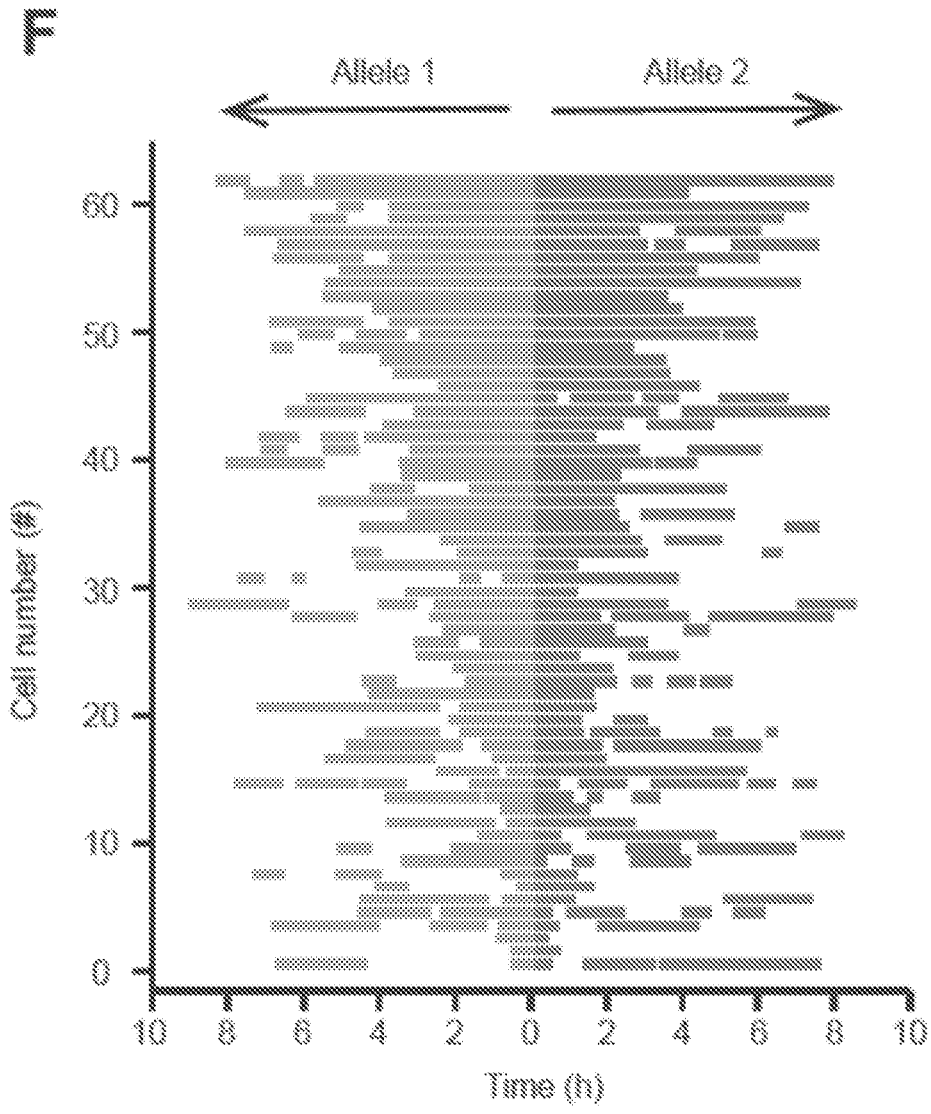
Figures 4G, 4H:
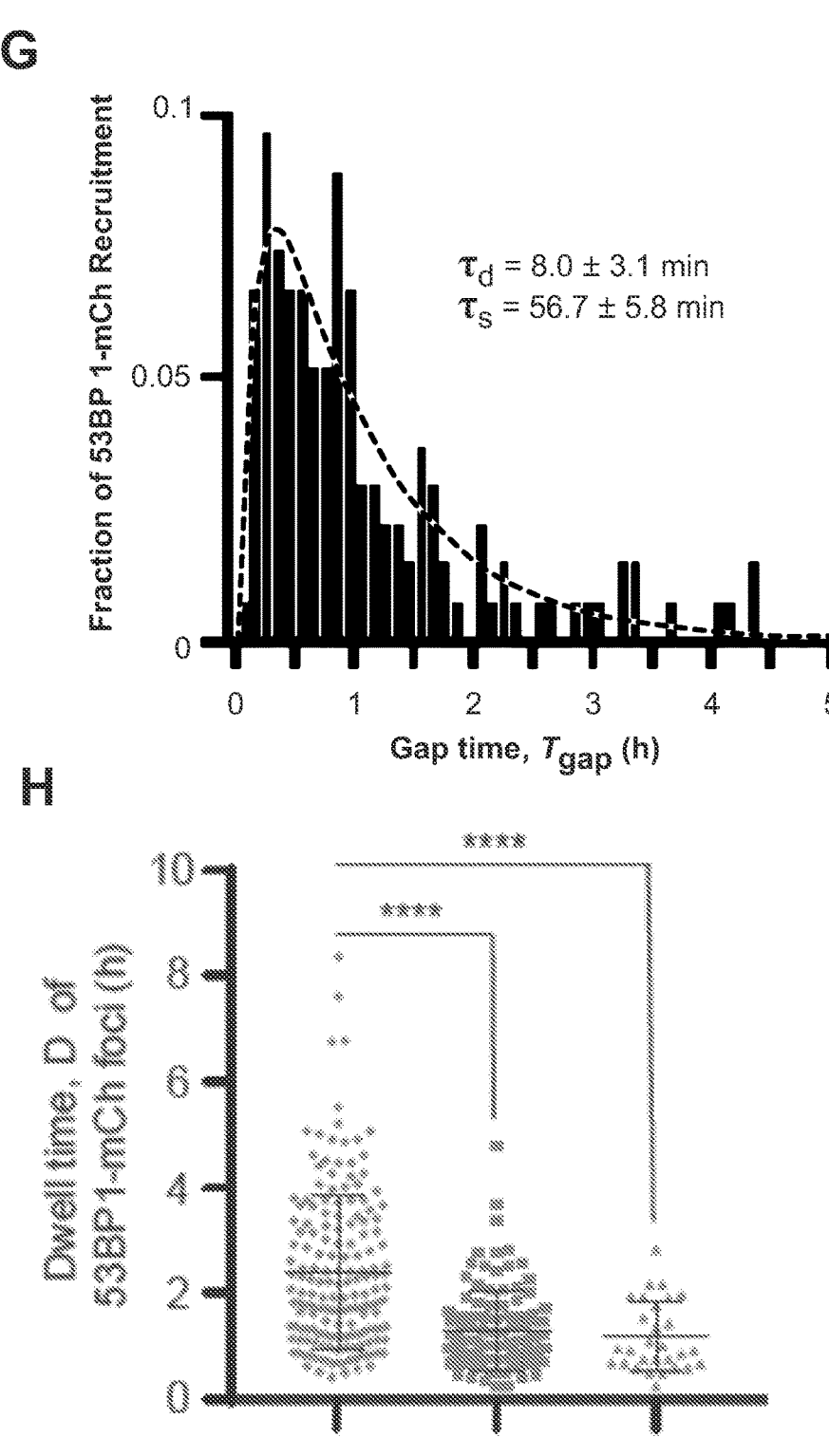

Upon initial recruitment, each 53BP1 focus underwent a cycle of gradual enlargement and dissolution. For ~52.1% of total foci (n=167), additional cycles of 53BP1 recruitment was observed, up to five cycles within 8 h of activation (FIGS. 4B, 4C, 4F). It was hypothesized that this observation corresponded to multiple rounds of DNA repair at the same locus, with each individual cycle representing a complete DNA repair event. To test this hypothesis, the distribution of time interval ($T_g$) was fit between consecutive 53BP1 cycles using the two-step model with no pre-bound Cas9/gRNA, and obtained the Cas9 target searching time ($\tau_s$) of 56.7±5.8 min and DNA damage detection time ($\tau_d$) of 8.0±3.1 min for these subsequent rounds of 53BP1 recruitment (FIG. 4G). The estimated $\tau_s$ and $\tau_d$ for subsequent rounds of 53BP1 recruitment agree well with $\tau_s$ and $\tau_d$ for the first round of DNA repair, demonstrating that new cycles of Cas9 binding and cleavage can indeed occur once the break is repaired (Table 6).

Figure 4I:
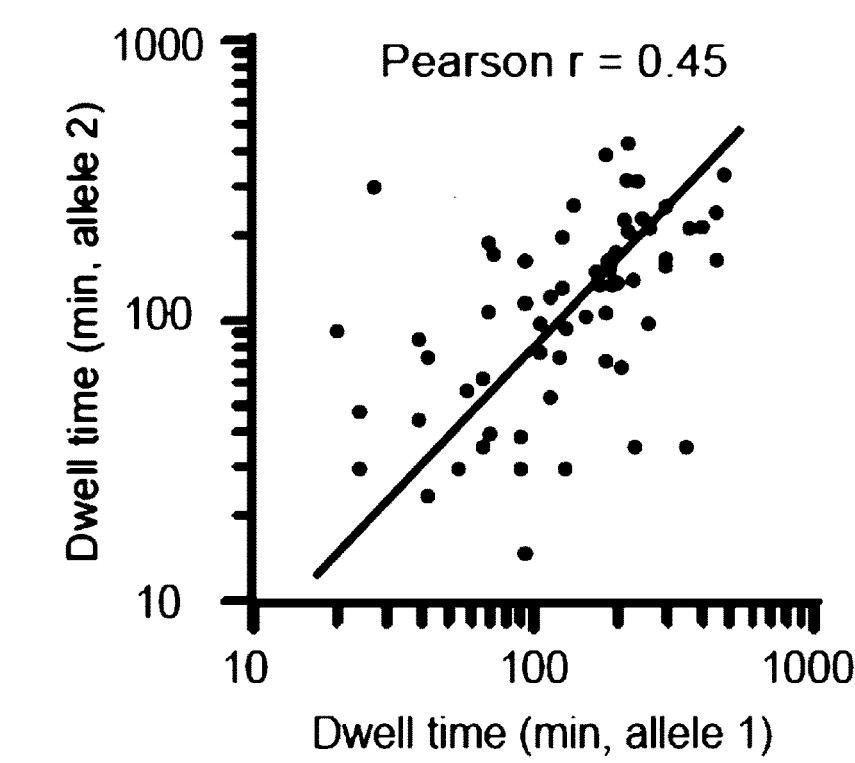
Figure 4J:
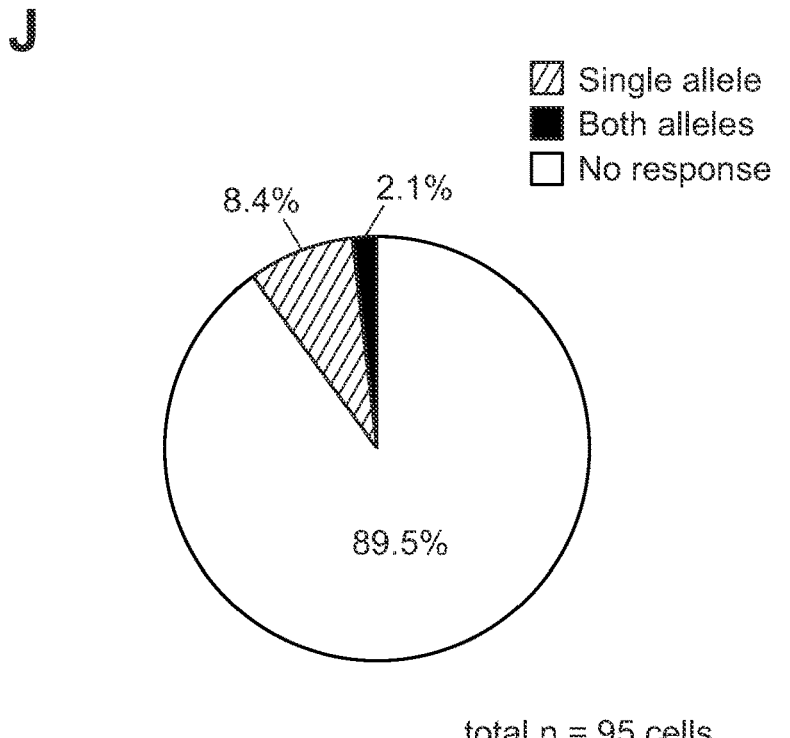
Figure 14:
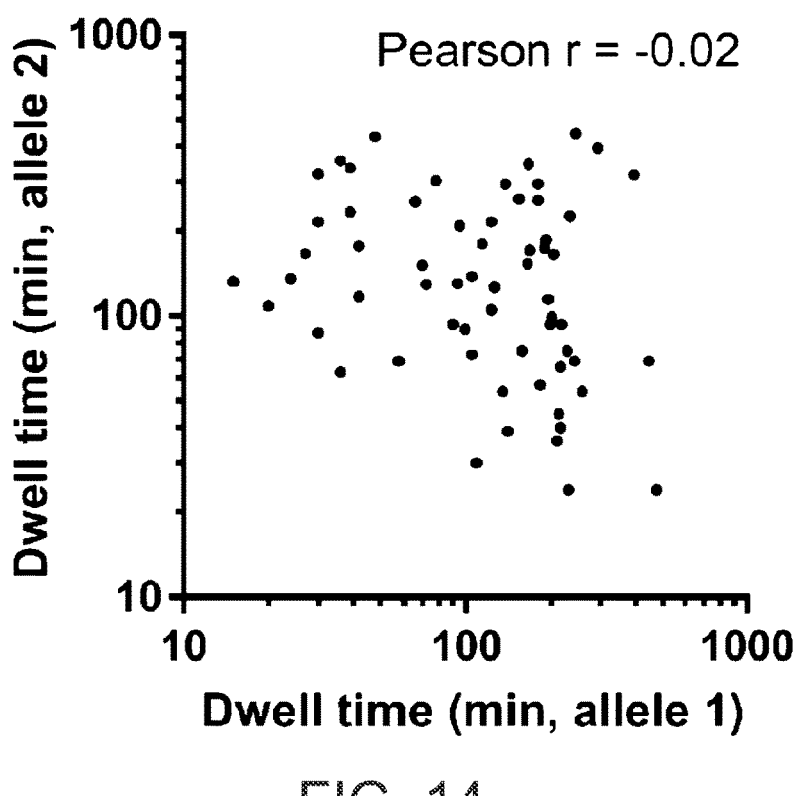
FIG. 14 is a plot of a Pearson correlation analysis showing no correlation of dwell time between two random alleles (r=−0.02).

While the target searching and detection times are comparable for the first versus subsequent repair cycles, the average 53BP1 dwell time (D) was significantly different, with 2.4 (±1.6) h for the first cycle of repair and a much shorter duration of 1.1 (+0.8) h for subsequent cycles (FIG. 4H), hinting for a difference in repairing process. Given that indels formed as early as 3 h and continued to increase afterwards (FIGS. 9A-9D), the data herein also provides evidence that the first round of repair is completed within approximately 3 h. Pearson correlation analysis showed that dwell times of two alleles in the same cell are positively correlated (correlation coefficient of 0.45, FIGS. 4F, 4I), but not between different cells (correlation coefficient –0.02, FIG. 14), indicating that variation in 53BP1 dwell times at each DSB repair site arises predominantly from intracellular states such as cell cycle status and levels of repair proteins.

Transcription has been proposed to facilitate the exposure of Cas9-induced DSBs and indel formation (R. Clarke et al. Enhanced Bacterial Immunity and Mammalian Genome Editing via RNA-Polymerase-Mediated Dislodging of Cas9 from Double-Strand DNA Breaks. *Mol. Cell.* 71, 42-55.e8 (2018)). To investigate this effect, 53BP1 recruitment was tracked to DSB sites in U-2 OS cells treated with various transcription inhibitors (FIG. 4D). The fraction of 53BP1 recruitment was significantly reduced from –76% in DMSO control to 10-30% upon transcription inhibition, implying that transcription indeed plays an important role in cellular detection of Cas9-induced DSBs. The average dwell time of 53BP1 was 1.0 (±0.6) h in the presence of a transcription inhibitor DRB (FIG. 4H), which was much shorter than the case when no inhibitor was applied. Coincidently, it matches the dwell time of the second cycle of DNA repair when transcription is active.

Figure 15:
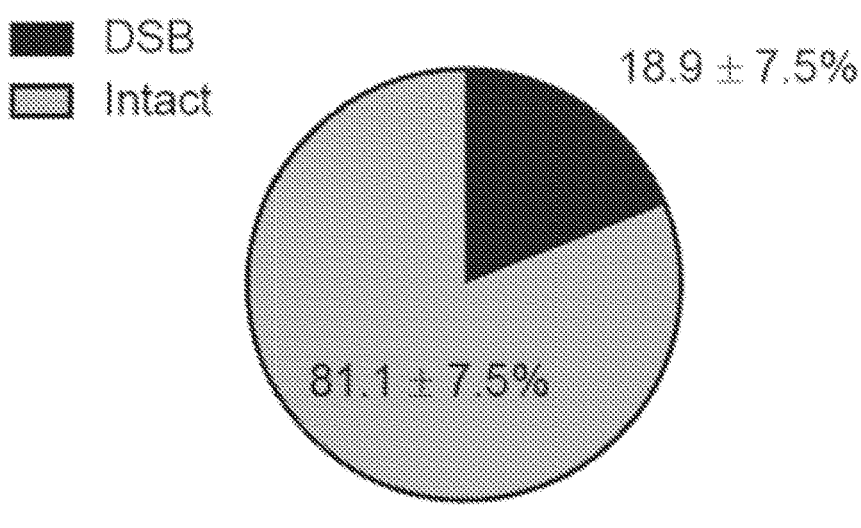
FIG. 15 is a pie chart showing the quantification of DSB percent at PPP1R2 locus in U2OS cells. ddPCR experiments measured an average of 18.9±7.5% of DSB generated at PPP1R2 locus 1 min after light stimulation (365 nm, 30 s, n=3 biological triplicates) in U2OS cells. Given that there is a ~4% basal DSB readout (FIG. 2B), we reports a final average of 15% DSB generated at the PPP1R2 locus within 30 s, providing evidence that ~15% of Cas9/cgRNA are prebound in imaging experiments for U2OS cells.

Finally, single allele cleavage was tested at the nonrepetitive target (PPP1R2 gene) using a laser beam focused at the nearby repetitive Ch3rep locus decorated with Cas9-EGFP. 8.4% of the illuminated single PPP1R2 loci recruited 53BP1 was observed (FIG. 4F), which is over 50% of the estimated –15% of loci with pre-bound Cas9 at the cleavage site inferred from ddPCR-based DSB quantification (FIG. 15). Single allele 53BP1-mCherry recruitment specificity to the illuminated allele was 80%. In contrast to the experiments where all Cas9/cgRNA within a cell were activated, no additional rounds of 53BP1-mCherry recruitment was observed when a single allele was cleaved. A possible explanation for both the high single-allele specificity and lack of additional repair events is that because only a very small subset of Cas9/cgRNA was locally activated, after dilution of this population within the cell over time, the probability for an active RNP, within a large pool of inactive RNPs, to bind and cleave is low.

An efficient, inducible CRISPR/Cas9 system that is activated by light within seconds was developed. With this very fast CRISPR system, we observed rapid generation of DSBs in the seconds time scale, indel formation in the range of 30 min to 6 h, and final detectable indels of >90% for most loci we tested. An accurate kinetic model was also developed for Cas9-mediated DNA cleavage and repair that revealed a previously uncharacterized process: the significant cleavage of indels. Indeed, recent studies have demonstrated that Cas9-induced NHEJ products are predominantly +1/–1 indels for thousands of genomic targets (M. W. Shen et al. Predictable and precise template-free CRISPR editing of pathogenic variants. *Nature.* 563, 646-651 (2018); F. Allen et al., Predicting the mutations generated by repair of Cas9-induced double-strand breaks. *Nat. Biotechnol.* 37, 64-72 (2019); A. M. Chakrabarti et al., Target-Specific Precision of CRISPR-Mediated Genome Editing. *Mol. Cell.* 73, 699-713.e6 (2018)), suggesting that repetitive cleavage of DNA targets, even in the presence of indels, is a universal phenomenon and a potential contributor to p53 checkpoint activation that leads to cell cycle arrest and apoptosis (E. Haapaniemi et al., CRISPR-Cas9 genome editing induces a p53-mediated DNA damage response. *Nat. Med.* 24, 927-930 (2018); R. J. Ihry et al., P53 inhibits CRISPR-Cas9 engineering in human pluripotent stem cells. *Nat. Med.* 24, 939-946 (2018)).

By combining single cell fluorescence imaging and subcellular Cas9 activation with high spatial precision, Cas9-induced DDR dynamics at the single allele resolution were interrogated. When targeting active Cas9s to the repetitive region, the data provide evidence that Cas9 remains bound to genomic DNA after cleavage until a stochastic unbinding event allows access to the DSB by the cell, which rapidly recruits ATM kinase. This leads to diverse histone modifications and further recruitment of repair proteins (e.g. MDC1, 53BP1) that creates a dynamic chromatin environment typically spanning over 1 megabase pairs (E. P. Rogakou et al., Megabase chromatin domains involved in DNA double-strand breaks in vivo. *J Cell Biol.* 146, 905-916 (1999); T. Clouaire et al., Comprehensive Mapping of Histone Modifications at DNA Double-Strand Breaks Deciphers Repair Pathway Chromatin Signatures. *Mol. Cell.* 72, 250-262.e6 (2018).). ATM activity within this environment facilitates the exposure of the nearby Cas9-bound DSBs, consistent with our observation that ATM inhibition slows the disappearance of the repetitive Cas9 foci.

When activating Cas9 at a single cleavage site, the Cas9-induced 53BP1 foci appear as early as a few minutes, unambiguously showing that detection of Cas9-induced breaks occurs within minutes. The mathematical model herein, deduced that a single DSB is detected in –10 min after Cas9 cleavage, but it is believed s to be an upper bound because many DNA damage responders such as Ku-70/80, MRN complex and MDC1 are known to interact with cleaved dsDNA before the observed readout of 53BP1 foci formation (T. Clouaire et al., Comprehensive Mapping of Histone Modifications at DNA Double-Strand Breaks Deciphers Repair Pathway Chromatin Signatures. *Mol. Cell.* 72, 250-262.e6 (2018)). 53BP1 foci last for –3 h for the initial round of DNA repair and are much more transient for subsequent rounds of repair or when transcription is inhibited. Mechanistic interplay between Cas9-induced DNA damage repair and transcription activity is still subject to future study.

The ability to initiate DNA damage at one allele but not the other with high reproducibility suggests a method to physically limit Cas9 off-target activity through submicron spatial confinement. If the non-targeted allele, which has identical sequence to the targeted allele, can remain free of observable DNA damage response, one can reasonably assume that all potential off-target sites not coincidentally illuminated by the submicron activation beam are also unlikely to be cleaved by Cas9.

The very fast CRISPR/Cas9 system described herein, provided the highest spatial and temporal resolution to induce site-specific double strand breaks in living cells. Compared to other systems that induce genomic damages (e.g. ionizing radiation, chemical reagents, homing endonucleases, laser micro-irradiation) (T. Clouaire, G. Legube, A Snapshot on the Cis Chromatin Response to DNA Double-Strand Breaks. *Trends Genet.* 35, 330-345 (2019)), the utilization of Cas9 enables investigation into the spatiotemporal dynamics of DDR from an infinite pool of endogenous DNA targets with sequence specificity. It is envisioned that the combined single cell fluorescence microscopy with high resolution Cas9 photoactivation strategy presented here are highly generalizable for the study of many other repair proteins, Cas9 based systems (e.g. single nucleotide base editors and nickases) and potentially for precise genome editing with single allele specificity.

TABLE 1 crRNA and tracrRNA sequences

| Name | Italics highlights dT-NPOM replacement;Bold marks the RNA sequences hybridizing with target DNA |
|---|---|
| | crRNA Sequences (5' to 3') |
| ACTB | GCUAUUCUCGCAGCUCACCA GUUUUAGAGCUAUGCUGUUUUG (SEQ ID NO: 1) |
| IFT88 | GUUACUAGACCUAUAGCUAC GUUUUAGAGCUAUGCUGUUUUG (SEQ ID NO: 2) |
| MYC | GUAAUUCCAGCGAGAGGCAG GUUUUAGAGCUAUGCUGUUUUG (SEQ ID NO: 3) |
| PPP1R2 | GACUUCCUCUAUGGUGGCGU GUUUUAGAGCUAUGCUGUUUUG (SEQ ID NO: 4) |
| Ch3rep | UCCUCUGUAUGAUAUCACAG GUUUUAGAGCUAUGCUGUUUUG (SEQ ID NO: 5) |
| Ch3rep (11mer) | UGAUAUCACAGGUUUUAGAGC UAUGCUGUUUUG (SEQ ID NO: 6) |
| | tracrRNA sequences (5' to 3') |
| tracrRNA | AGCAUAGCAAGUUAAAAUAAG GCUAGUCCGUUAUCAACUUGAA AAAGUGGCACCGAGUCGGUGCUUU (SEQ ID NO: 7) |

TABLE 2

PCR primers for ddPCR

| Name | Sequence (5' to 3') |
|---|---|
| ACTB_F1 | TGGCGGCCTAAGGACTCG (SEQ ID NO: 8) |
| ACTB_R1 | GAAGCCGGCCTTGCACATG (SEQ ID NO: 9) |
| ACTB_F2 | CACAGGAGCCTCCCGGTTTC (SEQ ID NO: 10) |
| ACTB_R2 | CTTCAGGGTGAGGATGCCTCTC (SEQ ID NO: 11) |
| ACTB_ Probe1 | /56-FAM/CGACCTCGG/ZEN/ CTCACAGCGCGCC/3IABkFQ/ (SEQ ID NO: 12) |
| ACTB_ Probe2 | /5HEX/CTGCGCCCG/ZEN/ TGCTCAGGGCTTCTTG/3IABkFQ/ (SEQ ID NO: 13) |
| IFT88_F1 | CTCAGTCTGAATCCTGTTAAC (SEQ ID NO: 14) |
| IFT88_R1 | CCTAAAGTGAACTATTGTATGAG (SEQ ID NO: 15) |
| IFT88_F2 | GTGTCTATTGTTTGGCCTAGT (SEQ ID NO: 16) |
| IFT88_R2 | GTGAGAAGGAGACTCATTCT (SEQ ID NO: 17) |
| IFT88_ Probe1 | /56-FAM/CTGCTAAAA/ZEN/ TATCAAGCACGGCAG/3IABkFQ/ (SEQ ID NO: 18) |
| IFT88_ Probe2 | /5HEX/CTTATCGGC/ZEN/ ACCTCAGATCGTTC/3IABkFQ/ (SEQ ID NO: 19) |
| MYC_F1 | TTGGCGGGAAAAAGAACGG (SEQ ID NO: 20) |
| MYC_R1 | TATTCGCTCCGGATCTCCCT (SEQ ID NO: 21) |
| MYC_F2 | GCCAGCGGTCCGCAAC (SEQ ID NO: 22) |
| MYC_R2 | GAGAGCCTTTCAGAGAAGCGG (SEQ ID NO: 23) |
| MYC_ Probe1 | /56-FAM/TCGGGGCTT/ZEN/ TATCTAACTCGCTG/3IABkFQ/ (SEQ ID NO: 24) |
| MYC_ Probe2 | /5HEX/CACGAAACT/ZEN/ TTGCCCATAGCAGC/3IABkFQ (SEQ ID NO: 25) |

TABLE 3

PCR primers for Sanger sequencing

| Name | Sequence (5' to 3') |
|---|---|
| ACTB_F | TGGCGGCCTAAGGACTCG (SEQ ID NO: 26) |
| ACTB_R | CTTCAGGGTGAGGATGCCTCTC (SEQ ID NO: 27) |

TABLE 3-continued

| PCR primers for Sanger sequencing | |
| --- | --- |
| Name | Sequence (5' to 3') |
| IFT88_F | CTCAGTCTGAATCCTGTTAAC<br>(SEQ ID NO: 28) |
| IFT88_R | CACTTCTGAAACACTTTTCTTAC<br>(SEQ ID NO: 29) |
| MYC_F | TTGGCGGGAAAAAGAACGG<br>(SEQ ID NO: 30) |
| MYC_R | GAGAGCCTTTCAGAGAAGCGG<br>(SEQ ID NO: 31) |
| PPP1R2_F | GTTTCCGAGGCAGCAGTTG<br>(SEQ ID NO: 32) |
| PPP1R2_R | GCATGATAAACGTCATCGCCC<br>(SEQ ID NO: 33) |

TABLE 4

| Amplicon PCR primers for next generation sequencing | |
| --- | --- |
| Name | Sequence (5' to 3') |
| NGS_ACTB_F | tcgtcggcagcgtcagatgtgtataagagacag<br>TGGCGGCCTAAGGACTCG<br>(SEQ ID NO: 34) |
| NGS_ACTB_R | gtctcgtgggctcggagatgtgtataagagacag<br>GAAGCCGGCCTTGCACATG<br>(SEQ ID NO: 35) |
| NGS_IFT88_F | tcgtcggcagcgtcagatgtgtataagagacag<br>CTCAGTCTGAATCCTGTTAAC<br>(SEQ ID NO: 36) |
| NGS_IFT88_R | gtctcgtgggctcggagatgtgtataagagacag<br>CCTAAAGTGAACTATTGTATGAG<br>(SEQ ID NO: 37) |
| NGS_MYC_F | tcgtcggcagcgtcagatgtgtataagagacag<br>GGGATCGCGCTGAGTATAAA<br>(SEQ ID NO: 38) |
| NGS_MYC_R | gtctcgtgggctcggagatgtgtataagagacag<br>TGGGCAAAGTTTCGTGGA<br>(SEQ ID NO: 39) |
| NGS_PPP1R2_F | tcgtcggcagcgtcagatgtgtataagagacag<br>GCCCATCAAGGGGATCTTGA<br>(SEQ ID NO: 40) |
| NGS_PPP1R2_R | gtctcgtgggctcggagatgtgtataagagacag<br>CTGGGGTCTGGGTAGGTAAC<br>(SEQ ID NO: 41) |
| NGS_Index_F1 | AATGATACGGCGACCACCGAGATCTACACCTCTC<br>TATTCGTCGGCAGCGTC<br>(SEQ ID NO: 41) |
| NGS_Index_F2 | AATGATACGGCGACCACCGAGATCTACACTATCC<br>TCTTCGTCGGCAGCGTC<br>(SEQ ID NO: 42) |
| NGS_Index_F3 | AATGATACGGCGACCACCGAGATCTACACGTAAG<br>GAGTCGTCGGCAGCGTC<br>(SEQ ID NO: 43) |
| NGS_Index_F4 | AATGATACGGCGACCACCGAGATCTACACACTGC<br>ATATCGTCGGCAGCGTC<br>(SEQ ID NO: 44) |

TABLE 4-continued

| Amplicon PCR primers for next generation sequencing | |
| --- | --- |
| Name | Sequence (5' to 3') |
| NGS_Index_F5 | AATGATACGGCGACCACCGAGATCTACACAAGGA<br>GTATCGTCGGCAGCGTC<br>(SEQ ID NO: 45) |
| NGS_Index_F6 | AATGATACGGCGACCACCGAGATCTACACCTAAG<br>CCTTCGTCGGCAGCGTC<br>(SEQ ID NO: 46) |
| NGS_Index_F7 | AATGATACGGCGACCACCGAGATCTACACCGTCT<br>AATTCGTCGGCAGCGTC<br>(SEQ ID NO: 47) |
| NGS_Index_F8 | AATGATACGGCGACCACCGAGATCTACACTCTCT<br>CCGTCGTCGGCAGCGTC<br>(SEQ ID NO: 48) |
| NGS_Index_R1 | CAAGCAGAAGACGGCATACGAGATTCGCCTTAGT<br>CTCGTGGGCTCGG<br>(SEQ ID NO: 49) |
| NGS_Index_R2 | CAAGCAGAAGACGGCATACGAGATCTAGTACGGT<br>CTCGTGGGCTCGG<br>(SEQ ID NO: 50) |
| NGS_Index_R3 | CAAGCAGAAGACGGCATACGAGATTTCTGCCTGT<br>CTCGTGGGCTCGG<br>(SEQ ID NO: 51) |
| NGS_Index_R4 | CAAGCAGAAGACGGCATACGAGATGCTCAGGAGT<br>CTCGTGGGCTCGG<br>(SEQ ID NO: 52) |
| NGS_Index_R5 | CAAGCAGAAGACGGCATACGAGATAGGAGTCCGT<br>CTCGTGGGCTCGG<br>(SEQ ID NO: 53) |
| NGS_Index_R6 | CAAGCAGAAGACGGCATACGAGATCATGCCTAGT<br>CTCGTGGGCTCGG<br>(SEQ ID NO: 54) |
| NGS_Index_R7 | CAAGCAGAAGACGGCATACGAGATGTAGAGAGGT<br>CTCGTGGGCTCGG<br>(SEQ ID NO: 55) |
| NGS_Index_R8 | CAAGCAGAAGACGGCATACGAGATCAGCCTCGGT<br>CTCGTGGGCTCGG<br>(SEQ ID NO: 56) |

TABLE 6

Theoretical modeling and determination of DNA
damage sensing and Cas9 target search in U-2 OS cells.

| Gene | Initial arrival rime (min) | | | Time gap (min) | | | $\Delta$ (min) $B_0 \tau_s$, |
|---|---|---|---|---|---|---|---|
| | $\langle T_i \rangle$ | $\tau_d$ | $\tau_s$ | $\langle T_{gap} \rangle$ | $\tau_d$ | $\tau_s$ | avg |
| PPP1R2 | 49.1 ± 46.9 | 12.3 ± 2.2 | 42.7 ± 3.6 | 64.3 ± 58.0 | 8.0 ± 3.1 | 56.7 ± 5.8 | 7.5 |

TABLE 7 dsDNA fragment sequences used in in vitro
cleavage assay

| Name | Sequences (5' to 3') Bold marks WT/+1/−1 protospacer sequences |
|---|---|
| ACTB WT | TGGCGGCCTAAGGACTCGGCGCGCCGGAAGTGGCCAGGGCG GGGGCGACTTCGGCTCACAGCGCGCCCGGCTATTCTCGCAG CTCACCATGGATGATGATATCGCCGCGCTCGTCGTCGACAA CGGCTCCGGCATGTGCAAGGCCGGCTTCGCGGGCGACGATG CCCCCCGGGCCGTCTTCCCCTCCATCGTGGGGCGCCCCAGG CACCAGGTAGGGGAGCTGGCTGGGTGGGGCAGCCCCGGGAG CGGGCGGGAGGCAAGGGCGCTTTCTCTGCACAGGAGCCTCC CGGTTTCCGGGGTGGGGGCTGCGCCCGTGCTCAGGGCTTCT TGTCCTTTCCTTCCCAGGGCGTGATGGTGGGCATGG GTCA GAAGATTCCTATGTGGGCGACGAGGCCCAGAGCAAGAGAGG CATCCTCACCCTGAAG (SEQ ID NO: 57) |
| ACTB +1 | TGGCGGCCTAAGGACTCGGCGCGCCGGAAGTGGCCAGGGCG GGGGCGACTTCGGCTCACAGCGCGCCCGGCTATTCTCGCAG CTCAACCATGGATGATGATATCGCCGCGCTCGTCGTCGACA ACGGCTCCGGCATGTGCAAGGCCGGCTTCGCGGGCGACGAT GCCCCCCGGGCCGTCTTCCCCTCCATCGTGGGGCGCCCCAG GCACCAGGTAGGGGAGCTGGCTGGGTGGGGCAGCCCCGGGA GCGGGCGGGAGGCAAGGGCGCTTTCTCTGCACAGGAGCCTC CCGGTTTCCGGGGTGGGGGCTGCGCCCGTGCTCAGGGCTTC TTGTCCTTTCCTTCCCAGGGCGTGATGGTGGGCATG GGTC AGAAGATTCCTATGTGGGCGACGAGGCCCAGAGCAAGAGA GGCATCCTCACCCTGAAG (SEQ ID NO: 58) |
| MYC WT | TTGGCGGGAAAAAGAACGGAGGGAGGGATCGCGCTGAGTAT AAAAGCCGGTTTTCGGGGCTTTATCTAACTCGCTGTAGTAA TTCCAGCGAGAGGCAGAGGGAGCGAGCGGGCGGCCGGCTAG GGTGGAAGAGCCGGGCGAGCAGAGCTGCGCTGCGGGCGTCC TGGGAAGGGAGATCCGGAGCGAATAGGGGGCTTCGCCTCTG GCCCAGCCCTCCCGCTGATCCCCCAGCCAGCGGTCCGCAAC CCTTGCCGCATCCACGAAACTTTGCCCATAGCAGCGGGCGG GCACTTTGCACTGGAACTTACAACACCCGAGCAAGGACGCG ACTCTCCCGACGCGGGGAGGCTATTCTGCCCATTTGGGGAC ACTTCCCCGCCGCTGCCAGGACCCGCTTCTCTGAAAGGCTC TC (SEQ ID NO: 59) |
| MYC +1 | TTGGCGGGAAAAAGAACGGAGGGAGGGATCGCGCTGAGTAT AAAAGCCGGTTTTCGGGGCTTTATCTAACTCGCTGTAGTAA TTCCAGCGAGAGGCCAGAGGGAGCGAGCGGGCGGCCGGCTA GGGTGGAAGAGCCGGGCGAGCAGAGCTGCGCTGCGGGCGTC CTGGGAAGGGAGATCCGGAGCGAATAGGGGGCTTCGCCTCT GGCCCAGCCCTCCCGCTGATCCCCCAGCCAGCGGTCCGCAA CCCTTGCCGCATCCACGAAACTTTGCCCATAGCAGCGGGCG GGCACTTTGCACTGGAACTTACAACACCCGAGCAAGGACGC GACTCTCCCGACGCGGGGAGGCTATTCTGCCCATTTGGGGA CACTTCCCCGCCGCTGCCAGGACCCGCTTCTCTGAAAGGCT CTC (SEQ ID NO: 60) |
| MYC −1 | TTGGCGGGAAAAAGAACGGAGGGAGGGATCGCGCTGAGTAT AAAAGCCGGTTTTCGGGGCTTTATCTAACTCGCTGTAGTAA TTCCAGCGAGAGCAGAGGGAGCGAGCGGGCGGCCGGCTAGG GTGGAAGAGCCGGGCGAGCAGAGCTGCGCTGCGGGCGTCCT GGGAAGGGAGATCCGGAGCGAATAGGGGGCTTCGCCTCTGG CCCAGCCCTCCCGCTGATCCCCCAGCCAGCGGTCCGCAACC CTTGCCGCATCCACGAAACTTTGCCCATAGCAGCGGGCGGG |

TABLE 7-continued dsDNA fragment sequences used in in vitro
cleavage assay

| Name | Sequences (5' to 3') Bold marks WT/+1/−1 protospacer sequences |
|---|---|
| | CACTTTGCACTGGAACTTACAACACCCGAGCAAGGACGCGA CTCTCCCGACGCGGGGAGGCTATTCTGCCCATTTGGGGACA CTTCCCCGCCGCTGCCAGGACCCGCTTCTCTGAAAGGCTCT C (SEQ ID NO: 61) |

Example 2: Kinetic Model of Cas9-Induced DSB and Indel Formation

A previously described kinetic model of DSB and Indel formation was adapted (E. K. Brinkman et al., Kinetics and Fidelity of the Repair of Cas9-Induced Double-Strand DNA Breaks. *Mol. Cell.* 70, 801-813.e6 (2018)). Assume at the time of uncaging, there is a fraction of DNA foci $B_0$ are pre-bound by Cas9/cgRNA. Because cleavage by pre-bound Cas9/cgRNA occurs within seconds of light illumination (t=0) and the earliest data points for DSB and Indel are at 30 s, we assign DSB at time 0 equal to the pre-bound fraction (DSB(t=0)=$B_0$). An intact DNA target that is not bound by an RNP is cut with an apparent cleavage rate $k_s$ to generate DSB. Note that the rate $k_s$ depends on the DNA locus and activated Cas9-gRNA concentration, and it is mainly determined by the rate of target searching which is much slower than cleavage. A DSB can be repaired perfectly with a rate $k_p$, or it can be repaired with a rate $k_m$ to generate an Indel.

Based on these definitions, Model I was established assuming that Indels cannot be re-cut by Cas9:

$$\text{Intact} \underset{k_p}{\overset{k_s}{\rightleftharpoons}} DSB \overset{k_m}{\rightarrow} \text{Indel} \qquad \text{(Model I)}$$

Because the active pool of Cas9/cgRNA from the one-time delivery is expected to degrade over time, the proportion of active pool is modeled with an exponential decay function $$\text{Cas}_t = \exp(-k_{deg}t) \qquad (1)$$

where $k_{deg}$ is the rate of removal of Cas9/cgRNA from the active pool (Cas9/cgRNA that is able to act on the genomic DNA substrate). This reaction is then modeled as a set of coupled ordinary differential equations:

$$\frac{d\,DSB}{dt} = k_s Cas_t\, \text{Intact} - (k_m + k_p)DSB \qquad (2)$$

$$\frac{d\,\text{Indel}}{dt} = k_m DSB \qquad (3)$$

satisfying the normalization condition

Intact+DSB+Indel=1 (4)

and the initial condition:

Intact(0)=1−$B_0$,DSB(0)=$B_0$,Indel(0)=0 (5)

An alternative model is that the Indel can be re-cut with the rate $k_{rc}$. Because there are many different types of Indels generated by repair, the rate $k_{rc}$ should be taken as an average of different Indels. In general, $k_{rc}$ is expected to be 0 or much smaller than the wide type rate $k_s$. In addition, because of the insertion and deletion, the position of Indel generated DSB will be different from the original one. These Indel generated DSBs could be repaired perfectly or produce other Indels, but it is unlikely to regenerate the original DNA sequence. This Model II is summarized by the reaction scheme:

$$\text{Intact} \underset{k_p}{\overset{k_s}{\rightleftharpoons}} DSB_1 \overset{k_m}{\to} \text{Indel} \underset{k_m+k_p}{\overset{k_{rc}}{\rightleftharpoons}} DSB_2. \qquad (\text{Model II})$$

The differential equations to describe Model II are:

$$\frac{dDSB1}{dt} = k_s Cas_t\, \text{Intact} - (k_m + k_p)DSB_1 \qquad (6)$$

$$\frac{d\,\text{Indel}}{dt} = k_m DSB_1 + (k_m + k_p)DSB_2 - k_{rc}Cas_t\, \text{Indel}, \qquad (7)$$

$$\frac{dDSB2}{dt} = k_{rc}Cas_t\, \text{Intact} - (k_m + k_p)DSB_2 \qquad (8)$$

satisfying the normalization condition

Intact+DSB$_1$+DBS$_2$+Indel=1 (9)

and the initial condition:

Intact(0)=1−$B_0$,DSB$_1$(0)=$B_0$,DSB$_2$(0)=0Indel(0)=0 (10)

The experimentally measured DSB will be the sum of the two types of DSBs,

DSB=DSB$_1$+DSB$_2$ (11)

Both sets of equations (2-5) and (6-11) were solved. The theoretical DSB and Indel curves were fitted to experimentally measured DSB and Indel vs t simultaneously with nonlinear least squares method in a single optimization problem that determined the model parameters for each locus as well as a single $k_{deg}$.

Before uncaging, it was assumed that the fraction of DNA bound by Cas9/cgRNA is $B_0$ and the unbound fraction is 1−$B_0$. After uncaging, the Cas9-bound DNA results in DSB with a rate $k_B$, while the unbound fraction needs to be bound by Cas9/gRNA and then cut. Target search can be viewed as a chemical reaction with a rate $k_S$, which depends on the accessibility of the locus itself, and the concentration of Cas9/gRNA. Alternatively, the Cas9/gRNA binding events can be described stochastically as a Poisson process and the target search time $t_s$ is an exponentially distributed random variable with mean value $\tau_S$−1/$k_S$. After DNA is cut, the DSB will eventually be exposed, for example due to ejection of Cas9/gRNA, and DSB repair proteins will be deployed at the damage site. The first appearance of repair proteins, 53BP1 in the experiment, is viewed as the start of DNA repair. As a first order approximation, it was assumed that it is described by a single rate $k_d$. Therefore, the time from DNA being cut to the start of DNA repair is described by a random variable $\tau_d$, that is exponentially distributed with mean value $\tau_d$=1/$k_d$. This is summarized in the following reaction scheme.

$$\underset{1-B_0}{\text{unbound } DNA} \overset{k_s}{\to} \underset{B_0}{DNA - Cas9} \overset{k_B}{\to} DNA^{break} -$$

$$Cas9 \overset{k_d}{\to} DNA^{break} - \text{Repair Protein} + Cas9$$

Experimentally, the initial arrival time $T_1$ of a DSB repair protein, 53BP1, was measured starting from t=0, the moment of cgRNA uncaging. From in vitro and in vivo experiments, it was known that a pre-bound Cas9/gRNA cuts the DNA within seconds after activation, which is much faster than target search and DSB exposure and detection. Therefore, $k_B \gg k_S$ or $k_d$. So we ignore the time it takes for a pre-bound Cas9/gRNA to cut DNA. Taken this together, the first arrival time $T_1$ for repair proteins is defined as $$T_1 = \begin{cases} t_d, & \text{for bound fraction } B_0 \\ t_s + t_d, & \text{for unbound fraction } (1 - B_0) \end{cases}. \qquad (12)$$

Given $t_s$ and $t_d$ are exponentially distributed, the probability distribution function (pdf) of $T_1$ is given by $$pdf(T_1) = \left(\frac{B_0}{\tau_d} + \frac{(1 - B_0)}{\tau_d - \tau_s}\right)\exp\left(-\frac{T_1}{\tau_d}\right) + \frac{(1 - B_0)}{\tau_s - \tau_d}\exp\left(-\frac{T_1}{\tau_s}\right). \qquad (13)$$

The distribution has three unknown parameters, $B_0$, $\tau_d$ and $\tau_s$. The fractional bound $B_0$ was measured independently from fraction of DSB, 1 minute after uncaging with ddPCR. The parameters $\tau_d$ and $\tau_s$ were determined by fitting the experimentally determined distribution of the first arrival time $T_1$ using maximum likelihood estimation. The expectation value of the first arrival time is $$<T1> = \tau_d + (1 - B_0)\tau_s \qquad (14)$$

After completion of the first round of repair, and if the repair is perfect or the resulting Indel can be recut, it is expected that active Cas9-gRNAs, generated by uncaging of gRNA, can search for the target site and cut it again. Because there is no pre-bound Cas9, the time gap $T_g$ between the end of a repair event and the beginning of the next repair is:

$$T_g = t_s + t_d \qquad (15)$$

which follows the distribution of $$pdf(T_g) = \frac{1}{\tau_d - \tau_s}\exp\left(-\frac{T_g}{\tau_d}\right) + \frac{1}{\tau_s - \tau_d}\exp\left(-\frac{T_g}{\tau_s}\right). \qquad (16)$$

Here, it was assumed that the search time follows the same distribution as the first round of search. The expectation value of $T_g$ is simply $(T_g)=\tau_d+\tau_s$. The mean values of T and $T_g$ can be related by $$(T_g)=(T_1)+B_0\tau_s \qquad (17)$$

So, it was expected that the mean value of the gap time $(T_g)$ should be longer than the first arrival time for $B_0\tau_s$ which is confirmed by the data (Table 6).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

---

What is claimed:

1. A guide RNA (gRNA) comprising a sequence having one or more caged nucleotides or analogs thereof in a guiding sequence of the gRNA, wherein the caged nucleotides or analogs thereof are in the PAM distal-half of the guiding sequence.

2. The gRNA of claim 1, wherein the one or more caged nucleotides or analogs thereof are photocleavable.

3. The gRNA of claim 2, wherein the photocleavable caged nucleotide is 6-nitropiperonyloxymethyl modified deoxynucleotide thymine (NPOM-dT).

4. The gRNA of claim 1, wherein the gRNA comprises at least one photocleavable caged nucleotides or analogs thereof, that comprise one or more caging groups comprising: 6-nitropiperonyloxymethyl; adenosine-5'-diphosphate, $P^2$-(1-(2-nitrophenyl)-ethyl)-ester or salt thereof; adenosine-5'-triphosphate, $P^3$-(1-(2-nitrophenyl)-ethyl)-ester or salt thereof; adenosine-5'-[(β,γ)-imido]triphosphate, $P^3$-(1-(2-nitrophenyl)-ethyl)-ester, or salt thereof; adenosine 5'-triphosphate, $P^3$-(1-(4,5-dimethoxy-2-nitrophenyl)ethyl) ester, or salt thereof; adenosine 5'-triphosphate, $P^3$-(1-(2-nitrophenyl)ethyl) ester, or salt thereof; 4,5-dimethoxy-2-nitrophenyl-ethyl (DMNPE); [7-(diethylamino)coumarin-4-yl] methyl (DEACM); or combinations thereof.

5. The gRNA of claim 1, wherein the gRNA comprises at least one photocleavable caged nucleotides or analogs thereof, that comprise one or more caging groups comprising: 6-nitropiperonyloxymethyl; adenosine-5'-diphosphate, $P^2$-(1-(2-nitrophenyl)-ethyl)-ester, potassium salt; adenosine-5'-triphosphate, $P^3$-(1-(2-nitrophenyl)-ethyl)-ester, sodium salt; adenosine-5'-[(β,γ)-imido]triphosphate, $P^3$-(1-(2-nitrophenyl)-ethyl)-ester, triethylammonium salt; adenosine 5'-triphosphate, $P^3$-(1-(4,5-dimethoxy-2-nitrophenyl)ethyl) ester, disodium salt; adenosine 5'-triphosphate, $P^3$-(1-(2-nitrophenyl)ethyl) ester, disodium salt; 4,5-dimethoxy-2-nitrophenyl-ethyl (DMNPE); [7-(diethylamino) coumarin-4-yl]methyl (DEACM); or combinations thereof.

6. The gRNA of claim 1, wherein one or more uracil nucleobases in the nucleic acid sequence of the gRNA are substituted with 6-nitropiperonyloxymethyl modified deoxynucleotide thymine (NPOM-dT).

7. The gRNA of claim 1, wherein the gRNA is complementary to a target sequence in a genome of a cell.

8. The gRNA of claim 7, wherein the target sequence comprises one or more genomic sequences associated with a disease.

9. The gRNA of claim 8, wherein the disease comprises: tumors, virus infections, autoimmunity diseases, diseases associated with genetic mutations or infectious disease organisms.

10. A kit comprising the guide RNA (gRNA) of claim 1.

11. A crRNA comprising one or more photocleavable caged nucleotides or analogs thereof in the PAM-distal half of the guiding sequence of the crRNA.

12. A composition comprising a clustered regularly interspaced short palindromic repeats (CRISPR)-associated endonuclease and at least one guide RNA, wherein the at least one guide RNA comprises at least one photocleavable caged nucleotide or analogs thereof in a crRNA region of the guide RNA, wherein the at least one photocleavable caged nucleotide or analogs thereof is in the PAM-distal half of the guide sequence of the crRNA region.

13. A method of modulating activity of a gene editing complex in a host cell, comprising:

contacting the host cell with a composition comprising: a clustered regularly interspaced short palindromic repeats (CRISPR)-associated endonuclease and at least one guide RNA (gRNA), wherein the at least one gRNA comprises at least one photocleavable caged nucleotide or analogs thereof in a guide sequence of the at least one gRNA, wherein the at least one photocleavable caged nucleotide or analogs thereof is in the PAM-distal half of the guide sequence;

subjecting the host cell to an electromagnetic radiation, thereby cleaving the at least one photocleavable caged nucleotide or analogs thereof; and, modulating activity of the gene-editing complex.

14. The method of claim 13, wherein the gRNA is substantially complementary to a target sequence in the genome of the host cell.

15. The method of claim 13, wherein the at least one photocleavable caged nucleotides or analogs thereof, comprise one or more caging groups comprising: 6-nitropiperonyloxymethyl; adenosine-5'-diphosphate, $P^2$-(1-(2-nitrophenyl)-ethyl)-ester or salt thereof; adenosine-5'-triphosphate, $P^3$-(1-(2-nitrophenyl)-ethyl)-ester or salt thereof; adenosine- 5'-[(β,γ)-imido]triphosphate, $P^3$-(1-(2-nitrophenyl)-ethyl)-ester, or salt thereof; adenosine 5'-triphosphate, $P^3$-(1-(4,5-dimethoxy-2-nitrophenyl)ethyl) ester, or salt thereof; adenosine 5'-triphosphate, $P^3$-(1-(2-nitrophenyl)ethyl) ester, or salt thereof; 4,5-dimethoxy-2-nitrophenyl-ethyl (DMNPE); [7-(diethylamino)coumarin-4-yl]methyl (DEACM); or combinations thereof.

16. The method of claim 13, wherein the at least one photocleavable caged nucleotides or analogs thereof, comprise one or more caging groups comprising: 6-nitropiperonyloxymethyl; adenosine-5'-diphosphate, $P^2$-(1-(2-nitrophenyl)-ethyl)-ester, potassium salt; adenosine-5'-triphosphate, $P^3$-(1-(2-nitrophenyl)-ethyl)-ester, sodium salt; adenosine-5'-[(β,γ)-imido]triphosphate, $P^3$-(1-(2-nitrophenyl)-ethyl)-ester, triethylammonium salt; adenosine 5'-triphosphate, $P^3$-(1-(4,5-dimethoxy-2-nitrophenyl)ethyl) ester, disodium salt; adenosine 5'-triphosphate, $P^3$-(1-(2-nitrophenyl)ethyl) ester, disodium salt; 4,5-dimethoxy-2-nitrophenyl-ethyl (DMNPE); [7-(diethylamino)coumarin-4-yl]methyl (DEACM); or combinations thereof.

17. A method of sequential activation of a gene-editing complex in a host cell comprising;

contacting the host cell with a composition comprising a clustered regularly interspaced short palindromic repeats (CRISPR)-associated endonuclease and at least two guide RNAs (gRNAs), wherein each of the at least two gRNAs comprises at least one photocleavable caged nucleotide or analogs thereof in a guide sequence, wherein the at least one photocleavable caged nucleotide or analogs thereof is in the PAM-distal half of the guide sequence of each of the at least two gRNAs;

subjecting the host cell to varying wavelengths of electromagnetic radiation over intervals of time, thereby cleaving the at least one photocleavable caged nucleotide or analogs thereof in each of the at least two gRNAs; and, modulating activity of the gene-editing complex.

\* \* \* \* \*

SEQUENCE LISTING

```
<160> NUMBER OF SEQ ID NOS: 64

<210> SEQ ID NO 1
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gcuauucucg cagcucacca guuuuagagc uaugcuguuu ug                        42

<210> SEQ ID NO 2
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
guuacuagac cuauagcuac guuuuagagc uaugcuguuu ug                        42

<210> SEQ ID NO 3
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
guaauuccag cgagaggcag guuuuagagc uaugcuguuu ug                        42

<210> SEQ ID NO 4
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gacuuccucu augguggcgu guuuuagagc uaugcuguuu ug                        42

<210> SEQ ID NO 5
<211> LENGTH: 42
<212> TYPE: RNA
<213> ORGANISM: Artificial Sequence
<220> FEATURE:
<223> OTHER INFORMATION: Description of Artificial Sequence: Synthetic
```

-continued

```
                oligonucleotide

<400> SEQUENCE: 5
uccucuguau gauaucacag guuuuagagc uaugcuguuu ug                    42

<210> SEQ ID NO 6
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugauaucaca gguuuuagag cuaugcuguu uug                             33

<210> SEQ ID NO 7
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
agcauagcaa guuaaaauaa ggcuaguccg uuaucaacuu gaaaaagugg caccgagucg    60
gugcuuu                                                         67

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggcggccta aggactcg                                             18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaagccggcc ttgcacatg                                            19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacaggagcc tcccggtttc                                           20

<210> SEQ ID NO 11
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 11
cttcagggtg aggatgcctc tc                                          22

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ctcacagcgc gcc                                                    13

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tgctcagggc ttcttg                                                 16

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcagtctga atcctgttaa c                                           21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctaaagtga actattgtat gag                                         23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtgtctattg tttggcctag t                                           21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
```

US 12,612,624 B2

-continued primer

<400> SEQUENCE: 17
gtgagaagga gactcattct                                              20

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tatcaagcac ggcag                                                   15

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
acctcagatc gttc                                                    14

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttggcgggaa aaagaacgg                                               19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tattcgctcc ggatctccct                                              20

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gccagcggtc cgcaac                                                  16

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 23
gagagccttt cagagaagcg g                                              21

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tatctaactc gctg                                                      14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
ttgcccatag cagc                                                      14

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tggcggccta aggactcg                                                  18

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cttcagggtg aggatgcctc tc                                             22

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctcagtctga atcctgttaa c                                              21

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 29
cacttctgaa acacttttct tac                                                    23

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttggcgggaa aaagaacgg                                                         19

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gagagccttt cagagaagcg g                                                      21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtttccgagg cagcagttg                                                         19

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcatgataaa cgtcatcgcc c                                                      21

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcgtcggcag cgtcagatgt gtataagaga cagtggcggc ctaaggactc g                     51

<210> SEQ ID NO 35
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

-continued

```
gtctcgtggg ctcggagatg tgtataagag acaggaagcc ggccttgcac atg          53

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcgtcggcag cgtcagatgt gtataagaga cagctcagtc tgaatcctgt taac          54

<210> SEQ ID NO 37
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtctcgtggg ctcggagatg tgtataagag acagcctaaa gtgaactatt gtatgag       57

<210> SEQ ID NO 38
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcgtcggcag cgtcagatgt gtataagaga caggggatcg cgctgagtat aaa           53

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtctcgtggg ctcggagatg tgtataagag acagtgggca aagtttcgtg ga            52

<210> SEQ ID NO 40
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcgtcggcag cgtcagatgt gtataagaga caggcccatc aaggggatct tga           53

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
```

-continued aatgatacgg cgaccaccga gatctacacc tctctattcg tcggcagcgt c                51

<210> SEQ ID NO 42
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aatgatacgg cgaccaccga gatctacact atcctcttcg tcggcagcgt c                51

<210> SEQ ID NO 43
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aatgatacgg cgaccaccga gatctacacg taaggagtcg tcggcagcgt c                51

<210> SEQ ID NO 44
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aatgatacgg cgaccaccga gatctacaca ctgcatatcg tcggcagcgt c                51

<210> SEQ ID NO 45
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aatgatacgg cgaccaccga gatctacaca aggagtatcg tcggcagcgt c                51

<210> SEQ ID NO 46
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aatgatacgg cgaccaccga gatctacacc taagccttcg tcggcagcgt c                51

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aatgatacgg cgaccaccga gatctacacc gtctaattcg tcggcagcgt c                51

-continued

```
<210> SEQ ID NO 48
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aatgatacgg cgaccaccga gatctacact ctctccgtcg tcggcagcgt c            51

<210> SEQ ID NO 49
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caagcagaag acggcatacg agattcgcct tagtctcgtg ggctcgg                 47

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
caagcagaag acggcatacg agatctagta cggtctcgtg ggctcgg                 47

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
caagcagaag acggcatacg agatttctgc ctgtctcgtg ggctcgg                 47

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
caagcagaag acggcatacg agatgctcag gagtctcgtg ggctcgg                 47

<210> SEQ ID NO 53
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
caagcagaag acggcatacg agataggagt ccgtctcgtg ggctcgg                 47
```

-continued

<210> SEQ ID NO 54
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caagcagaag acggcatacg agatcatgcc tagtctcgtg ggctcgg                    47

<210> SEQ ID NO 55
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caagcagaag acggcatacg agatgtagag aggtctcgtg ggctcgg                    47

<210> SEQ ID NO 56
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
caagcagaag acggcatacg agatcagcct cggtctcgtg ggctcgg                    47

<210> SEQ ID NO 57
<211> LENGTH: 425
<212> TYPE: DNA
<213> ORGANISM: Unknown
<220> FEATURE:
<223> OTHER INFORMATION: Description of Unknown:
      ACTB sequence

<400> SEQUENCE: 57
tggcggccta aggactcggc gcgccggaag tggccagggc gggggcgact tcggctcaca      60
gcgcgcccgg ctattctcgc agctcaccat ggatgatgat atcgccgcgc tcgtcgtcga     120
caacggctcc ggcatgtgca aggccggctt cgcgggcgac gatgccccc gggccgtctt      180 cccctccatc gtggggcgcc ccaggcacca ggtaggggag ctggctggt ggggcagccc      240 cgggagcggg cgggaggcaa gggcgctttc tctgcacagg agcctcccgg tttccggggt     300 ggggctgcg cccgtgctca gggcttcttg tcctttcctt cccagggcgt gatggtgggc      360
atgggtcaga agattcctat gtgggcgacg aggcccagag caagagaggc atcctcaccc     420
tgaag                                                                425

<210> SEQ ID NO 58
<211> LENGTH: 427
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
tggcggccta aggactcggc gcgccggaag tggccagggc gggggcgact tcggctcaca      60

```
gcgcgcccgg ctattctcgc agctcaacca tggatgatga tatcgccgcg ctcgtcgtcg        120
acaacggctc cggcatgtgc aaggccggct tcgcgggcga cgatgccccc cgggccgtct        180
tcccctccat cgtggggcgc cccaggcacc aggtagggga gctggctggg tggggcagcc        240
ccgggagcgg gcgggaggca agggcgcttt ctctgcacag gagcctcccg gtttccgggg        300
tgggggctgc gcccgtgctc agggcttctt gtcctttcct tcccagggcg tgatggtggg        360
catgggtcag aaggattcct atgtgggcga cgaggcccag agcaagagag gcatcctcac        420
cctgaag                                                                  427
```

```
<210> SEQ ID NO 59
<211> LENGTH: 412
<212> TYPE: DNA
<213> ORGANISM: Unknown
<220> FEATURE:
<223> OTHER INFORMATION: Description of Unknown:
      MYC sequence

<400> SEQUENCE: 59
ttggcgggaa aaagaacgga gggagggatc gcgctgagta taaaagccgg ttttcggggc         60
tttatctaac tcgctgtagt aattccagcg agaggcagag ggagcgagcg ggcggccggc        120
tagggtggaa gagccgggcg agcagagctg cgctgcgggc gtcctgggaa gggagatccg        180
gagcgaatag ggggcttcgc ctctggccca gccctcccgc tgatccccca gccagcggtc        240
cgcaaccctt gccgcatcca cgaaactttg cccatagcag cgggcgggca ctttgcactg        300
gaacttacaa cacccgagca aggacgcgac tctcccgacg cggggaggct attctgccca        360
tttggggaca cttccccgcc gctgccagga cccgcttctc tgaaaggctc tc               412
```

```
<210> SEQ ID NO 60
<211> LENGTH: 413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
ttggcgggaa aaagaacgga gggagggatc gcgctgagta taaaagccgg ttttcggggc         60
tttatctaac tcgctgtagt aattccagcg agaggccaga gggagcgagc gggcggccgg        120
ctagggtgga agagccgggc gagcagagct gcgctgcggg cgtcctggga agggagatcc        180
ggagcgaata gggggcttcg cctctggccc agccctcccg ctgatccccc agccagcggt        240
ccgcaaccct tgccgcatcc acgaaacttt gcccatagca gcgggcgggc actttgcact        300
ggaacttaca cacccgagc aaggacgcga ctctcccgac gcggggaggc tattctgccc        360
atttggggac acttccccgc cgctgccagg acccgcttct ctgaaaggct ctc             413
```

```
<210> SEQ ID NO 61
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
ttggcgggaa aaagaacgga gggagggatc gcgctgagta taaaagccgg ttttcggggc         60
tttatctaac tcgctgtagt aattccagcg agagcagagg gagcgagcgg gcggccggct        120
```

-continued

```
agggtggaag agccgggcga gcagagctgc gctgcgggcg tcctgggaag ggagatccgg    180
agcgaatagg gggcttcgcc tctggcccag ccctcccgct gatcccccag ccagcggtcc    240
gcaacccttg ccgcatccac gaaactttgc ccatagcagc gggcgggcac tttgcactgg    300
aacttacaac acccgagcaa ggacgcgact ctcccgacgc ggggaggcta ttctgcccat    360
ttggggacac ttccccgccg ctgccaggac ccgcttctct gaaaggctct c            411

<210> SEQ ID NO 62
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gtctcgtggg ctcggagatg tgtataagag acagctgggg tctgggtagg taac              54

<210> SEQ ID NO 63
<211> LENGTH: 11
<212> TYPE: DNA
<213> ORGANISM: Unknown
<220> FEATURE:
<223> OTHER INFORMATION: Description of Unknown:
      ACTB sequence

<400> SEQUENCE: 63
gctcaccatg g                                                             11

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gctcaaccat gg                                                            12
```